(12) United States Patent
Beria et al.

(10) Patent No.: US 9,556,192 B2
(45) Date of Patent: Jan. 31, 2017

(54) FUNCTIONALIZED 9-BROMO-CAMPTOTHECIN DERIVATIVES

(71) Applicant: NERVIANO MEDICAL SCIENCES S.R.L., Nerviano (MI) (IT)

(72) Inventors: Italo Beria, Nerviano (IT); Michele Caruso, Milan (IT); Matteo Salsa, Bellinzago Novarese (IT); Daniela Faiardi, Pavia (IT)

(73) Assignee: NERVIANO MEDICAL SCIENCES S.R.L., Nerviano (MI) (IT)

( * ) Notice: Subject to any disclaimer, the term of this patent is extended or adjusted under 35 U.S.C. 154(b) by 0 days.

(21) Appl. No.: 14/439,020

(22) PCT Filed: Oct. 29, 2013

(86) PCT No.: PCT/EP2013/072633
§ 371 (c)(1),
(2) Date: Apr. 28, 2015

(87) PCT Pub. No.: WO2014/067960
PCT Pub. Date: May 8, 2014

(65) Prior Publication Data
US 2015/0291613 A1   Oct. 15, 2015

(30) Foreign Application Priority Data
Oct. 30, 2012  (EP) .................................. 12190612

(51) Int. Cl.
| | |
|---|---|
| *A61K 31/4745* | (2006.01) |
| *C07D 491/22* | (2006.01) |
| *C07D 491/147* | (2006.01) |
| *A61K 31/496* | (2006.01) |
| *A61K 38/06* | (2006.01) |
| *A61K 45/06* | (2006.01) |
| *C07K 5/08* | (2006.01) |

(52) U.S. Cl.
CPC ....... *C07D 491/147* (2013.01); *A61K 31/4745* (2013.01); *A61K 31/496* (2013.01); *A61K 38/06* (2013.01); *A61K 45/06* (2013.01); *C07D 491/22* (2013.01); *C07K 5/08* (2013.01)

(58) Field of Classification Search
USPC ........................................... 514/283; 546/48
See application file for complete search history.

(56) References Cited

U.S. PATENT DOCUMENTS

| 4,943,579 A | 7/1990 | Vishnuvajjala et al. | |
|---|---|---|---|
| 6,169,080 B1 * | 1/2001 | Hausheer ............. | C07D 491/22 514/283 |

FOREIGN PATENT DOCUMENTS

| EP | 0624377 A2 | 11/1994 |
|---|---|---|
| EP | 2357006 A2 | 8/2011 |
| WO | WO 92/02255 A1 | 2/1992 |
| WO | WO 98/35940 A1 | 8/1998 |
| WO | WO 01/49691 A1 | 7/2001 |
| WO | WO 02/083180 A1 | 10/2002 |
| WO | WO 03/014069 A1 | 2/2003 |
| WO | WO 2004/043493 A1 | 5/2004 |
| WO | WO 2005/079398 A2 | 9/2005 |
| WO | WO 2005/105154 A1 | 11/2005 |
| WO | WO 2006/012527 A1 | 2/2006 |
| WO | WO 2010/009124 A2 | 1/2010 |

OTHER PUBLICATIONS

Colombo M. et al., "A Fully Automated Method for Accurate Mass Determination Using High-Performance Liquid Chromatography With a Quadrupole/Orthogonal Acceleration Time-of-Flight Mass Spectrometer", Rapid Communications in Mass Spectrometry 18:511-517 (2004).
Fassberg J. et al., "A Kinetic and Mechanistic Study of the Hydrolysis of Camptothecin and Some Analogues", Journal Pharmaceutical Sciences 81(7):676-684 (Jul. 1992).
Gottlieb J.A. et al., "Preliminary Pharmacologic and Clinical Evaluation of Captothecin Sodium (NSC-100880)", Cancer Chemotherapy Reports Part 1 54(6):461-470 (Dec. 1970).
Greenwald R.B. et al., "Effective Drug Delivery by PEGylated Drug Conjugates", Advanced Drug Delivery Reviews 55:217-250 (2003).
Hsiang Y-H et al., "DNA Topoisomerase I-Mediated DNA Cleavage and Cytotoxicity of Camptothecin Analogues", Cancer Research 49:4385-4389 (Aug. 15, 1989).

(Continued)

*Primary Examiner* — Charanjit Aulakh
(74) *Attorney, Agent, or Firm* — Scully, Scott, Murphy & Presser, P.C.

(57) ABSTRACT

The present disclosure is directed to a compound of formula (I)

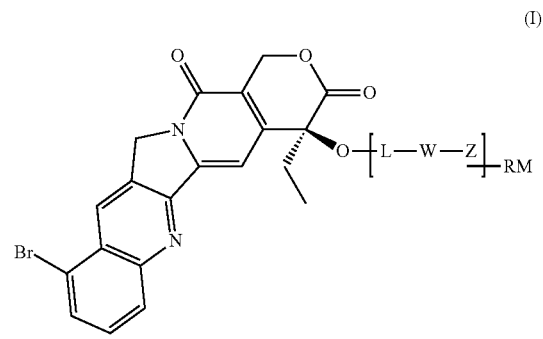

wherein L is null or a conditionally-cleavable moiety; W is null or a self-immolative system, comprising one or more self-immolative groups; Z is null or a peptidic, non peptidic or hybrid —peptidic and non peptidic—linker; RM is null or a reactive moiety that can be attached to one or more of L, W or Z groups, or RM is attached to oxygen when L, W and Z are all null; provided that at least one of L, W, Z and RM is not null; or a pharmaceutically acceptable salt thereof.

8 Claims, 9 Drawing Sheets

(56) References Cited

OTHER PUBLICATIONS

Ishimi Y. et al., "Biochemical Activities Associated With Mouse Mcm2 Protein", The Journal of Biological Chemistry 276(46):42744-42752 (Nov. 16, 2001).

Jaxel C. et al., "Structure-Activity Study of the Actions of Camptothecin Derivatives on Mammalian Topoisomerase I: Evidence for a Specific Receptor Site and a Relation to Antitumor Activity", Cancer Research 49:1465-1469 (Mar. 15, 1989).

Kingsbury W.D. et al., "A Novel Peptide Delivery System Involving Peptidase Activated Prodrugs as Antimicrobial Agents. Synthesis and Biological Activity of Peptidyl Derivatives of 5-Fluorouracil", Journal of Medicinal Chemistry 27 (11):1447-1451 (1984).

Lajiness J.P. et al., "Design, Synthesis, and Evaluation of Duocarmycin O-Amino Phenol Prodrugs Subject to Tunable Reductive Activation", Journal of Medicinal Chemistry 53(21):7731-7738 (2010).

Rasheed Z A et al., "Mechanisms of Resistance to Topoisomerase I-Targeting Drugs", Oncogene 22:7296-7304 (2003).

Sawada S. et al., "Synthesis and Antitumor Activity of 20(S)-Camptothecin Derivatives: A-Ring Modified and 7,10-Disubstituted Camptothecins", Chem. Pharm. Bull. 39(12):3183-3188 (Dec. 1991).

Tranoy-Opalinski I. et al., "Design of Self-Immolative Linkers for Tumour-Activated Prodrug Therapy", Anti-Cancer Agents in Medicinal Chemistry 8(6):618-637 (2008).

Wall M.E. et al., "Plant Antitumor Agents. Synthesis and Structure Activity of Novel Camptothecin Analogs", Journal of Medicinal Chemistry 36(18):2689-2700 (1993).

Walker M.A. et al., "Synthesis of an Immunoconjugate of Camptothecin", Bioorganic & Medicinal Chemistry Letters 12:217-219 (2002).

Wani M.C. et al., "Plant Antitumor Agents. Total Synthesis and Antileukemic Activity of Ring A Substituted Camptothecin Analogues. Structure-Activity Correlations", Journal of Medicinal Chemistry 30(10):1774-1779 (1987).

Zhao R Y et al., "Synthesis and Biological Evaluation of Antibody Conjugates of Phosphate Prodrugs of Cytotoxic DNA Alkylators for the Targeted Treatment of Cancer", Journal of Medicinal Chemistry 55:766-782 (2012).

International Search Report dated Nov. 25, 2013 issued in PCT/EP2013/072633.

* cited by examiner

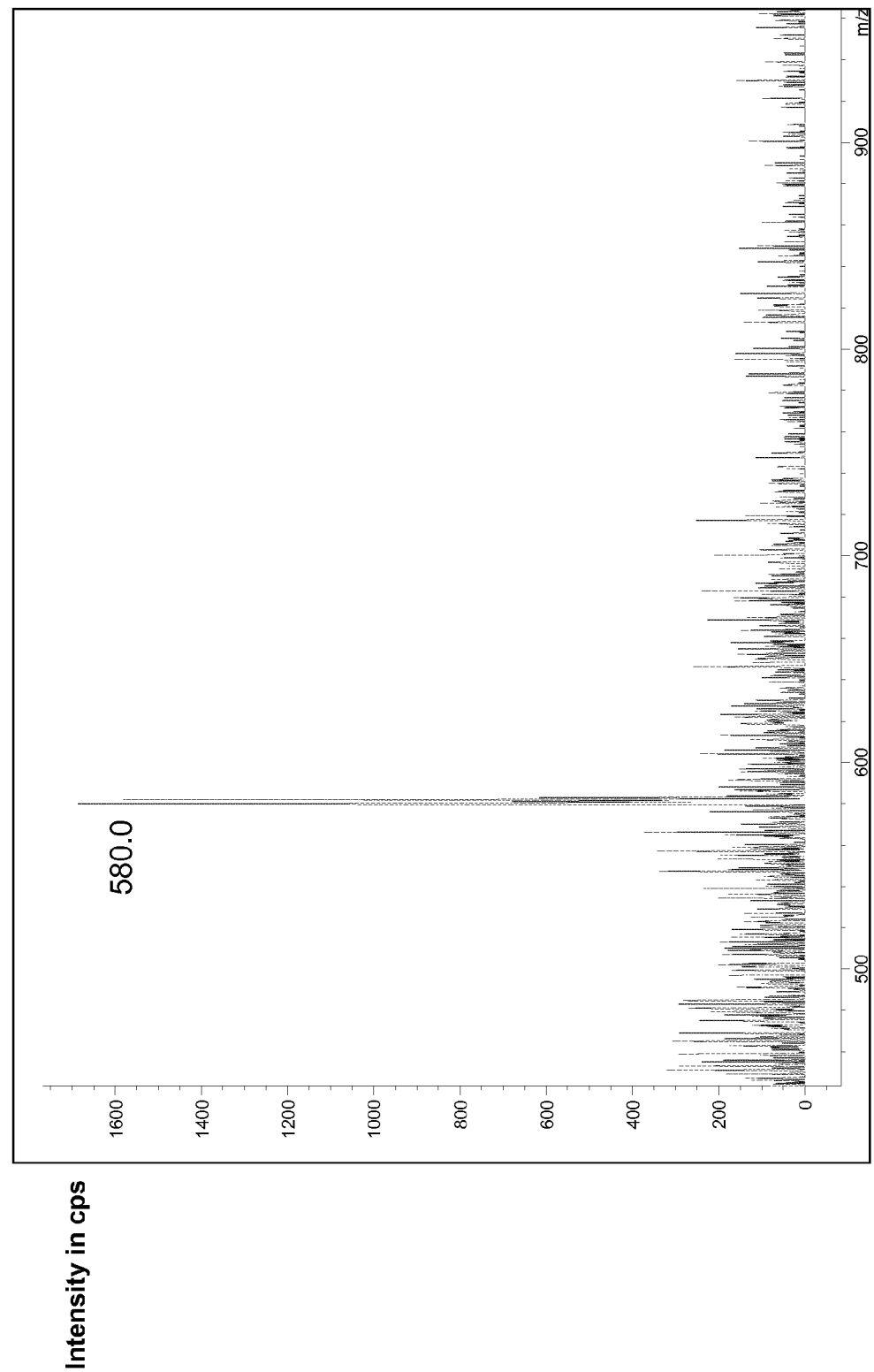

FUNCTIONALIZED 9-BROMO-CAMPTOTHECIN DERIVATIVES

The present invention relates to new functionalized 9-bromo-camptothecin derivatives, methods for their preparation, pharmaceutical composition containing them and use thereof in treating certain mammalian tumors. The invention also relates to their use in the preparation of conjugates.

Camptothecin and some of its analogs are cytotoxics that display potent antitumor activity by inhibiting topoisomerase I which is a monomeric enzyme which controls the changes in DNA structure by catalyzing the breaking and rejoining of the phosphodiester backbone of DNA strands during the normal cell cycle and it is thus involved in some important cellular functions and cell growth. For a general reference to camptothecin and its derivatives see for instance, Wani et al., J. Med. Chem: 1987, 30, 1774; Hsiang et al., Cancer Res. 1989, 49, 4385 and Cancer Res. 1989, 49, 1465. Specifically, the synthesis and antitumor activity of the 9-bromo-camptothecin is described in Chem Pharm Bull. 1991, 39(12), 3183-3188.

Human DNA topoisomerase I (Topo I) is an essential enzyme that relaxes DNA supercoiling during replication and transcription and is recognize to be validated target for the treatment of human cancers.

In recent years, Topo I has become a popular target for cancer chemotherapy treatments. It is thought that Topo I inhibitors such as camptothecin and its analogs, block the ligation step of the cell cycle, generating single and double stranded breaks that harm the integrity of the genome. Introduction of these breaks subsequently lead to apoptosis and cell death (for a review on topoisomerase inhibitors see e.g. *Oncogene* 2003, 22, 7296-7304).

Topotecan and irinotecan are two camptothecin derivatives that are approved for the treatment of a variety of malignancies, including colorectal, ovarian, and small cell lung cancers, as well as myeloid malignancies.

There are, however, certain limitations to the use of the camptothecin derivatives in clinical. These include: low solubility, spontaneous inactivation to a lactone form in blood, rapid reversal of the trapped cleavable complex after drug removal, inadequate accumulation in the tumor, prolonged time of infusions, resistance of cancer cells overexpressing membrane transporters and dose-limiting side effects such as diarrhea and neutropenia.

In addition, due to the low solubility, camptothecin required to be formulated as the ring-opened carboxylate salt that, other than being inactive, is also considered responsible in part of its toxicity (see, for instance, Cancer Chemother. Rep. Part 1 1970, 54, 461; J. Pharm. Sci. 1992, 81, 676; Bioorg. Med. Chem. Lett. 2002, 12, 217).

Thus there is an increasing need of new camptothecin derivatives with high solubility so that to improve formulation and/or pharmacokinetic/pharmacodynamic properties.

Drug conjugation of cytotoxic drugs to molecules able to vehicle the drug thus improving tumor targeting or able to modify its pharmacokinetic properties is one of the strategies that has been undertaken to solve the above mentioned issues.

Different examples of conjugation of cytotoxics drugs with proteins, peptides, aptamers, polymers or nanoparticles allowing better target delivery, improving solubility and in some cases other pharmacokinetic properties such as increasing half life or local concentration of the drug and improving drug performances have been reported. As a matter of facts, the resultant conjugates have improved characteristics in terms of solubility, permeability into the cell, in vivo therapeutic window, controlled release, ability to reach the target according to the nature of the specific molecule conjugated with the cytotoxic agent, etc.

For this reason, there is an increasing demand for the development of functionalized cytotoxic agents suitable to be conjugated with different types of molecules.

The first object of the present invention is to provide functionalized 9-bromo-camptothecin derivatives which, other than having cytotoxic activity, have high solubility so that to improve formulation and/or pharmacokinetic/pharmacodynamic properties. Furthermore these functionalized 9-bromo-camptothecin derivatives are also suitable to be conjugated.

Accordingly, a first object of the present invention is to provide a compound of formula (I)

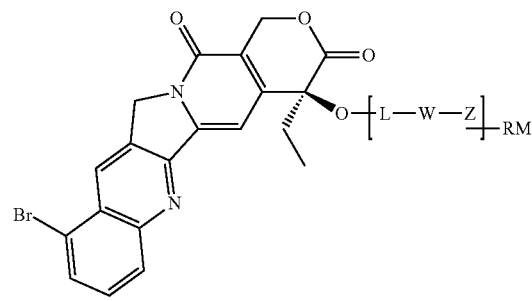

wherein:
L is null or a conditionally-cleavable moiety;
W is null or a self-immolative system, comprising one or more self-immolative groups;
Z is null or a peptidic, non peptidic or hybrid—peptidic and non peptidic—linker;
RM is null or a reactive moiety that can be attached to one or more of L, W or Z groups, provided that at least one of L, W, Z and RM is not null, or RM is attached to oxygen when L, W and Z are all null or a pharmaceutically acceptable salt thereof.

The present invention also provides methods of synthesizing the compounds of formula (I), prepared through a process consisting of standard synthetic transformations, and isomers, tautomers, hydrates, solvates, complexes, metabolites, prodrugs, carriers and N-oxides thereof.

The present invention also provides a method for treating cancer, which comprises administering to a mammal in need thereof an effective amount of a compound of formula (I) as defined above. The mammal in need thereof may be for example a human.

The present invention also provides a compound of formula (I), as defined above, for use in a method of treating cancer, cellular proliferation disorders and viral infections.

Preferably, a compound of formula (I), as defined above, is for use in a method of treating specific types of cancers, including but not limited to: carcinomas, such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkitt's lymphoma; hematopoietic tumors of myeloid lineage, including acute and chronic myelogenous leukemia, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannoma; other tumors, including melanoma, seminoma, teratocarcinoma, osteosarcoma, xeroderma pigmentosum, keratoxanthoma, thyroid follicular cancer, Kaposi's sarcoma and mesothelioma.

Furthermore, a compound of formula (I), as defined above, is for use in a method of treating specific cellular proliferation disorders such as, for example, benign prostate hyperplasia, familial adenomatosis polyposis (FAP), neurofibromatosis, psoriasis, vascular smooth cell proliferation associated with atherosclerosis, pulmonary fibrosis, arthritis, glomerulonephritis and post-surgical stenosis and restenosis.

In addition, a compound of formula (I), as defined above is for use in a method of inhibiting tumor angiogenesis and metastasis, as well as in a method of treating organ transplant rejection and host versus graft disease.

The present invention also provides a pharmaceutical composition comprising a therapeutically effective amount of a compound of formula (I), or a pharmaceutically acceptable salt thereof as defined above, and at least one pharmaceutically acceptable excipient, carrier or diluent.

The present invention further provides a pharmaceutical composition comprising a compound of formula (I), or a pharmaceutically acceptable salt thereof as defined above, and one or more chemotherapeutic agents.

The present invention further provides a pharmaceutical composition comprising a compound of formula (I), or a pharmaceutically acceptable salt thereof as defined above, in combination with known anticancer treatments, such as radiation therapy or chemotherapy regimen, and/or in combination with cytostatic or cytotoxic agents, antibiotic -type agents, alkylating agents, antimetabolite agents, hormonal agents, immunological agents, interferon-type agents, cyclooxygenase inhibitors (e.g. COX-2 inhibitors), matrix-metalloproteinease inhibitors, telomerase inhibitors, tyrosine kinase inhibitors, anti-growth factor receptor agents, anti-HER2 agents, anti-EGFR agents, anti -angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

Additionally, the invention provides a product comprising a compound of formula (I), or a pharmaceutically acceptable salt thereof as defined above, and one or more chemotherapeutic agents, as a combined preparation for simultaneous, separate or sequential use in anticancer therapy.

In yet another aspect the invention provides a compound of formula (I) or a pharmaceutically acceptable salt thereof, as defined above, for use as a medicament.

Moreover the invention provides the use of a compound of formula (I), or a pharmaceutically acceptable salt thereof as defined above, in the manufacture of a medicament with anticancer activity.

Finally, the invention provides the use of a compound of formula (I) or a pharmaceutically acceptable salt thereof, as defined above, in the preparation of conjugates.

BRIEF DESCRIPTION OF THE FIGURES

FIG. 4a shows the mass spectrum of the released Comp. 11 and reports the molecular weight (m/z) on the x axis while intensity expressed as counts per second (cps) is reported on the y axis.

Figure 1:
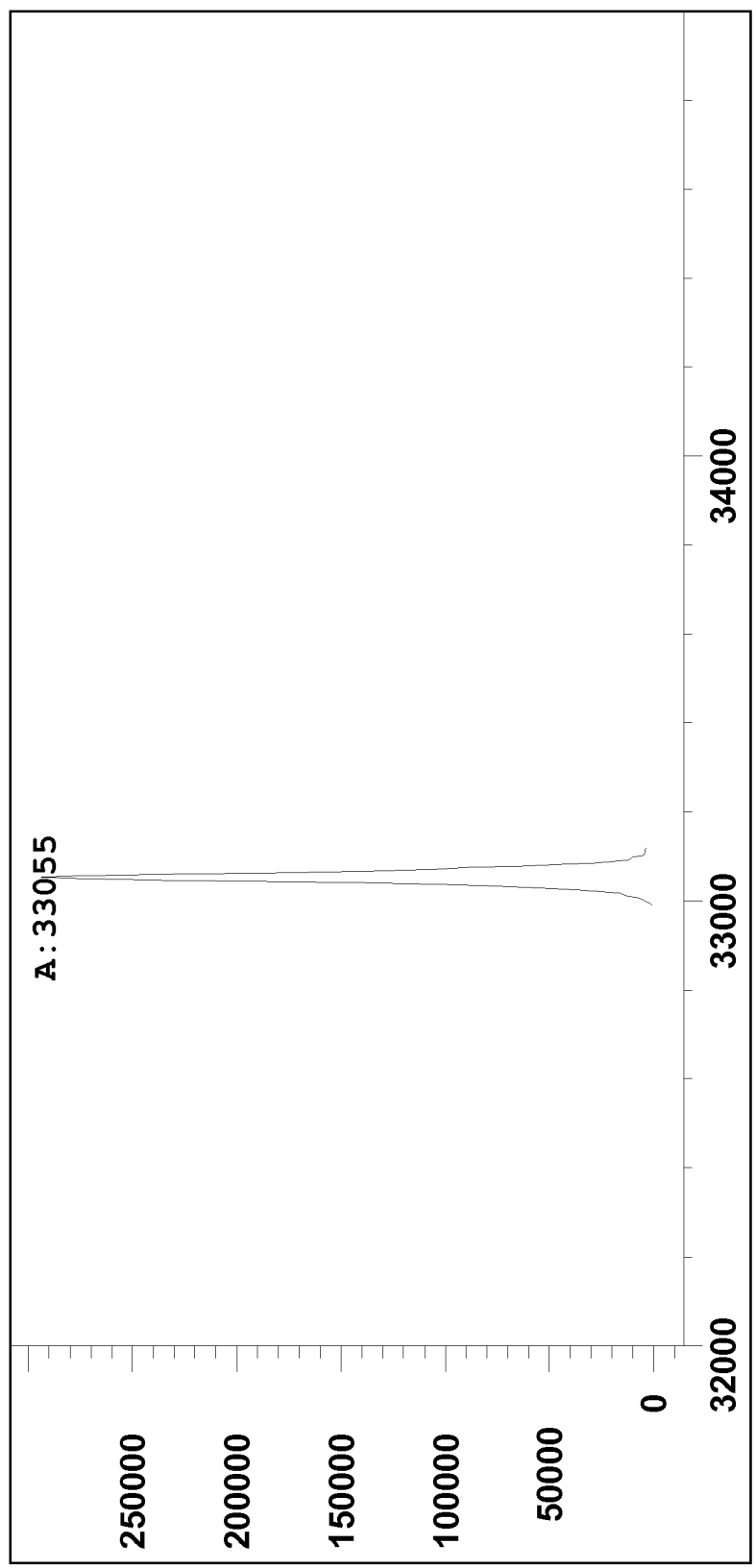
FIG. 1 shows the deconvoluted mass spectrum of unreacted MCM2 protein and reports the molecular weight (m/z) on the x axis, while intensity expressed as counts per second (cps) is reported on the y axis.

Unless stated otherwise, the following terms and phrases as used herein are intended to have the following meanings.

With the term "linear or branched $C_1$-$C_4$ alkyl" we intend any of the groups such as, for instance, methyl, ethyl, n-propyl, isopropyl, n-butyl, isobutyl, sec-butyl, tert-butyl.

With the term "linear or branched $C_1$-$C_4$ hydroxyalkyl" we intend any of the groups such as, for instance, 2-hydroxyethyl, 3-hydroxypropyl, 2-hydroxypropyl, 4-hydroxybutyl, 3-hydroxybutyl, 2-hydroxybutyl.

With the term "linear or branched $C_1$-$C_4$ alkoxy", we intend any of the groups such as, for instance, methoxy, ethoxy, propoxy, tert-butoxy, etc.

The term "polyfluorinated alkyl" or "polyfluorinated alkoxy" means any of the above linear or branched $C_1$-$C_4$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term "halogen" we intend a fluorine, chlorine, bromine or iodine.

With the term "linear or branched $C_1$-$C_4$ aminoalkyl" we intend any of the groups such as, for instance, 2-aminoethyl, 3-aminopropyl, 4-aminobutyl, 3-aminobutyl, etc.

The term "linear or branched $C_1$-$C_4$ sulfhydrylalkyl" as used herein refers to a —SH group appended to a linear or branched $C_1$-$C_4$ alkyl group, as previously defined.

The term "$C_3$-$C_8$ cycloalkyl" as used herein refers to a saturated or unsaturated non-aromatic all-carbon monocyclic ring, which may consist of one ring or two or more rings fused together. Examples include, but are not limited to, cyclopropyl, cyclobutyl, cyclopentyl, cyclopentenyl, cyclopentadienyl, cyclohexyl, cyclohexenyl, 1,3-cyclohexadienyl, decalinyl, and 1,4-cyclohexadienyl.

The term "heterocyclyl" as used herein refers to a saturated or unsaturated non-aromatic $C_4$-$C_8$ carbocyclic ring which may consist of one ring or two or more rings fused together, wherein from 1 to 4 carbon atoms are replaced by heteroatoms such as nitrogen, oxygen, sulfur, wherein said heteroatoms may be directly connected to each other; nitrogen and sulfur may optionally be oxidized and nitrogen may optionally be quaternized. Non limiting examples of heterocyclyl groups are, for instance, tetrahydrofuranyl, pyrrolidinyl, piperidinyl, 1,4-dioxanyl, decahydroquinolinyl, piperazinyl, oxazolidinyl and morpholinyl.

The term "aryl" as used herein refers to a mono-, bi- or poly-carbocyclic hydrocarbon from 1 to 4 ring systems, optionally further fused or linked to each other by single bonds, wherein at least one of the carbocyclic rings is aromatic, wherein the term "aromatic" refers to a completely conjugated π-electron bond system. Non limiting examples of such aryl groups are phenyl, α- or β-naphthyl or anthracenyl groups.

The term "heteroaryl" as used herein refers to aromatic heterocyclic rings, typically 4- to 7-membered heterocycles, with from 1 to 4 heteroatoms selected among oxygen, nitrogen and sulfur, wherein nitrogen and sulfur may optionally be oxidized and nitrogen may optionally be quaternized; said heteroaryl ring can be optionally further fused or linked to one or two or more rings fused together, aromatic and non-aromatic carbocyclic and heterocyclic rings. Heteroatoms may be directly connected to each other. Examples of heteroaryl groups include, but are not limited to, pyridyl, pyrimidyl, furanyl, pyrrolyl, triazolyl, pyrazolyl, pyrazinyl, oxazolyl, isoxazolyl, thiazolyl, imidazolyl, thienyl, indolyl, benzofuranyl, benzimidazolyl, benzothiazolyl, purinyl, indazolyl, benzotriazolyl, benzisoxazolyl, quinoxalinyl, isoquinolyl, and quinolyl. In one embodiment, a heteroaryl group comprises from 1 to 4 heteroatoms. It should be noted that "$C_1$ heteroaryl group" denotes that there is only one carbon present in the ring system of the heteroaromatic group (carbon atoms in optional substituents are thus not counted). An example of such a heteroaromatic group is tetrazolyl group.

The term "activating moiety" refers to a functional group that improves chemical reactivity of the chemical function to which the activating moiety is attached. Chemical functions that can be activated in such way are, for instance, amine and carbonyl. Examples of activated amines are alkylsulfonyloxyamine, alkylsulfonyloxycarbamate, phenylsulfonyloxyamine, phenylsulfonyloxycarbamate. Examples of activated carbonyl groups are, for example, activated esters.

The term "activated ester" refers to a functional group in which the alkoxy group of the ester moiety is a good leaving group. Examples of such alkoxy groups include, but are not limited to, succinimide-N-oxide, p-nitrophenoxide, pentafluorophenoxide, tetrafluorophenoxide, 1-hydroqbenzotriazole, and 1-hydroxy-7-azabenzotriazole, and groups with comparable leaving capability. Unsubstituted alkyl-based alkoxy groups such as methoxy, ethoxy, isopropoxy, and tert-butoxy do not qualify as good leaving groups and methyl, ethyl, isopropyl, and tert-butyl esters are therefore not considered to be activated esters.

It is known to the person skilled in the art that transformation of a chemical functional group into another may require that one or more reactive centers in the compound containing such functional group have to be protected in order to avoid undesired side reactions. Protection of such reactive centers, and subsequent deprotection at the end of the synthetic transformations, can be accomplished following standard procedures described in the literature (see, for instance, Green, Theodora W. and Wuts, Peter G. M. —Protective Groups in Organic Synthesis, Third Edition, John Wiley & Sons Inc., New York (N.Y.), 1999).

Therefore, the term "protecting group" refers to a group used to protect such reactive centers in a chemical synthesis, for example, a hydroxyl group (—OH), an amino group (—NH), a thiol group (—SH), a carbonyl group (—C=O), a carboxylic group (—COOH). Examples of protecting groups are those reported in the literature (see, for instance, ibidem).

The term "nucleophiles" refers to molecules that bear a nucleophilic group. The term "nucleophilic group" refers to a species that donates an electron-pair to an electrophilic group to form a chemical bond in a chemical reaction. Examples of such nucleophilic groups include, but are not limited to halogens, amines, nitrites, azides, alcohols, alkoxyde anions, carboxylate anions, thiols, thiolates, etc.

The term "electrophilic group" refers to a species that accepts an electron-pair from a nucleophilic group to form a chemical bond in a chemical reaction. Examples of such electrophilic groups include, but are not limited to esters, aldehydes, amides, ketons, etc.

The term "unnatural aminoacid" refers to the D-stereoisomer of the naturally occurring aminoacid (L-stereoisomer). Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, fumaric, lactic, oxalic, malonic, malic, maleic, tartaric, citric, benzoic, cinnamic, mandelic, methanesulphonic, isethionic and salicylic acid.

Pharmaceutically acceptable salts of the compounds of formula (I) also include the salts with inorganic or organic bases, e.g., alkali or alkaline-earth metals, especially sodium, potassium, calcium ammonium or magnesium hydroxides, carbonates or bicarbonates, acyclic or cyclic amines.

If a stereogenic center or another form of an isomeric center is present in a compound of the present invention, all forms of such isomer or isomers, including enantiomers and diastereoisomers, are intended to be covered herein. Compounds containing a stereogenic center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention.

In cases when compounds can exist in tautomeric forms, each form is contemplated as being included within this invention whether existing in equilibrium or predominantly in one form.

The Conditionally-Cleavable Moiety L

The L moiety, if present, is a conditionally-cleavable group that can be cleaved by a chemical, photochemical, physical, biological or enzymatic process upon being brought in or under certain conditions. One of these conditions may for example be bringing a compound of the invention in an aqueous environment, which leads to hydrolysis of L or bringing a compound of the invention in an environment that contains an enzyme that recognizes and cleaves L, or bringing a compound of the invention under reducing conditions, which leads to reduction and/or removal of L, or bringing a compound of the invention under oxidizing conditions, which leads to oxidation and removal of L, or bringing a compound of the invention in contact with radiation, e.g., UV light, which leads to cleavage, or bringing a compound of the invention in contact with heat, which leads cleavage of L. This condition may be met directly after administering a compound of this invention to an animal, e.g. a mammal, for example a human, due to the presence of ubiquitous enzymes in the circulation. Alternatively, said condition may be met when the compound localizes to a specific organ, tissue, cell, subcellular target, or bacterial, viral, or microbial target, for example by the presence of internal factors (e.g. target-specific enzymes or hypoxia) or application of external factors (e.g. radiation, magnetic fields).

Cleavage of L means that the bond between the oxygen and L in a compound of formula (I) is broken:

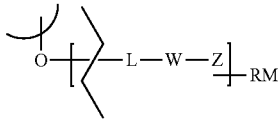

In one embodiment, L can be a moiety that is cleaved by an enzyme or hydrolytic conditions present in the vicinity or inside the target cells as compared to other parts of the body, or by an enzyme or hydrolytic conditions present only in the vicinity of or inside the target cells. It is important to recognize that if target site specificity is achieved solely based upon the selective transformation and/or cleavage of said L at the target site, the condition causing the cleavage should preferably, at least to a certain degree, be target site-specific.

In one embodiment, cleavage of L occurs intracellularly.

In another embodiment, cleavage of L occurs extracellularly.

In another embodiment, cleavage of L can occur by a ubiquitous intracellular enzyme.

In one preferred embodiment, L may be a moiety that can be cleaved by ubiquitous enzymes, e.g., esterases that are present in the circulation or intracellular enzymes, such as for example proteases and phosphatases, or by pH -controlled hydrolysis. L may therefore form, optionally together with the connecting atom oxygen, a hydroxylamine, carbamate, urea, ester, ether, acetal, ketal or phosphate group that can be cleaved in vivo.

In a more preferred embodiment L is independently null or a group selected from:

—NHCO—R1; (IIa)

—NHCONH—R1; (IIb)

—NHCOO—R1; (IIc)

—NH—R1; (IId)

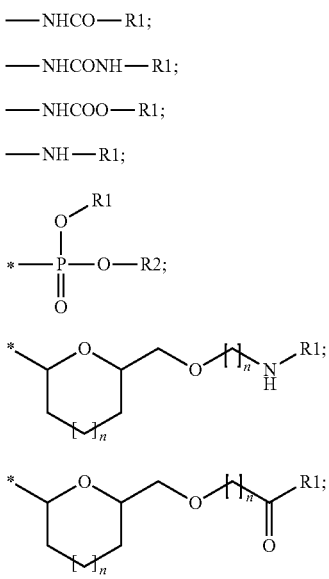

(IIe)

(IIf)

(IIg)

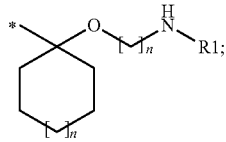

(IIh)

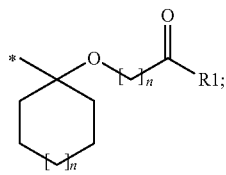

(IIi)

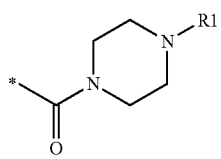

(IIj)

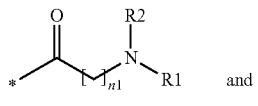

(IIk) and

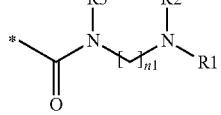

(IIm)

wherein:

R1, R2 and R3 are, each independently, null, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl, linear or branched $C_1$-$C_4$ aminoalkyl, linear or branched $C_1$-$C_4$ alkylcarbonyl and linear or branched $C_1$-$C_4$ alkoxycarbonyl;

each of n is independently an integer from 0 to 2, and n1 is an integer from 0 to 5.

★ indicates the attachment points to the other moieties in the compound of formula (I), herewith and throughout the application.

According to the present invention and unless otherwise provided, the above R1, R2 and R3 groups may be optionally substituted, in any of their free positions, by one or more groups, for instance 1 to 3 groups, independently selected from: halogen, linear or branched $C_1$-$C_4$ alkyl, polyfluorinated $C_1$-$C_4$ alkyl, linear or branched $C_1$-$C_4$ alkoxy, polyfluorinated $C_1$-$C_4$ alkoxy, hydroxy, amino, linear or branched $C_1$-$C_4$ alkylamino, di-$C_1$-$C_4$ alkylamino, $C_1$-$C_4$ alkylcarbonyl, $C_3$-$C_8$ cycloalkyl, $C_3$-$C_8$ cycloalkyl-$C_1$-$C_4$ alkyl, heterocyclyl, heterocyclyl-$C_1$-$C_4$ alkyl, aryl, aryl-$C_1$-$C_4$ alkyl, heteroaryl and heteroaryl-$C_1$-$C_4$ alkyl.

The Self-Immolative System W

The W group, if present, is a self-immolative system that in a compound of formula (I) tethers in a stable way a moiety L (or oxygen, if L is null) to a moiety Z (or RM, if Z is null). The L-W, or O—W, bond can become labile upon activation by a chemical, photochemical, physical, biological or enzymatic process upon being brought in or under certain conditions, as described above, leading optionally to the release of the corresponding moieties:

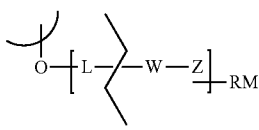

A self-immolative system may be incorporated in a compound of formula (I) for example to improve solubility or to improve space between the 9-bromo-camptothecin derivative and the reactive moiety; in addition said self-immolative group can modulate the reactivity of RM versus nucleophiles.

Self-immolative systems are known to the person skilled in the art, see for example those described in WO2002/083180 and WO2004/043493; or those described in Tranoy-Opalinsi, A. et al., Anticancer Agents in Medicinal Chemistry, 2008, 8, 618-637. Other examples of self-immolative groups include, but are not limited to, optionally substituted 4-aminobutyric acid amides, appropriately substituted bicyclo[2.2.1] and bicyclo[2.2.2] ring systems or 2-aminophenylpropionic acid amides [see WO2005/079398, WO2005/105154 and WO2006/012527; Greenwald, R. B., et al., Adv. Drug Delivery Rev. 2003, 55, 217-250; Kingsbury, W. D., et al., J. Med. Chem. 1984, 27, 1447-1451].

In one preferred embodiment, W may form, together with the connecting atom(s) oxygen, L, Z, or RM, a carbonate, carbamate, urea, ester, thioamide, phosphate, amide, hydroxylamine or ether linkage that can be optionally cleaved upon activation.

In a more preferred embodiment, W is independently null or a group selected from:

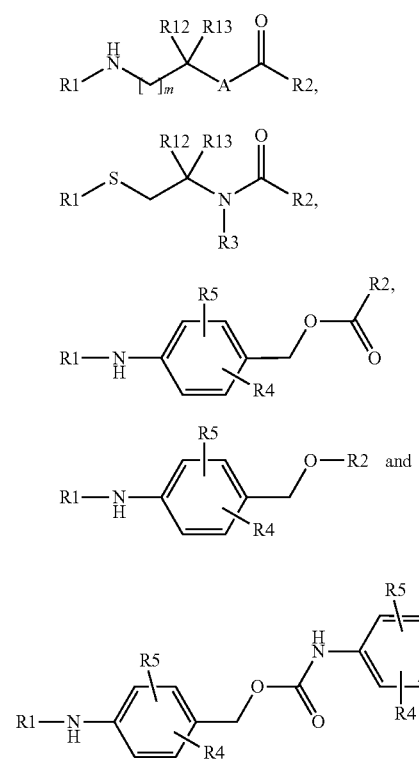

wherein
one of R1 and R2 is null and the other is as defined above;
R3 is as defined above;
R4 and R5 are, each independently, halogen, methyl, ethyl or linear or branched $C_1$-$C_4$ hydroxyalkyl;
m is an integer from 0 to 3;
A is $C_1$-$C_3$ alkyl, $CH_2NH$, NH or N—R4, wherein R4 is as defined above; and
R12 and R13 are, each independently, hydrogen, halogen, methyl, ethyl, linear or branched $C_1$-$C_4$ hydroxyalkyl, linear or branched $C_1$-$C_4$ haloalkyl, or R12 and R13 taken together form a 3- to 6-membered carbocycle.

In another more preferred embodiment, W is independently null or a group selected from:

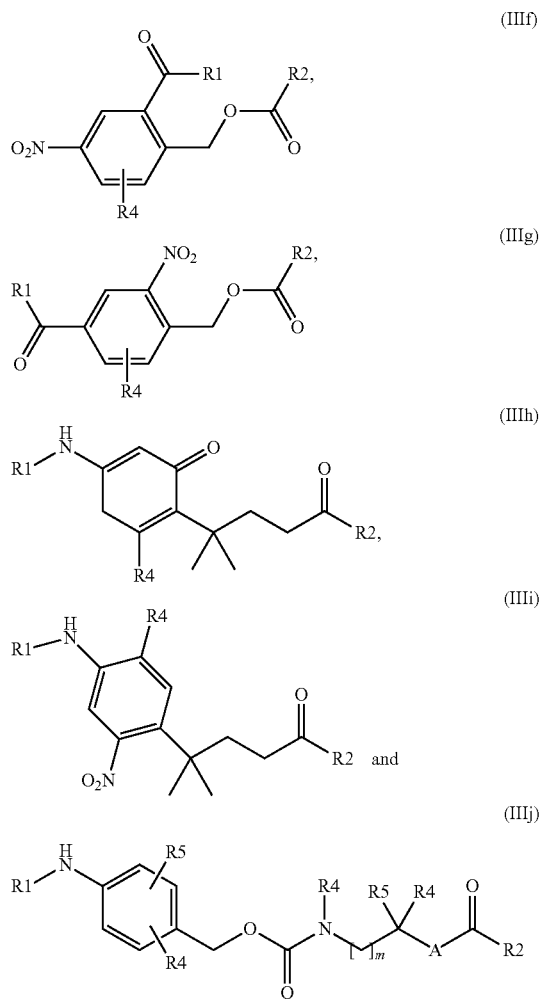

wherein one of R1 and R2 is null and the other is as defined above; and
R4, R5 and A are as defined above.

The Z Linker

The Z linker, if present, can be peptidic (Z1), non-peptidic (Z2) or hybrid (Z3), wherein said hybrid linker is peptidic and non-peptidic; in a compound of formula (I) said Z linker can be cleaved from the left-hand side moiety (W, L or oxygen) by a chemical, photochemical, physical, biological or enzymatic process upon being brought in or under certain conditions, as described above:

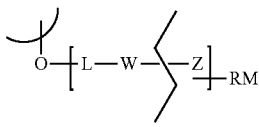

The Z linker may be linear or branched.

The linkage between Z and its left-hand side moiety or between Z and, optionally, RM may be an amide, a carbonate, an urea, an ester, a thioamide, a disulfide, an hydroxylamine or a carbamate linkage.

In one embodiment Z is null.

In another embodiment Z is a peptidic linker Z1 that can be cleaved by a proteolytic enzyme, plasmin, a cathepsin, β-glucuronidase, a galactosidase, prostate-specific antigen (PSA), urokinase-type plasminogen activator (u-PA) or a member of the family of matrix metalloproteinases.

In another embodiment Z, is a non-peptidic linker Z2 that may contain one or more non-peptidic water-soluble moieties. In this case the linker contributes to the water solubility of a compound of formula (I). In another embodiment Z2 is a non-peptidic linker that may contain one or more non-peptidic moieties that reduce(s) aggregation of a compound of formula (I) which may or may not be a moiety/moieties that also increase(s) the water solubility of a compound of formula (I).

For example, non-peptidic water-soluble Z2 linkers may contain an oligoethylene glycol or polyethylene glycol moiety or a derivative thereof.

In another embodiment, Z is a hybrid linker Z3 that can contain both peptidic and non peptidic residues of general formula Z1-Z2, wherein Z1 and Z2 are independently a peptidic linker or a non-peptidic linker. Hybrid linkers may contribute to solubility of the compound of formula (I) and/or may be a substrate that can be cleaved by proteolytic enzymes, for example by a member of the family of matrix metalloproteinases.

In a preferred embodiment, Z1 is a single aminoacid, a dipeptide, a tripeptide, a tetrapeptide, or an oligopeptide moiety comprising natural L-aminoacids, unnatural D-aminoacids, synthetic aminoacids, or any combination thereof, wherein one of the C-terminal or the N-terminal aminoacid residue is linked to W, L or oxygen, and the other terminal aminoacid ends with a COOH or NH$_2$ group or is optionally linked to RM.

In a more preferred embodiment Z1 is a dipeptide or a tripeptide, linked via its C-terminus to W, or to L when W is null, or to oxygen when W and L are both null.

In another more preferred embodiment, the C-terminal aminoacid residue of the dipeptide or of the tripeptide is selected from glycine, leucine, alanine, arginine and citrulline; and the N-terminal aminoacid residue is selected from any natural or unnatural aminoacid; preferably, in case of the tripeptide, the middle aminoacid residue is selected from alanine, valine, leucine, isoleucine, methionine, phenylalanine and proline.

In another more preferred embodiment Z1 comprises a pentapeptide, wherein the C-terminal aminoacid is selected from any natural or unnatural aminoacid and the N-terminal aminoacid residue is 6-aminohexanoic acid.

In a preferred embodiment, Z2 may contain an oligoethylene glycol or polyethylene glycol moiety or a derivative thereof.

In a more preferred embodiment Z2 is a group selected from:

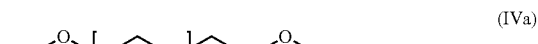 (IVa)

 (IVb)

 (IVc)

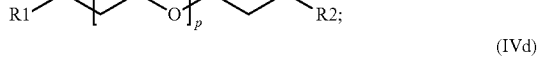 (IVd)

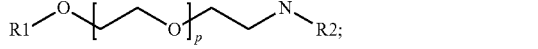 (IVe)

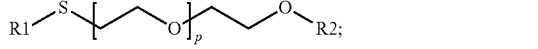 (IVf)

 (IVg)

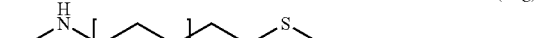 (IVh)

 (IVi)

 (IVj)

 (IVk)

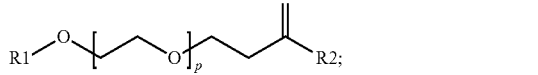 (IVm)

 (IVn)

 (IVo)

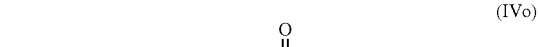 and (IVp)

wherein
one of R1 and R2 is null and the other is as defined above and
p is an integer from 1 to 20.

In a preferred embodiment Z3 is a hybrid moiety comprising a peptidic moiety Z1, wherein Z1 is a single aminoacid, a tripeptide or a tetrapeptide, comprising natural L-aminoacids and unnatural D-aminoacids; and a non-peptidic moiety Z2, wherein Z2 is an oligoethylene glycol or polyethylene glycol moiety or a derivative thereof.

In another preferred embodiment Z is a group selected from:
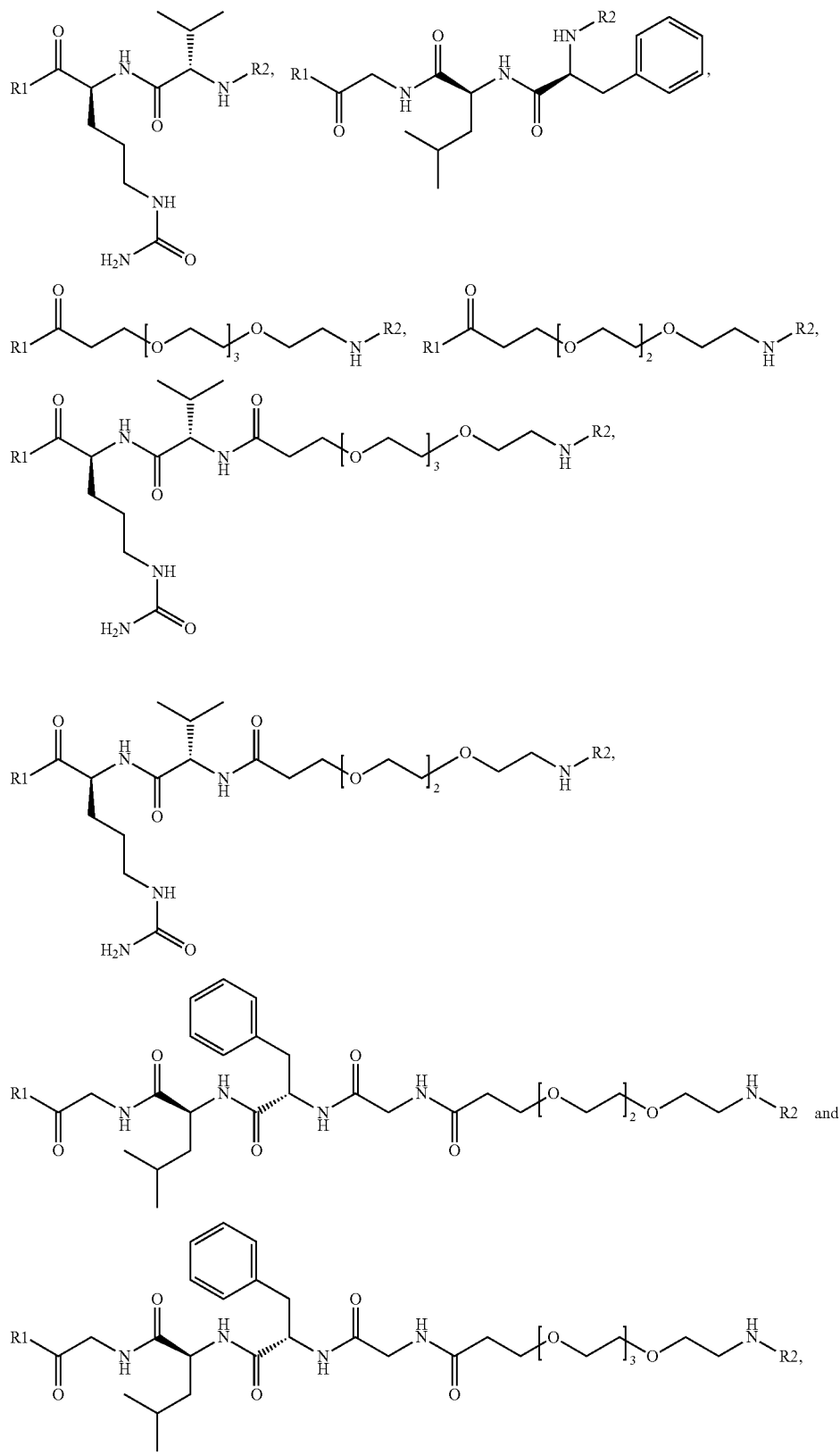

wherein
one of R1 and R2 is null and the other is as defined above.

The Reactive Moiety RM

The RM moiety, if present, is an electrophilic group that can react with nucleophiles, i.e. molecules that bear a nucleophilic group, under relatively mild conditions and without the need of prior functionalization of the reactive moiety, said reaction between said reactive moiety and said nucleophile requiring only the application of one or more of the agents selected from the group comprising heat, pressure, a catalyst, an acid and a base.

Therefore, when the RM moiety is present, a compound of formula (I) conjugates with different types of nucleophiles. When RM is null, a compound of formula (I) conjugates with different types of electrophiles, i.e. molecules that bear an electrophilic group, through one or more of the nucleophilic groups that are present on the L, W, and/or Z moiety(ies).

In a compound of formula (I) the RM moiety can be connected to one or more of the L, W or Z groups or to the oxygen atom of the 9-bromo-camptothecin derivative:

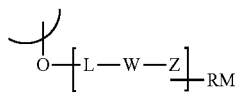

Examples of reactive moieties include, but are not limited to, carbamoyl halide, acyl halide, activated ester, anhydride, α-haloacetyl, α-haloacetamide, maleimide, isocyanate, isothiocyanate, disulfide, thiol, hydrazine, hydrazide, sulfonyl chloride, aldehyde, methyl ketone, vinyl sulfone, halomethyl, and methyl sulfonate.

In one preferred embodiment of the invention, when the nucleophilic group of the nucleophile, which RM can react with, is NH, NH$_2$, SH or OH, RM is independently null or a group selected from

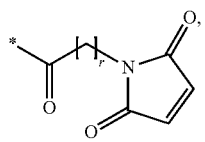
(Va)

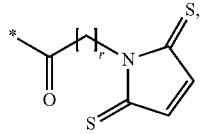
(Vb)

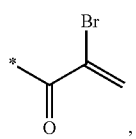
(Vc)

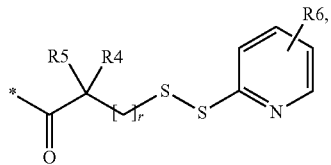
(Vd)

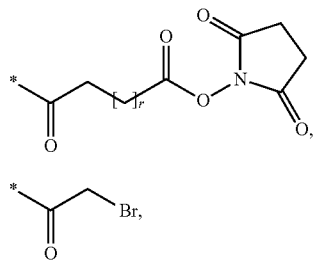
(Ve)

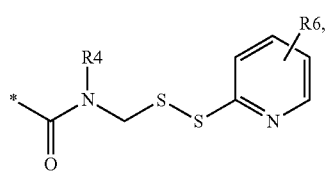
(Vf)

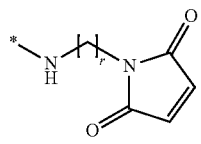
(Vg)

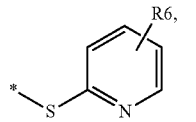
(Vh)

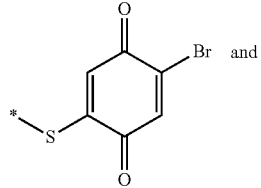
(Vk)

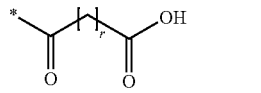
(Vm)

(Vn)

wherein R6 is C$_1$-C$_3$ alkyl or an electron-withdrawing group, comprising NO$_2$ and CN group;
r is an integer from 0 to 7, and
R4 and R5 are as defined above.

In another preferred embodiment of the invention, when the nucleophilic group of the nucleophile, which RM can react with, is COOH, RM is independently null or a group selected from

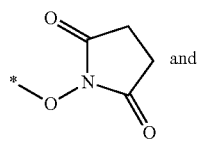
(Vi)

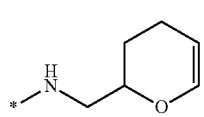
(Vj)

Specific, not limiting, preferred compounds (Comp.) of the present invention, optionally in the form of a pharmaceutically acceptable salt, are the following:

1) (4S)-10-bromo-4-ethyl-3,14-dioxo-3,4,12,14-tetrahydro-1H-pyrano[3',4':6,7]indolizino[1,2-b]quinolin-4-yl glycinate;
2) (4S)-10-bromo-4-ethyl-3,14-dioxo-3,4,12,14-tetrahydro-1H-pyrano[3',4':6,7]indolizino[1,2-b]quinolin-4-yl L-phenylalanyl-L-leucylglycinate;
3) (4S)-10-bromo-4-ethyl-3,14-dioxo-3,4,12,14-tetrahydro-1H-pyrano[3',4':6,7]indolizino[1,2-b]quinolin-4-yl piperazine-1-carboxylate;
4) (4S)-10-bromo-4-ethyl-3,14-dioxo-3,4,12,14-tetrahydro-1H-pyrano[3',4':6,7]indolizino[1,2-b]quinolin-4-yl N-[6-(2,5-dioxo-2,5-dihydro-1H-pyrrol-1-yl)hexanoyl]-L-phenylalanyl-L-leucylglycinate;
5) N-[6-(2,5-dioxo-2,5-dihydro-1H-pyrrol-1-yl)hexanoyl]-L-valyl-N-{4-[({[4-({[(4S)-10-bromo-4-ethyl-3,14-dioxo-3,4,12,14-tetrahydro-1H-pyrano[3',4':6,7]indolizino[1,2-b]quinolin-4-yl]oxy}carbonyl)piperazin-1-yl]carbonyl}oxy)methyl]phenyl]-$N^5$-carbamoyl-L-omithinamide;
6) (4S)-10-bromo-4-ethyl-3,14-dioxo-3,4,12,14-tetrahydro-1H-pyrano[3',4':6,7]indolizino[1,2-b]quinolin-4-yl 4-[6-(2,5-dioxo-2,5-dihydro-1H-pyrrol-1-yl)hexanoyl]piperazine-1-carboxylate;
7) (4S)-10-bromo-4-ethyl-3,14-dioxo-3,4,12,14-tetrahydro-1H-pyrano[3',4':6,7]indolizino[1,2-b]quinolin-4-yl methyl[2-(methylamino)ethyl]carbamate;
8) N-[6-(2,5-dioxo-2,5-dihydro-1H-pyrrol-1-yl)hexanoyl]-L-valyl-N-[4-({[{2-[({[(4S)-10-bromo-4-ethyl-3,14-dioxo-3,4,12,14-tetrahydro-1H-pyrano[3',4':6,7]indolizino[1,2-b]quinolin-4-yl]oxy}carbonyl)(methyl)amino]ethyl}(methyl)carbamoyl]oxy}methyl)phenyl]-$N^5$-carbamoyl-L-omithinamide;
9) (4S)-10-bromo-4-ethyl-3,14-dioxo-3,4,12,14-tetrahydro-1H-pyrano[3'4':6,7]indolizino[1,2-b]quinolin-4-yl 4-amino-3,3-dimethylbutanoate hydrochloride;
10) (4S)-10-bromo-4-ethyl-3,14-dioxo-3,4,12,14-tetrahydro-1H-pyrano[3'4':6,7]indolizino[1,2-b]quinolin-4-yl 5-amino-4,4-difluoropentanoate hydrochloride;
11) 4S)-10-bromo-4-ethyl-3,14-dioxo-3,4,12,14-tetrahydro-1H-pyrano[3'4':6,7]indolizino[1,2-b]quinolin-4-yl [1-(aminomethyl)cyclohexyl]acetate hydrochloride;
12) L-valyl-N-[4-({[(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)carbamoyl]oxy}methyl)phenyl]-$N^5$-carbamoyl-L-omithinamide;
13) L-valyl-N-[4-({[(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)carbamoyl]oxy}methyl)phenyl]-$N^5$-carbamoyl-L-omithinamide;
14) L-valyl-N-(4-{[({[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}carbamoyl)oxy]methyl}phenyl)-$N^5$-carbamoyl-L-omithinamide;
15) N-[6-(2,5-dioxopyrrolidin-1-yl)hexanoyl]-L-valyl-N-[4-({[(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)carbamoyl]oxy}methyl)phenyl]-$N^5$-carbamoyl-L-omithinamide;
16) N-[6-(2,5-dioxo-2,5-dihydro-1H-pyrrol-1-yl)hexanoyl]-L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-$N^5$-carbamoyl-L-omithinamide;
17) N-[6-(2,5-dioxo-2,5-dihydro-1H-pyrrol-1-yl)hexanoyl]-L-valyl-N-{[1-(2-{[(4S)-10-bromo-4-ethyl-3,14-dioxo 3,4,12,14-tetrahydro-1H-pyrano[3',4':6,7]indolizino[1,2-b]quinolin-4-yl]oxy}-2-oxoethyl)cyclohexyl]methyl}-$N^5$-carbamoyl-L-omithinamide;
18) N-[6-(2,5-dioxo-2,5-dihydro-1H-pyrrol-1-yl)hexanoyl]-L-valyl-N-(4-{[(4S)-10-bromo-4-ethyl-3,14-dioxo -3,4,12,14-tetrahydro-1H-pyrano[3',4':6,7]indolizino[1,2-b]quinolin-4-yl]oxy}-2,2-dimethyl-4-oxobutyl)-$N^5$-carbamoyl-L-omithinamide;
19) N-(3-carboxypropanoyl)-L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-$N^5$-carbamoyl-L-omithinamide;
20) N-(3-carboxypropanoyl)-L-valyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-$N^5$-carbamoyl-L-omithinamide;
21) N-(3-carboxypropanoyl)-L-valyl-N-(4-{[(4S)-10-bromo-4-ethyl-3,14-dioxo-3,4,12,14-tetrahydro-1H pyrano[3',4':6,7]indolizino[1,2-b]quinolin-4-yl]oxy}-2,2-dimethyl-4-oxobutyl)-$N^5$-carbamoyl-L-omithinamide;
22) N-[6-(2,5-dioxo-2,5-dihydro-1H-pyrrol-1-yl)hexanoyl]-L-phenylalanyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-L-leucinamide;
23) N-[6-(2,5-dioxo-2,5-dihydro-1H-pyrrol-1-yl)hexanoyl]-L-phenylalanyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2oxoethyl)cyclohexyl]methyl}-L-leucinamide;
24) N-[6-(2,5-dioxo-2,5-dihydro-1H-pyrrol-1-yl)hexanoyl]-L-phenylalanyl-N-(4-{[(4S)-10-bromo-4-ethyl-3,14-dioxo -3,4,12,14-tetrahydro-1H-pyrano[3',4':6,7]indolizino[1,2-b]quinolin-4-yl]oxy}-2,2-dimethyl-4-oxobutyl)-L-leucinamide;
25) L-valyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-$N^5$-carbamoyl-L-omithinamide;
26) L-valyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-$N^5$-carbamoyl-L-omithinamide, and
27) L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-$N^5$-carbamoyl-L-omithinamide.

For a reference to any specific compound of formula (I) of the invention, optionally in the form of a pharmaceutically acceptable salt, see the experimental section and claims.

The present invention also provides a process for the preparation of a compound of formula (I), as defined above, by using the reaction routes and synthetic schemes described below, employing the techniques available in the art and starting materials readily available. The preparation of certain embodiments of the present invention is described in the examples that follow, but those of ordinary skill in the art will recognize that the preparations described may be readily adapted to prepare other embodiments of the present invention. For example, the synthesis of non-exemplified compounds according to the invention may be performed by modifications apparent to those skilled in the art, for instance by appropriately protecting interfering groups, by employing other suitable reagents known in the art, or by making routine modifications of reaction conditions. Alternatively, other reactions referred to herein or known in the art will be recognized as having adaptability for preparing other compounds of the invention.

All those with ordinary skills in the art will appreciate that any transformation performed according to said methods may require standard modifications such as, for instance, protection of interfering groups, change to other suitable reagents known in the art, or make routine modifications of reaction conditions.

Accordingly, the process for the preparation of a compound of formula (I) is depicted in Scheme 1 below:

Scheme 1

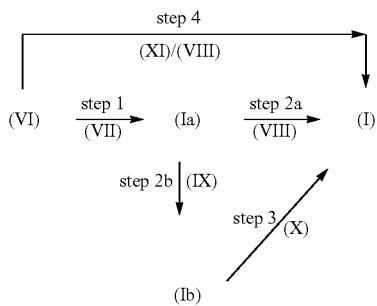

The present invention provides a process for the preparation of a compound of formula (I) as defined above, characterized in that the process comprises the following steps:

1) reacting a compound of formula (VI)

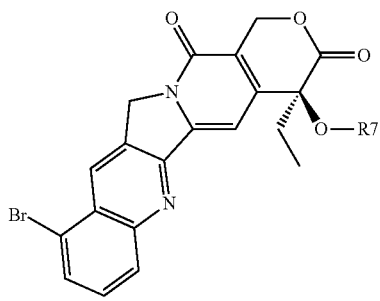

(VI)

wherein R7 is hydrogen, alternatively with:
1a) a compound of formula (VIIa)

R8—L (VIIa)

wherein R8 is an activating moiety of the NH group, preferably tosyl, and L is a group of formula —NHCOR1 (IIa), —NHCONH—R1 (IIb), —NHCOO—R1 (IIc), or —NH—R1 (IId), wherein R1 is as defined above but not null, and then removing the protecting group if present; or 1b) a compound of formula (VIIb)

Q—O—L (VIIb)

wherein Q is hydrogen or an activating moiety of the carboxylic group, e.g. an activated ester, and L is a group of formula (IIe) or (IIk)

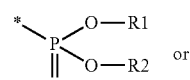 (IIe)

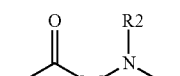 (IIk)

wherein

R1 and R2 are as defined above but not null and n1 is as defined above, and then removing the protecting group if present; or 1c) a compound of formula (VIIf) or (VIIg)

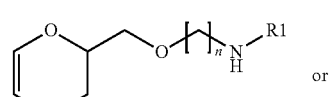 (VIIf)

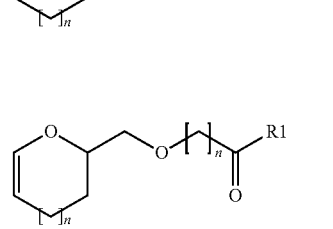 (VIIg)

wherein n is as defined above ad R1 is as defined above but not null, and then removing the protecting group if present; or 1d) a compound of formula (VIIh) or (VIIi)

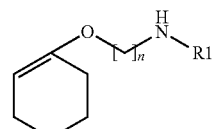 (VIIh)

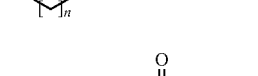 (VIIi)

wherein R1 is as defined above but not null and n is as defined above, and then removing the protecting group if present; or 1e) reacting a compound of formula (VI) as defined above, wherein R7 is an imidazol-1-yl-carbonyl moiety, with a compound of formula (VIIj) or (VIIm)

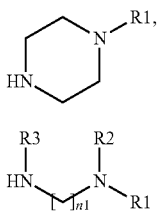

(VIIj)

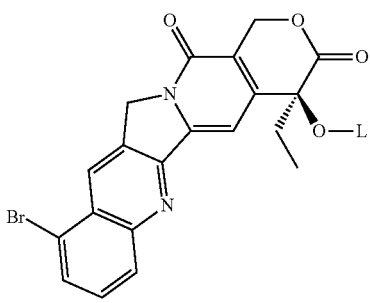

(VIIm)

wherein R1 is as defined above but not null, and R2, R3 and n1 are as defined above;

2) converting the resultant compound of formula (Ia)

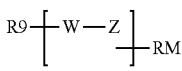

(Ia)

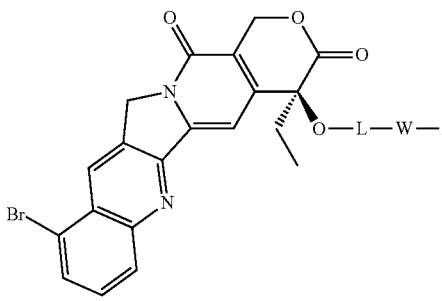

wherein L is a group of formula (IIa) to (IIm), wherein R1 is hydrogen or hydroxy, and R2, R3, n and n1 are as defined above, alternatively into:

2a) a compound of formula (I) as defined above, by reaction with a compound of formula (VIII)

$$R9 \!-\!\!\left[\!\!\begin{array}{c} W\!-\!Z \end{array}\!\!\right]\!\!-\!RM$$ (VIII)

wherein R9 is hydrogen, hydroxy or a carbonyl group activating moiety, preferably 4-nitrophenyl-oxy, and W, Z and RM are as defined above but not all null, and then removing the protecting group if present; or into 2b) a compound of formula of formula (Ib)

(Ib)

wherein L and W are as defined above, and Z is a group Z1, wherein the ending aminoacid has a COOH or NH free group; or a group Z2 of formula (IVa)-(IVp), wherein R1 or R2 is selected from hydrogen and hydroxy; or a group Z3, wherein Z1 and Z2 are as defined above, by reaction with a compound of formula (IX)

R9—W—Z (IX)

wherein R9 and W are as defined above, and Z is a group Z1, wherein the ending aminoacid has a COOH or NH free group; or a group Z2 of formula (IVa)-(IVp), wherein R1 or R2 is selected from hydrogen and hydroxy; or a group Z3, wherein Z1 and Z2 are as defined above, and then removing the protecting group if present; then 3) converting a compound of formula (Ib) as defined above, to a compound of formula (I) as defined above, by reaction with a compound of formula (X)

R10—RM (X)

wherein R10 is halogen, hydroxy, or an activating moiety of the carboxylic group, e.g. an activated ester; or 4) reacting a compound of formula (VI) as defined above, alternatively with:

4a) a compound of formula (XI)

$$R11 \!-\!\!\left[\!\!\begin{array}{c} W\!-\!Z \end{array}\!\!\right]\!\!-\!RM$$ (XI)

wherein R11 is a group of formula (VIIa), (VIIb), (VIIf), (VIIg), (VIIh) or (VIIi), wherein R1 is null, to obtain a compound of formula (I) wherein W, Z and RM are as defined above and L is as defined above but not null; or with 4b) a compound of formula (VIII) as defined above, to obtain a compound of formula (I) as defined above, wherein L is null and W, Z and RM are as defined above, or a pharmaceutically acceptable salt thereof.

Alternatively, a compound of formula (I) can be also prepared according to Scheme 2 depicted below:

Scheme 2

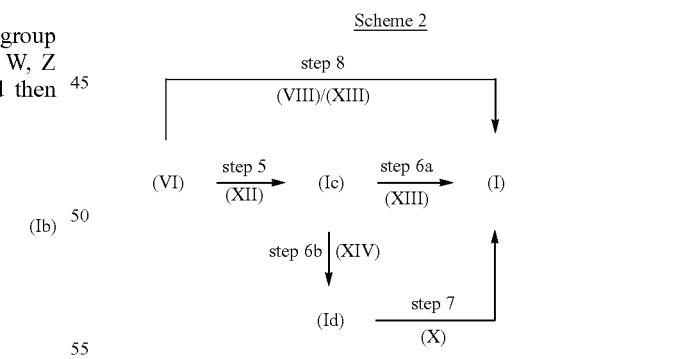

characterized in that the process comprises the following steps:

5) reacting a compound of formula (VI) as defined above, with a compound of formula (XII)

R9—W (XII)

wherein R9 is as defined above, and W is as defined above, wherein R1 and R2 are as defined above but not null, and then removing the protecting group if present; then, reacting the resultant compound of formula (Ic)

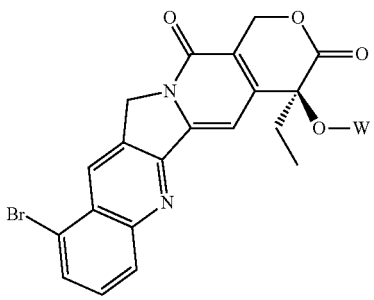

(Ic)

wherein W is a group (IIIa)-(IIIe), wherein R1 and R2 are as defined above but not null, alternatively with, 6a) a compound of formula (XIII)

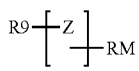

(XIII)

wherein R9 is as defined above and Z and RM are as defined above but not all null, to obtain a compound of formula (I) wherein W is as defined above but not null, and Z and RM are as defined above but not null; or with 6b) a compound of formula (XIV)

R9—Z     (XIV)

wherein R9 is as defined above and Z is a group Z1, wherein the ending aminoacid has a COOH or NH free group; or a group Z2 of formula (IVa)-(IVp), wherein R1 or R2 is selected from hydrogen and hydroxy; or a group Z3, wherein Z1 and Z2 are as defined above, and then removing the protecting group if present; and 7) finally, reacting the resultant compound of formula (Id)

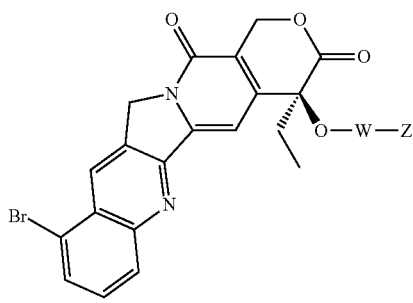

(Id)

wherein W is as defined above but not null and Z is a group Z1, wherein the ending aminoacid has a COOH or NH free group; or a group Z2 of formula (IVa)-(IVp), wherein R1 or R2 is selected from hydrogen and hydroxy; or a group Z3,wherein Z1 and Z2 are as defined above, with a compound of formula (X)

R10—RM     (X)

wherein R10 is as defined above, to obtain a compound of formula (I), wherein W is as defined above but not null and Z and RM are as defined above but RM is not null; or 8) reacting a compound of formula (VI) as defined above with:

8a) a compound of formula (VIII) as defined above, to obtain a compound of formula (I), wherein W, Z and RM are as defined above but not all null, or with 8b) a compound of formula (XIII) as defined above, to obtain a compound of formula (I), wherein W is null, and Z and RM are as defined above but not all null;

or a pharmaceutically acceptable salt thereof.

According to step 1a) the reaction is performed in an organic solvent, preferably diethyl ether, dioxane or a mixture thereof, with LIHMDS at a temperature ranging from −10° C. to 50° C. and for a time ranging from 30 min to about 24 h (J. Med. Chem., 2010, 53, 7731).

According to step 1b) the reaction is performed in an organic solvent, preferably DMSO, DCM, THF, CH$_3$CN or CCl$_4$, optionally in the presence of a base, preferably DIPEA or DMAP, at a temperature ranging from −10° C. to 50° C. and for a time ranging from 30 min to about 5 days.

According to step 1c) and 1d) the reaction is carried out in an organic solvent, preferably DCM or DMF, in the presence of PTSA at a temperature ranging from 20° C. to reflux and for a time ranging from 30 min to about 24 h.

According to step 1e) the coupling reaction is performed in an organic solvent, preferably DCM or CH$_3$CN, in optionally basic conditions, e.g. TEA, DMAP, and optionally in presence of a condensing agent such as DCC or EDCI. The reaction is carried out at a temperature ranging from 0° C. to reflux and for a time ranging from 30 min to about 24 h. Removal of the protecting group is performed using known procedure reported in the literature (see e.g. Protective Groups in Organic Synthesis; Theodora W. Greeen, Peter G. M. Wuts).

According to step 2a), 2b), 3), 5), 6a), 6b) and 7) the reaction is performed in an organic solvent, preferably DCM, THF, DMSO or DMF in optionally basic conditions, e.g. TEA, DMAP and optionally in presence of a condensing agent such as DCC, EDCI and optionally in presence of a triflate salt, preferably, scandium(III) triflate. The reaction is carried out at a temperature ranging from 0° C. to reflux and for a time ranging from 30 min to about 24 h.

According to step 4a) the coupling reaction is performed as reported above under steps 1a) to 1e) depending upon the characteristics of the reagents applied.

According to step 4b) the coupling reaction is performed in an organic solvent, preferably DMSO, DCM, THF, CH$_3$CN or DMF, optionally in presence of a condensing agent, such as for example DCC, EDC and with the optional addition of DMAP (for general coupling reagents see e.g. Amino Acids, Peptides and Proteins in Organic Chemistry: Building Blocks, Catalysis and Coupling Chemistry, Volume 3; Andrew B. Hughes, Ayman El-Faham, Fernando Albericio). The coupling reaction according to step 4b) is preferably carried out at a temperature ranging from 20° C. to reflux, in the optional presence of a base, and for a time ranging from 30 min to about 24 h.

The compound of formula (VI) wherein R7 is hydrogen can be prepared as reported in Chem. Pharm. Bull. 1991, 39(12), 3183-3188; the compound of formula (VI) wherein R7 is an imidazol-1-yl-carbonyl moiety is prepared as reported in the experimental part (see below).

Compounds of formula (VII) are commercially available or can be prepared by methods known to the expert in the art or as reported in WO9202255; J. Med. Chem. 2010, 53(21), 7731-7738; J. Med. Chem., 2012, 55(2), 766-782.

Compounds of formula (VIII), (IX), (X), (XI), (XII), (XIII) and (XIV) are commercially available or can be prepared by methods known to the expert in the art or as reported in Anticancer Agents in Med Chem 2008, (8), 618-637 or in WO2010/009124, EP0624377 or EP2357006.

PHARMACOLOGY

The compounds of the present invention are useful as antitumor agents.

A mammal, e.g. a human or animal, may therefore be treated by a method comprising administering thereto a pharmaceutically effective amount of a compound of formula (I).

The condition of the human or animal may be ameliorated or improved in this way.

The evaluation of the cytotoxicity of the compounds of formula (I) is assessed as described below.

In Vitro Cell Proliferation Assay

A2780 human ovarian and MCF7 human breast cancer cells (1250 cells/well) were seeded in white 384 well-plates in complete medium (RPMI1640 or EMEM plus 10% Fetal bovine serum) and treated with compounds dissolved in 0.1% DMSO, 24 h after seeding. The cells were incubated at 37° C. and 5% $CO_2$ and after 72 h the plates were processed using CellTiter-Glo assay (Promega) following the manufacturers instructions.

CellTiter-Glo is a homogenous method based on the quantification of the ATP present, an indicator of metabolically active cells. ATP is quantified using a system based on luciferase and D-luciferin resulting into light generation. The luminescent signal is proportional to the number of cells present in culture.

Briefly, 25 μL/well of reagent solution are added to each well and after 5 min shaking microplates are read by a luminometer. The luminescent signal is proportional to the number of cells present in culture.

Representative compounds of the invention of formula (I) were tested in the specific in vitro cell proliferation assay described above.

All the tested compounds have an $IC_{50}$ value <100 nM in A2780 human ovarian cancer cells.

In particular, Comp. 1 and 2 have $IC_{50}$ value <10 nM.

| Compound | A2780 ($IC_{50}$ nM) |
|---|---|
| 9-bromo-camptothecin | 1.625 |
| 1 | 0.970 |
| 2 | 1.559 |

As can be appreciated by the skilled person, all these representative compounds are thus particularly advantageous in antitumor therapy.

Furthermore, the functionalized compounds of formula (I) of the present invention are suitable to be conjugated.

The ability of the functionalized derivatives of formula (I) to be conjugated has been assessed by conjugating them with the MCM2 protein.

Solubility Assay: High-Throughput Solubility

Nominal 200 μM compounds suspensions/solutions in aqueous potassium phosphate buffer at pH=7 and aqueous citric acid buffer at pH=3 were prepared on a "Multiscreen-HTS", 0.2 μm filter plate (Millipore, Billerica, Mass.). These solutions were stirred for 10 min and stored for 24 h at room temperature to pre-saturate the membrane filter and to reach a "pseudo-thermodynamic solubility". Then the plate was put on a 500 μL 96 multiwell plate containing 200 μL of $CH_3CN$ in each well and centrifuged at 2000 rpm for 5 min. The so obtained solutions were then analyzed simultaneously by HPLC-UV with standard solutions for quantification.

Example (A)

Preparation of the MCM2 Conjugate 1.5 mg (0.045 μmol) of MCM2 protein (corresponding to residues 10-294 of the full length sequence, see Ishimi et al., 2001 Journal Biological Chemistry, vol. 276, pages 42744-42752) were dissolved in 0.5 mL of phosphate buffered saline solution (pH 7.2), pH value was adjusted to 8.5 by addition of 55 μL of 1M $NaHCO_3$ (pH 8.5) and 0.5 mg of a compound of formula (I), Comp. 8, were added from a 10 mg/mL DMSO solution. The reaction was incubated for 1 h at room temperature then the reaction mixture was desalted on a NAP-10 column conditioned in phosphate buffered saline solution and the fractions containing the protein were collected and pooled.

Reacted MCM2 was characterized by HPLC/ESI mass spectrometry.

A reversed phase HPLC method (Poroshell C3 column 75×2.1 mm, 1100 Agilent HPLC instrument) was coupled with an Agilent 1946 single quadrupole mass spectrometry detector with an orthogonal ESI source.

The unreacted MCM2 protein showed a molecular weight of 33055 Da (FIG. 1).

Figure 2:
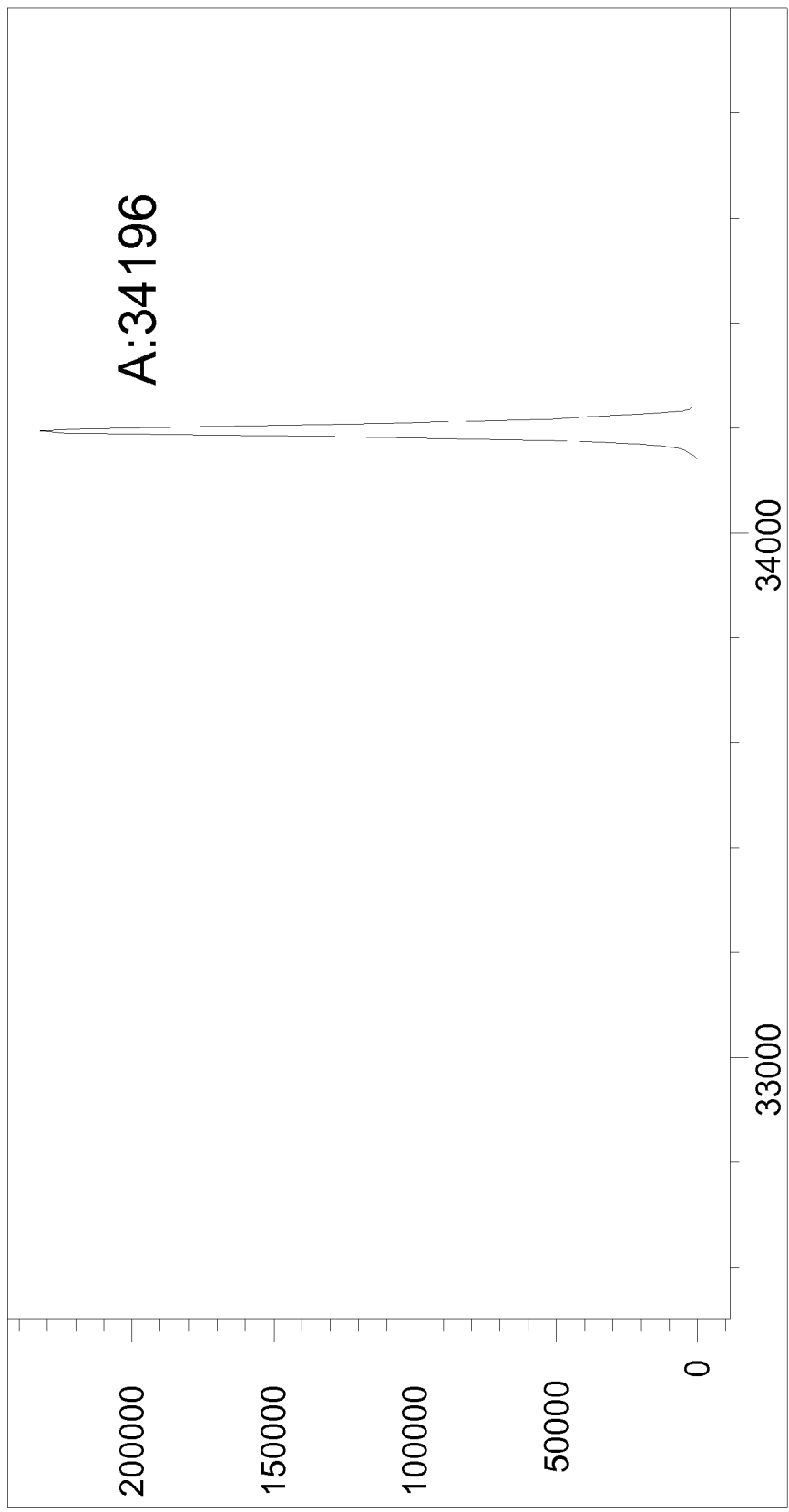
FIG. 2 shows the deconvoluted mass spectrum of MCM2 protein reacted with Comp. 8 and reports the molecular weight (m/z) on the x axis, while intensity expressed as counts per second (cps) is reported on the y axis.

The reacted MCM2 protein showed a molecular weight of 34196 Da (FIG. 2).

The increase of 1139 Da in the molecular weight of the protein is indicative of the addition of a single molecule of Comp. 8 to the single cysteine residue available on the MCM2 protein.

Example (B)

Preparation of the Cysteine Conjugate 2 nmol of cysteine (Cys, MW 121 Da) have been reacted with 2 nmol of a functionalized compound of formula (I), Comp. 17 (MW 1029 Da).

Figure 3:
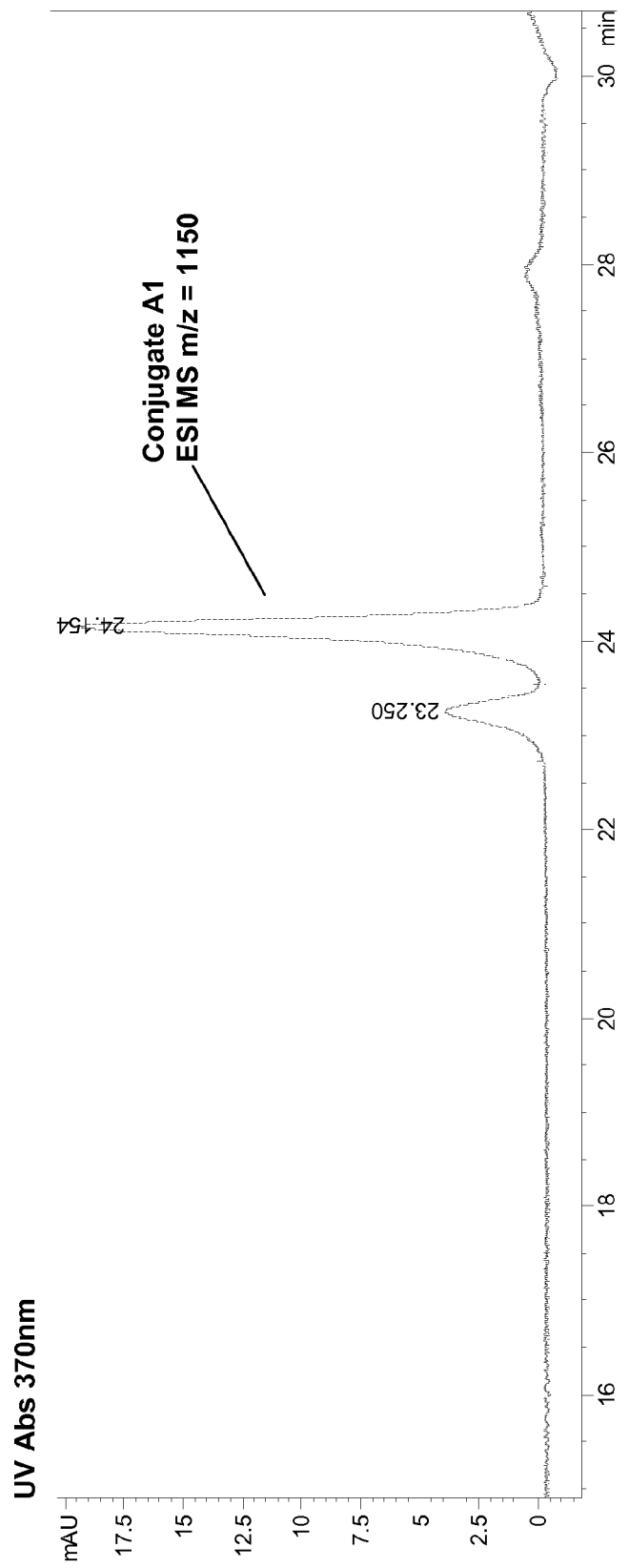
FIG. 3 shows the HPLC profile of the conjugate A1 and reports the time (min) on the x axis while UV absorbance (mAU) is reported on the y axis.
Figure 3A:
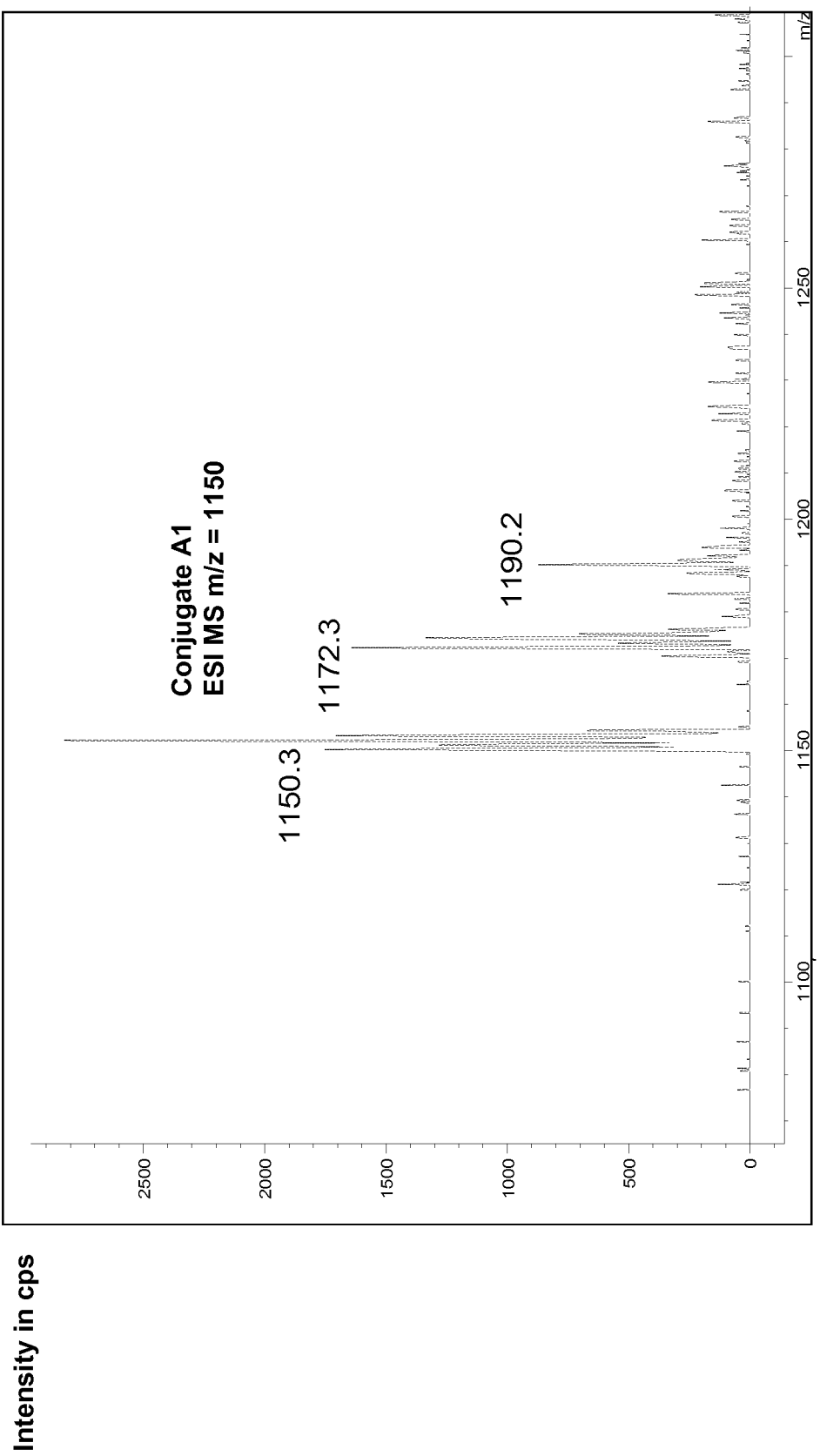
FIG. 3a shows the mass spectrum of the conjugate A1 and reports the molecular weight (m/z) on the x axis while intensity expressed as counts per second (cps) is reported on the y axis.

The reaction was incubated for 1 h at 21° C. in presence of borate buffer 50 mM pH 8, DTPA (diethylene triamine pentaacetic acid) 2 mM, NaCl 50 mM, obtaining conjugate A1 (m/z=1150), and then it was analyzed by HPLC/ESI -MS using a reversed phase HPLC method (PLRP-S column 1000A 8 μM 150×2.1 mm) on a 1100 Agilent HPLC instrument coupled with an Agilent 1946 single quadrupole mass spectrometry detector with an orthogonal ESI source (FIGS. 3 and 3*a*).

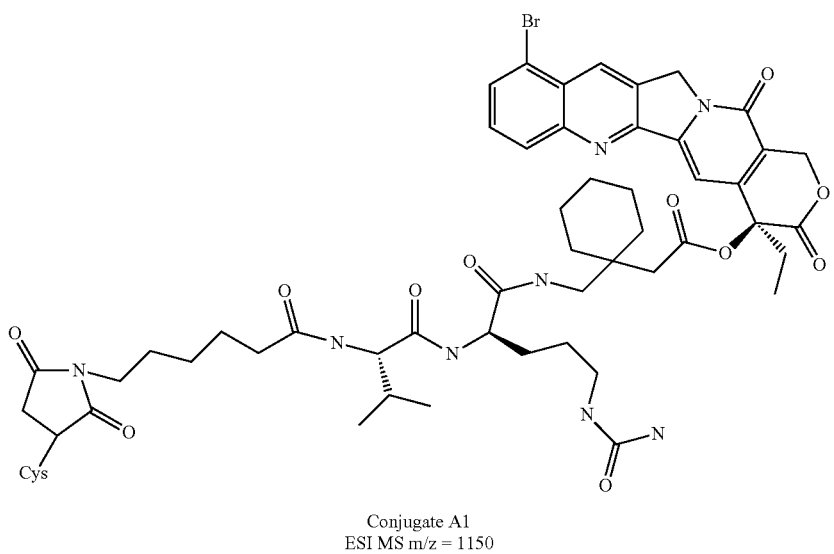

Conjugate A1
ESI MS m/z = 1150

Release of a Drug Moiety from a Conjugate

Example (C)

As an example, that is not intended to limit the scope of the invention, the release of a compound of formula (I) from the conjugate was performed in presence of cathepsin as reported below.

The conjugate A1 was incubated with 0.2 units of cathepsin B in sodium acetate buffer pH 5.5 and 1 mM Cys for 2 h at 40° C. Then pH was adjusted to 7.4 by addition of Tris-HCl buffer and maintained at room temperature for 1 h.

Figure 4:
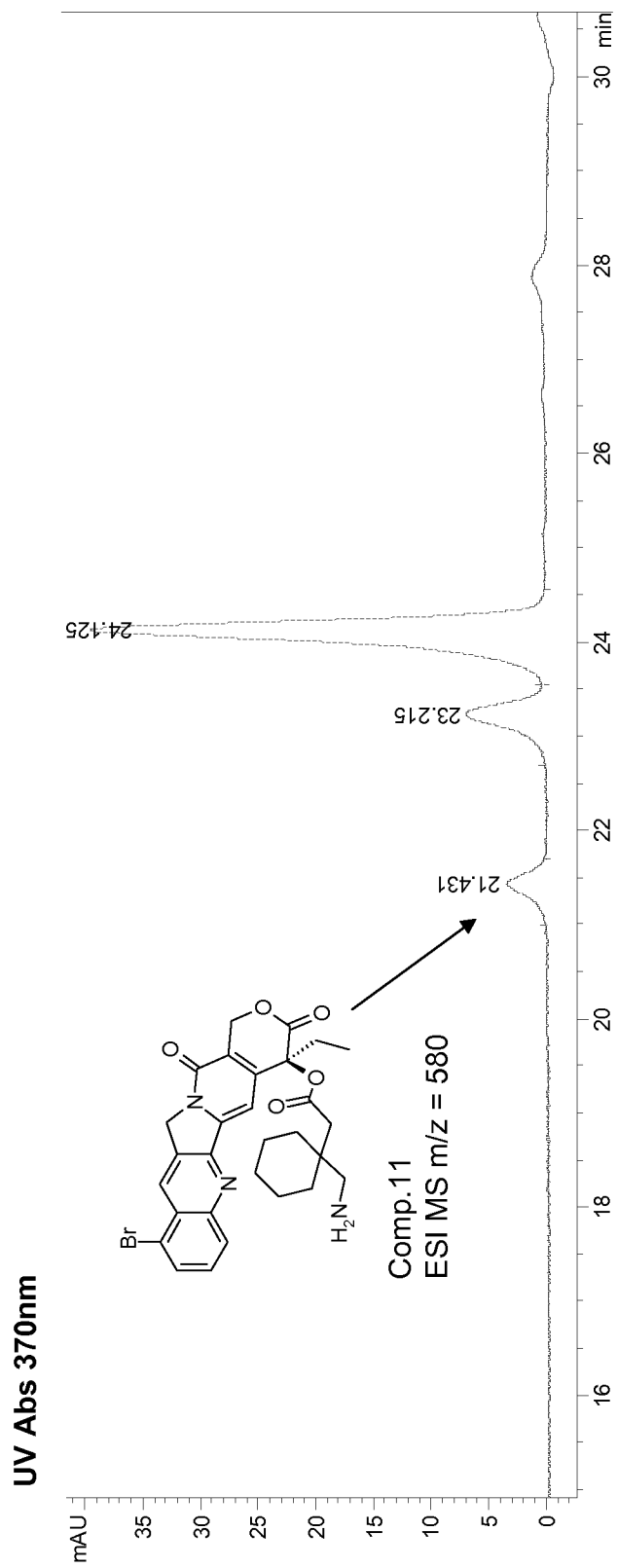
FIG. 4 shows the HPLC profile after 2 h treatment of conjugate A1 with cathepsin and reports the time (min) on the x axis while UV absorbance (mAU) is reported on the y axis.
Figure 5:
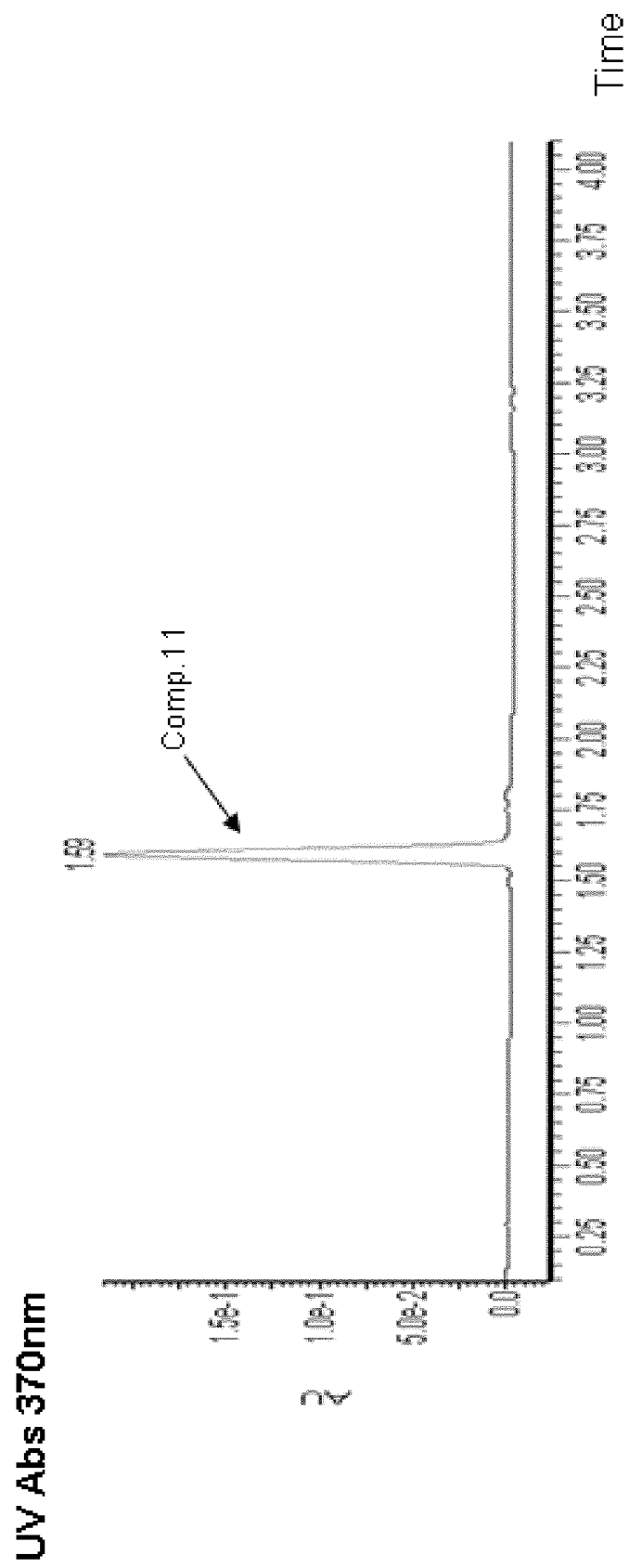
FIG. 5 shows the HPLC profile of Comp. 11 and reports the time (min) on the x axis while UV absorbance (AU) is reported on the y axis.
Figure 5A:
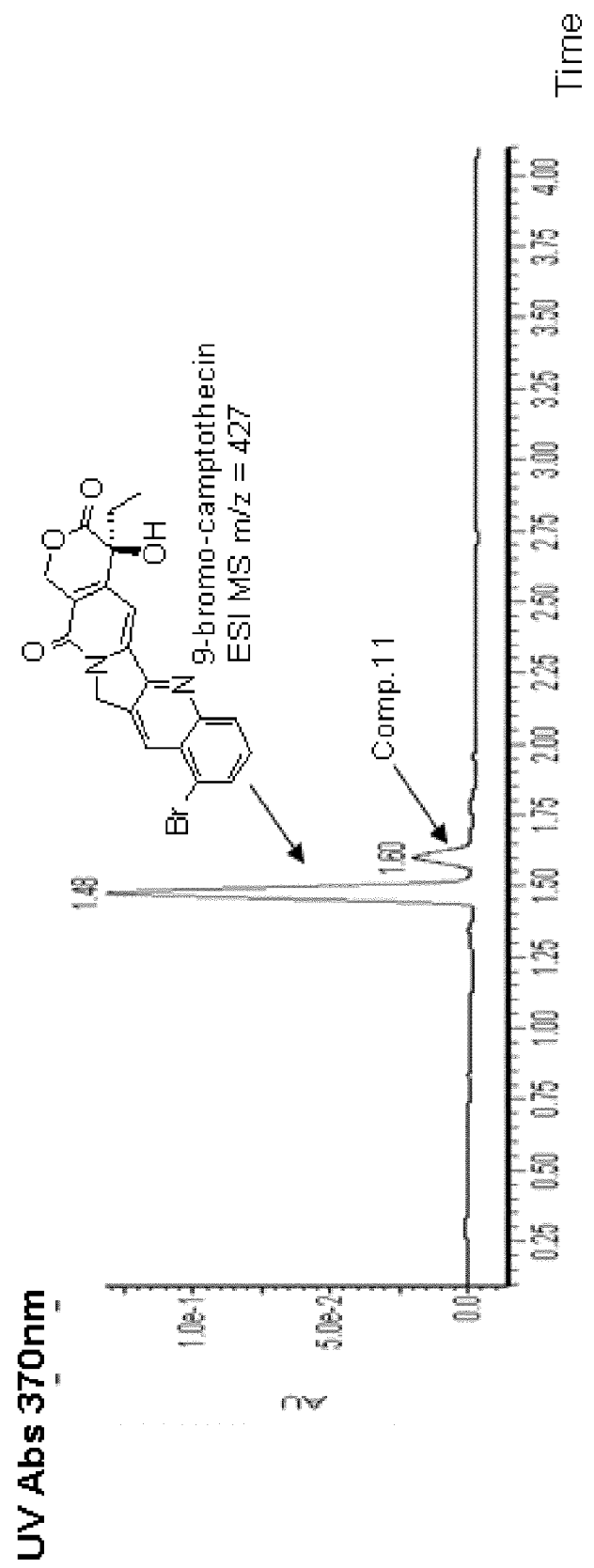
FIG. 5a shows the HPLC profile after 1 h treatment at pH 7.4 of Comp. 11 and reports the time (min) on the x axis while UV absorbance (AU) is reported on the y axis.
Figure 5B:
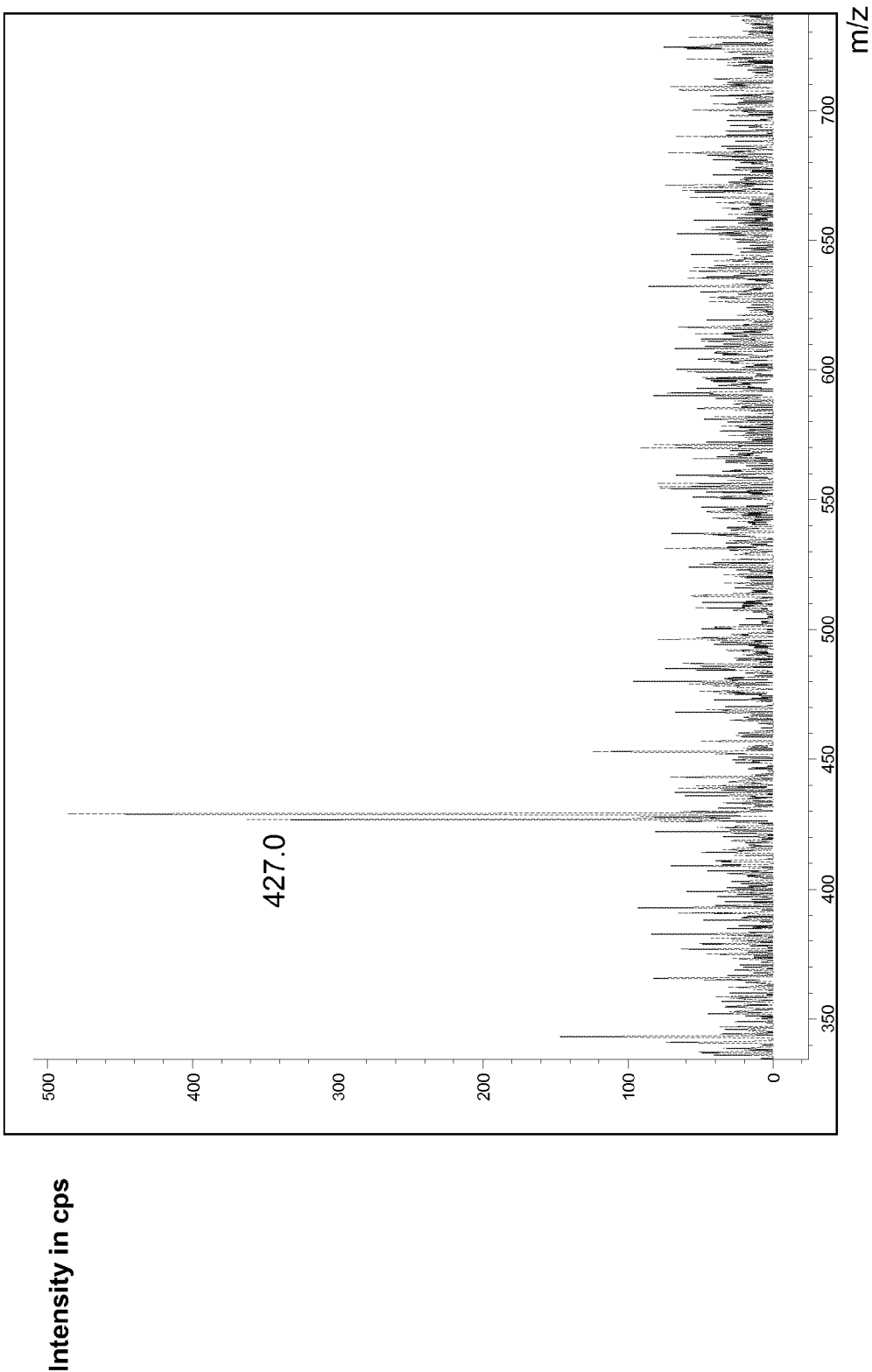
FIG. 5b shows the mass spectrum of the released 9-bromo-camptothecin and reports the molecular weight (m/z) on the x axis while intensity expressed as counts per second (cps) is reported on the y axis.

Partial disappearance of the conjugate A1 and release of the corresponding compound of formula (I), Comp. 11, as well as of 9-bromo-camptothecin, confirms the breaking, first of the Z peptidic linker from the conjugate A1 (FIGS. 4 and 4a), then the elimination of the self-immolative group W (FIGS. 5, 5a and 5b).

The compounds of the present invention can be administered either as single agents or, alternatively, in combination with known anticancer treatments such as radiation therapy or chemotherapy regimen, and/or in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrix metalloproteinase inhibitors, telomerase inhibitors, tyrosine kinase inhibitors, anti-growth factor receptor agents, anti -HER agents, anti-EGFR agents, anti-angiogenesis agents (e.g. angiogenesis inhibitors), farnesyl transferase inhibitors, rasraf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, the weight, the conditions of the patient and the administration route.

For example, a suitable dosage adopted for oral administration of a compound of formula (I) may range from about 1 to about 300 mg per dose, from 1 to 5 times daily. The compounds of the invention can be administered in a variety of dosage forms, e.g., orally, in the form of tablets, capsules, sugar or film coated tablets, liquid solutions or suspensions; rectally in the form of suppositories; parenterally, e.g., subcutaneously, intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose, saccharose, cellulose, corn starch or potato starch; lubricants, e.g., silica, talc, stearic acid, magnesium or calcium stearate, and/or polyethylene glycols; binding agents, e.g., starches, arabic gum, gelatin, methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film -coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusions may contain, as a carrier, sterile water or preferably they may be in the form of sterile, aqueous, isotonic, saline solutions or they may contain propylene glycol as a carrier. The suppositories may contain, together with the active compound, a pharmaceutically acceptable carrier, e.g. cocoa butter, polyethylene glycol, a polyoxyethylene sorbitan fatty acid ester surfactant or lecithin.

With the aim at better illustrating the present invention, without posing any limitation to it, the following examples are now given.

EXAMPLES

The synthetic preparation of some compounds of formula (I) of the invention is described in the following examples.

The compounds of the present invention, as prepared according to the following examples, were also characterized by $^1$H-NMR and/or by Exact Mass data ESI($^+$)

$^1$H-NMR spectra were recorded at 28° C. on a Varian INOVA 400 spectrometer operating at 400.5 MHz, at 25° C. on a Varian INOVA 500 operating at 499.8 MHz and at 28° C. on a Varian INOVA 600 operating at 599.9 MHz. Proton chemical shifts were referenced with respect to the residual solvent signals (DMSO-d$_6$:2.50 ppm; CH$_3$CN-d$_3$:1.96 ppm). Data are reported as follows: chemical shift (δ), multiplicity (s=singlet, d=doublet, t=triplet, q=quartet, br.s. =broad singlet, dd=doublet of doublets, m=multiplet), coupling constants (J, Hz), and number of protons.

ESI($^+$)mass spectra were obtained on a Q-Tof Ultima (Waters, Manchester, UK) directly connected with a 1100 micro-HPLC system (Agilent, Palo Alto, US) as previously described (M. Colombo, F. Riccardi-Sirtori, V. Rizzo, *Rapid Commun. Mass Spectrom.* 2004, 18, 511-517).

In the examples below as well as throughout the application, the following abbreviations have the following meanings. If not defined, the terms have their generally accepted meanings.

| ABBREVIATIONS | |
|---|---|
| DCC | N,N'-dicyclohexylcarbodiimide |
| DBU | 1,8-diazabicyclo[5.4.0]undec-7-ene |
| DCM | dichloromethane |
| DIPEA | N,N-diisopropyethylamine |
| DMAP | N,N-dimethylaminopyridine |
| DMF | N,N-dimethylformamide |
| DMSO | dimethyl sulfoxide |
| EDCI | N-ethyl-N',N'-diisopropyl carbodiimide hydrochloride |
| EDC | 1-ethyl-3-(3-dimethylaminopropyl)carbodiimide |
| Et$_2$O | diethyl ether |
| EtOAc | ethyl acetate |
| EtOH | ethanol |
| HCl | hydrochloric acid |
| HOBt | 1H-benzotriazol-1-ol |
| LiHMDS | lithium bis(trimethylsilyl)amide |
| MeOH | methanol |
| Na$_2$SO$_4$ | sodium sulfate |
| NaHCO$_3$ | sodium hydrogen carbonate |
| NaOH | sodium hydroxide |
| TEA | triethylamine |
| TFA | trifluoroacetic acid |
| THF | tetrahydrofuran |
| mg | milligrams |
| mmol, μmol | millimoles, micromoles |
| M, mM, μM | molar, millimolar, micromolar |

| ABBREVIATIONS | |
|---|---|
| mL, μL | milliliters, microliters |
| μm | micrometers |
| (M)Hz | (mega)herz |
| ppm | parts-per-million |
| h | hour(s) |
| min | minute(s) |

Example 1

Step 1b (4S)-10-bromo-4-ethyl-3,14-dioxo-3,4,12,14-tetrahydro-1H-pyrano[3',4'6,7]indolizino[1,2-b]quinolin-4-yl glycinate hydrochloride (Ia), Comp. 1[L=(IIk); W, Z, RM=null]

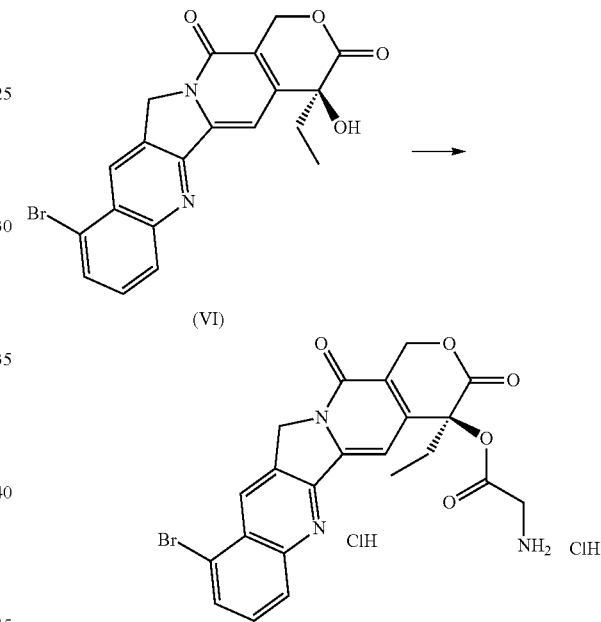

To a solution of 9-bromo-camptothecin (100 mg, 0.234 mmol) in anhydrous DMSO (6 mL), commercially available 4-nitrophenyl [(tert-butoxycarbonyl)amino]acetate (138.5 mg, 0.468 mmol) and DMAP (57 mg, 0.468 mmol) were added. The mixture was stirred at room temperature for 3 days and then additional 2 equivalents of 4-nitrophenyl [(tert-butoxycarbonyl)amino]acetate and DMAP were added. After additional two days, the mixture was diluted with DCM (50 mL), extracted with water (3×20 mL) and washed with brine. The organic layer was dried with Na$_2$SO$_4$, filtered and concentrated under vacuum. The product was purified by flash chromatography (DCM/EtOAc 7/3) to provide the protected intermediate as yellow powder that was dissolved in dioxane (5 mL) and treated with HCl 4 M in dioxane (1 mL). The reaction was stirred at room temperature for 2 h and then the solvent was removed under vacuum. The resulting residue was triturated with Et$_2$O to afford the title product (90 mg, 69%).

ESI MS: m/z 484-486 (MH$^+$)

$^1$H NMR (599.9 MHz, DMSO-d$_6$) δ ppm 0.95 (t, J=7.3 Hz, 3 H), 2.14-2.24 (m, 2 H), 4.06-4.14 (m, 1 H), 4.30-4.38

(m, 1 H), 5.34-5.42 (m, 2 H), 5.54-5.59 (m, 2 H), 7.34 (s, 1 H), 7.81 (dd, J=8.6, 7.5 Hz, 1 H), 8.11 (dd, J=7.5, 0.9 Hz, 1 H), 8.19 (d, J=8.6 Hz, 1 H), 8.37 (br. s., 3 H), 8.93 (s, 1 H).

Example 2

Step 1e (4S)-10-bromo-4-ethyl-3,14-dioxo-3,4,12,14-tetrahydro-1H-pyrano[3',4',7]indolizino[1,2-b]quinolin-4-ylpiperazine-1-carboxylate (Ia), Comp. 3[L=(IIj); W, Z, RM=null]

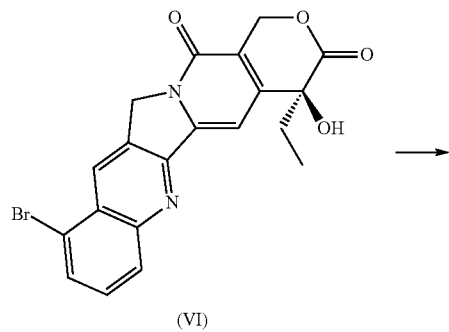

(VI)

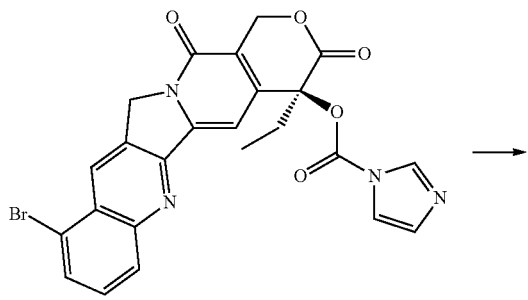

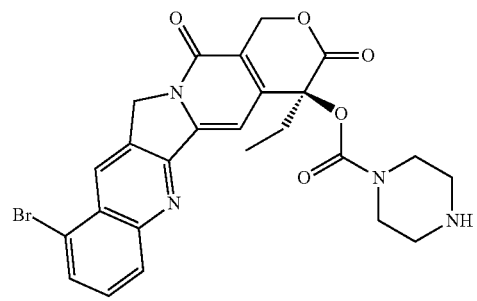

To a solution of 9-bromo-camptothecin (100 mg, 0.234 mmol) in anhydrous THF (10 mL), carbonyldiimidazole (304 mg, 1.87 mmol) was added. The mixture was stirred at 55° C. for 5 h and then was diluted with DCM (50 mL), washed with diluted HCl (2×30 mL) and with brine (2×20 mL). The organic layer was dried with $Na_2SO_4$, filtered and concentrated under vacuum. The product was purified by flash chromatography (EtOAc 100%) to provide the intermediate (4S)-10-bromo-4-ethyl-3,14-dioxo-3,4,12,14-tetrahydro-1H-pyrano[3',4':6,7]indolizino[1,2-b]quinolin-4-yl 1H-imidazole-1-carboxylate (84 mg, 69%).

ESI MS: m/z 521-523 (MH$^+$)

$^1$H NMR (400.5 MHz, DMSO-d$_6$) δ ppm 1.02 (t, J=7.7 Hz, 3 H), 2.29-2.35 (m, 2 H), 5.35 (s, 2 H), 5.52-5.64 (m, 2 H), 7.18 (d, J=1.7 Hz, 1 H), 7.33 (s, 1 H), 7.73 (dd, J=7.3, 8.2 Hz, 1 H), 7.75 (d, J=1.7 Hz, 1 H), 8.05 (dd, J=7.3, 1.7 Hz, 1 H), 8.16 (dd, J=8.2, 1.7 Hz, 1 H), 8.52 (s, 1 H), 8.88 (s, 1 H).

To a solution of intermediate (4S)-10-bromo-4-ethyl-3,14-dioxo-3,4,12,14-tetrahydro-1H -pyrano[3',4':6,7]indolizino[1,2-b]quinolin-4-yl 1H-imidazole-1-carboxylate (30 mg, 0.0575 mmol), piperazine (7.5 mg, 0.0863 mmol) in anhydrous CH$_3$CN (1.5 mL) was added and then stirred at room temperature for 1.5 h until starting material was no longer detected (HPLC-MS analysis). The mixture was diluted with DCM (50 mL), washed with water (2×30 mL) and then with brine (2×20 mL). The organic layer was dried with $Na_2SO_4$, filtered and concentrated under vacuum to yield the title compound.

ESI MS: m/z 539-541 (MH$^+$)

Analogously, the following compound has been prepared:

(4S)-10-bromo-4-ethyl-3,14-dioxo-3,4,12,14-tetrahydro-1H-pyrano[3',4':6,7]indolizino[1,2-b]quinolin-4-yl methyl [2-(methylamino)ethyl]carbamate hydrochloride (Ia), Comp. 7 [L=(IIm); W, Z, RM=null]

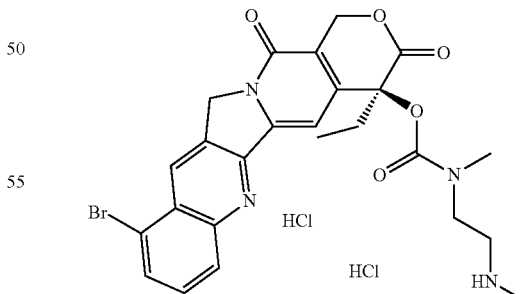

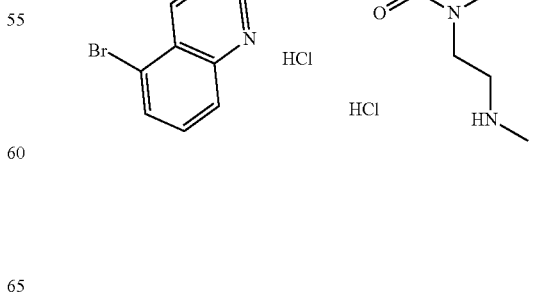

(yield=88%)

ESI MS: m/z 541-543 (MH$^+$)

Example 3

Step 2a

N-[6-(2,5-dioxo-2,5-dihydro-1H-pyrrol-1-yl)hexanoyl]-L-valyl-N-{4-[({[4-({[(4S)-10-bromo-4-ethyl-3,14-dioxo-3,4,12,14-tetrahydro-1H-pyrano[3',4':6,7]indolizino[1,2-b]quinolin-4-yl]oxy}carbonyl)piperazin-1-yl]carbonyl}oxy)methyl]phenyl}-$N^5$-carbamoyl-L-omithinamide (I), Comp. 5 [L=(IIj); W=(IIIc); Z=Citrulline-Valine; RM=(Va)]

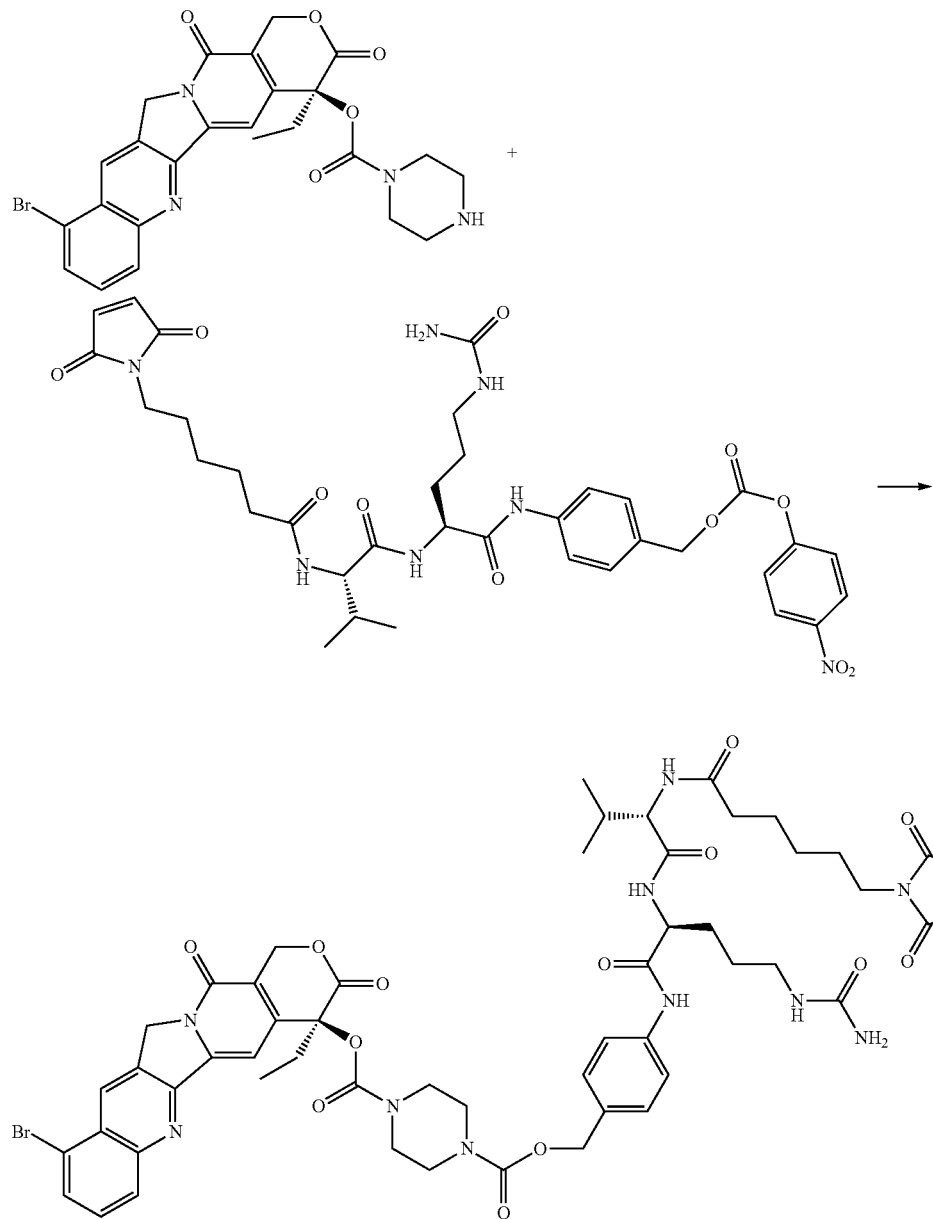

A solution of (4S)-10-bromo-4-ethyl-3,14-dioxo-3,4,12,14-tetrahydro-1H-pyrano[3',4':6,7]indolizino[1,2-b]quinolin-4-yl piperazine-1-carboxylate (Comp. 3) (24.5 mg, 0.0457 mmol) and N-[6-(2,5-dioxo-2,5-dihydro-1H-pyrrol-1-yl)hexanoyl]-L-valyl-$N^5$-carbamoyl-N-[4-({[(4-nitrophenoxy)carbonyl]oxy}methyl)phenyl]-L-omithinamide (MC-Val-Cit -PABC-PNP), prepared as reported in EP0624377A2 and EP2357006A2 (33 mg, 0.0457 mmol), in anhydrous DMSO (1.0 mL) was stirred at room temperature for 2 h until starting material was no longer detected (HPLC-MS analysis). Et$_2$O was added to the mixture and two phases were formed. The upper phase was removed and this sequence was repeated until an amorphous solid was formed on the bottom of the flask. The solid was purified by flash chromatography (EtOAc/ MeOH 90/10) to provide the title compound (1.5 mg, 3%).

ESI MS: m/z 1137-1139 (MH$^+$)

$^1$H NMR (499.8 MHz, DMSO-d$_6$) δ ppm 0.77 -0.88 (m, 6 H), 0.90(2×t, J=7.6 Hz, 3 H), 1.12-1.28 (m, 2 H), 1.30 -1.40 (m, 2 H), 1.89-1.52 (m, 4 H), 1.53-1.75 (m, 2 H), 1.91-2.01 (m, 1 H); 2.06-2.20 (m, 4 H), 2.88-3-06 (m, 2 H), 3.12-3.74 (m partially overlapped by water signal, 10 H), 4.15-4.21 (m, 1 H), 4.32-4.41 (m, 1 H), 5.03 (br. s., 2 H), 5.34 (s, 2 H), 5.41 (br. s., 2 H), 5.40-5.50 (m, 2 H), 5.94-6.02 (br. s., 1 H), 7.00 (s, 2 H), 7.12 (s, 1 H), 7.25-7.36 ((br. s., 2 H), 7.52-7.67 (br. s., 2 H), 7.74-7.84 (m, 2 H), 8.05-8.13 (d, J=6.9 Hz, 1 H), 8.10 (br. s., 1 H), 8.14-8.25 (m, 1 H), 8.90 (s, 1 H), 10.01 (br. s., 1 H).

Analogously, starting from Comp. 7 the following compound has been prepared:

N-[6-(2,5-dioxo-2,5-dihydro-1H-pyrrol-1-yl)hexanoyl]-L-valyl-N-[4-({[{2-[({[(4S)-10-bromo-4-ethyl-3,14-dioxo-3,4,12,14-tetrahydro-1H-pyrano[3',4':6,7]indolizino[1,2-b]quinolin-4-yl]oxy}carbonyl)(methyl)amino]ethyl}(methyl)carbamoyl]oxy}methyl)phenyl]-N5-carbamoyl-L-omithinamide (I), Comp. 8. [L=(IIm); W=(IIIc); Z=Citrullina-Valine; RM=(Va)]

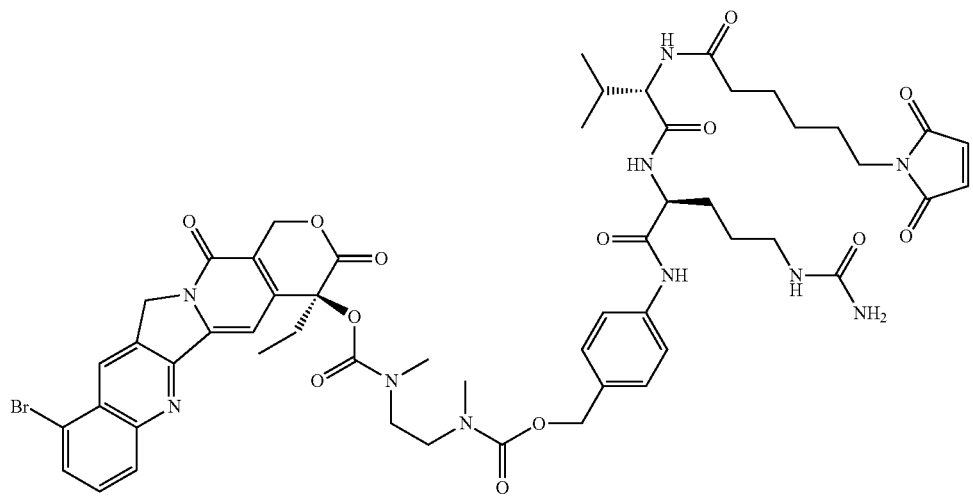 [SMILES: CC[C@@]1(OC(=O)N(C)CCN(C)C(=O)OCc2ccc(NC(=O)[C@H](CCCNC(N)=O)NC(=O)[C@@H](NC(=O)CCCCCN3C(=O)C=CC3=O)C(C)C)cc2)C(=O)OCc2c1cc1n(c2=O)Cc2cc3c(Br)cccc3nc2-1]

ESI MS: m/z 1139-1141 (MH$^+$)

$^1$H NMR (499.8 MHz, DMSO-d$_6$, the spectrum is a mixture of rotational isomers) δ ppm 0.75 -0.87 (m, 6 H), 0.87-0.94 (m, 3H), 1.12-1.22 (m, 2 H), 1.29-1.40 (m, 2 H), 1.40-1.63 (m, 4 H), 1.53-1.73 (m, 2 H), 1.87-2.02 (m, 2 H), 2.04-2.22 (m, 4 H), 2.88-3.05 (m, 2 H), 2.70, 2.72, 2.77, 2.80 (4×s, rotational isomers, 3 H), 2.98, 3.02, 3.09, 3.12 (4×s, rotational isomers, 3 H), 3.24-3.63 (m, partially overlapped by water signal, 6 H), 4.13-4.22 (m, 1 H), 4.28-4.42 (m, 1 H), 4.83, 5.00, 5.09 (3×s, rotational isomers, 2 H), 5.28-5.50 (m, 4 H), 5.41 (br. s., 2 H), 6.00 (br. s., 1 H), 7.00 (s, 1 H), 706-7.11 (m, 1 H), 7.07, 7.21, 7.23, 7.31, 7.40, 7.42, 7.47, 7.54 (8×d, J=8.6 Hz, rotational isomers, 4 H), 7.74-7.84 (m, 2 H), 8.03-8.23 (m, 3 H), 8.84, 8.88, 8.89 (3×s, rotational isomers, 1 H), 9.91, 9.94, 9.996, 9.97 (4×br. s., rotational isomers, 1 H).

Example 4

Step 8b (4S)-10-bromo-4-ethyl-3,14-dioxo-3,4,12,14-tetrahydro-1H-pyrano[3',4':6,7]indolizino[1,2-b]quinolin-4-yl L-phenylalanyl-L-leucylglycinate (I), Comp. 2[L=null; W=null; Z=Glycine-Leucine-Phenylalanine; RM=null]

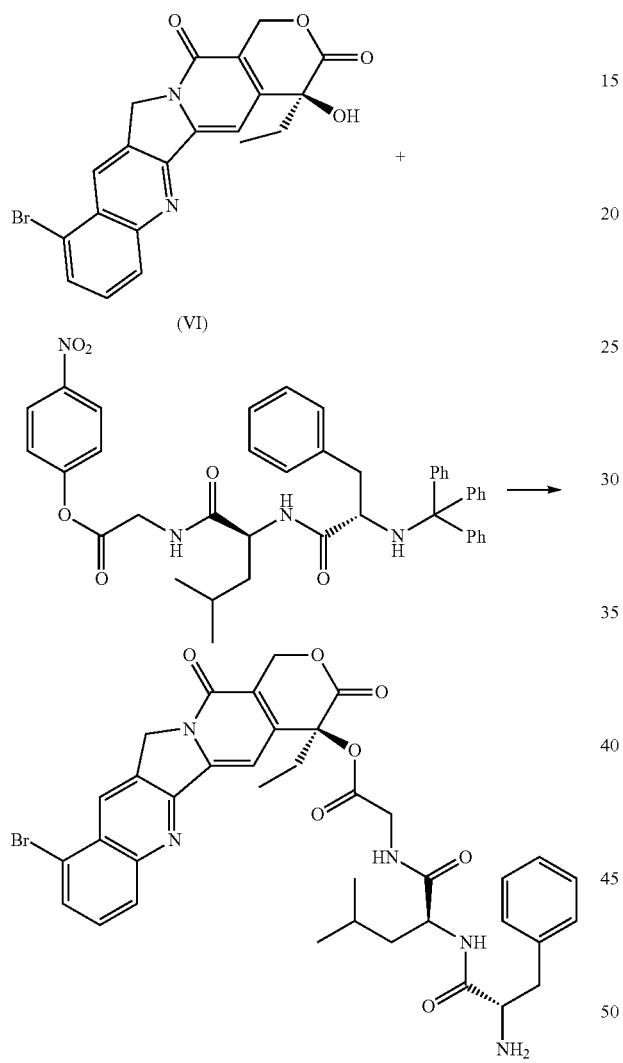

To a solution of 9-bromo-camptothecin (100 mg, 0.234 mmol) in anhydrous DMSO (10 mL), 4-nitrophenyl N-trityl-L-phenylalanyl-L-leucylglycinate (326.6 mg, 0.468 mmol) and DMAP (57 mg, 0.468 mmol) were added. The mixture was stirred at room temperature for 1 day and then two additional equivalent of 4-nitrophenyl N-trityl-L-phenylalanyl-L-leucylglycinate and DMAP were added. After additional two days, the mixture was diluted with DCM, (20 mL) extracted with water (3×10 mL) and washed with brine. The organic layer was dried with $Na_2SO_4$, filtered and concentrated under vacuum. The product was purified by flash chromatography (DCM/EtOAc 7/3) to provide a brown solid protected intermediate. The intermediate was dissolved in a mixture of acetic acid-water (75-25, 10 mL) and the reaction was stirred at room temperature for 1 h. The solvent was removed under vacuum and the crude product was dissolved in DCM (20 mL), washed with a satured solution of $NaHCO_3$ (2×20 mL), water and brine. The resulting residue was purified by flash chromatography (DCM/MeOH from 99/1 to 97/3) to provide the title compound (110 mg, 63%). ESI MS: m/z 744-746 (MH$^+$)

$^1$H NMR (499.8 MHz, DMSO-$d_6$) δ ppm 0.81 (d, J=6.1 Hz, 6 H), 0.92 (t, J=7.4 Hz, 3 H), 1.42-1.48 (m, 2 H), 1.49-1.55 (m, 1 H), 1.68 (br. s., 2 H), 2.08-2.18 (m, 2 H), 2.57 (dd, J=13.3, 8.2 Hz, 1 H), 2.87 (dd, J=13.3, 4.5 Hz, 1 H), 3.38 (dd, J=8.2, 4.5 Hz, 1 H), 3.98-4.20 (m, 2 H), 4.33-4.41 (m, 1 H), 5.32 (s, 2 H), 5.51 (s, 2 H), 7.11-7.24 (m, 6 H), 7.77 (dd, J=8.4, 7.6 Hz, 1 H), 7.96 (d, J=8.7 Hz, 1 H), 8.09 (d, J=7.4 Hz, 1 H), 8.19 (d, J=8.6 Hz, 1 H), 8.50 (t, J=5.9 Hz, 1 H), 8.88 (s, 1 H).

Example 5

(4S)-10-bronno-4-ethyl-3,14-dioxo-3,4,12,14-tetrahydro-1H-pyrano[3',4':6,7]indolizino[1,2-b]quinolin-4-yl N-[6-(2,5-dioxo-2,5-dihydro-1H-pyrrol-1-yl)hexanoyl]-L-phenylalanyl-L-leucylglycinate (I), Comp. 4[L=null; W=null; Z=Glycine-Leucine-Phenylalanine; RM=(Va)]

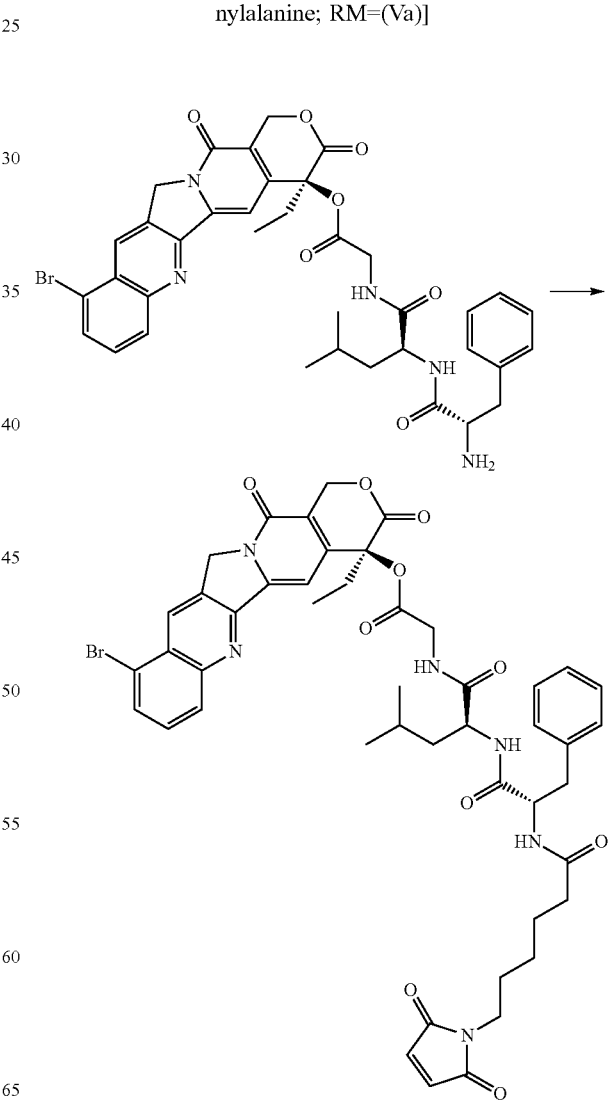

A solution of ((4S)-10-bromo-4-ethyl-3,14-dioxo-3,4,12,14-tetrahydro-1H-pyrano[3',4':6,7]indolizino[1,2-b]quinolin-4-yl L-phenylalanyl-L-leucylglycinate (Comp. 2) (50 mg, 0.0671 mmol) and N-ε-Maleimidocaproyl oxysuccinimide ester (prepared as reported in Helvetica chimica Acta, 1975, 58, 2, 531-541) (31 mg, 0.101 mmol) in a mixture of DCM/CH$_3$CN (1/1 2 mL) was stirred at room temperature for 15 h until starting material was no longer detected (HPLC-MS analysis). The mixture was diluted with DCM (50 mL), washed with water (2×20 mL) and then with brine (2×20 mL). The organic layer was dried with Na$_2$SO4, filtered and concentrated under vacuum. The product was purified by lash chromatography (DCM/MeOH 97/3) to provide the title compound (34 mg 55%). ESI MS: m/z 937-939 (MH$^+$)

$^1$H NMR (499.8 MHz, CH$_3$CN-d$_3$)) δ ppm 0.81 (d, J=5.9 Hz, 3 H), 0.83 (d, J=5.9 Hz, 3 H), 0.98 (t, J=7.4 Hz, 3 H), 1.07-1.15 (m, 1 H), 1.38-1.48 (m, 4 H), 1.50-1.59 (m, 3 H), 2.02 (t, J=7.6 Hz, 2 H), 2.09-2.25 (m, 2 H), 2.71 (dd, J=14.0, 8.2 Hz, 1 H), 2.87 (dd, J=14.0, 5.6 Hz, 1 H), 3.36 (t, J=7.2 Hz, 2 H), 3.97 (dd, J=17.9, 5.9 Hz, 1 H), 4.13 (dd, J=17.9, 6.3 Hz, 1 H), 4.29-4.35 (m, 1 H), 4.39-4.45 (m, 1 H), 5.09-5.21 (m, 2 H), 5.37 (d, J=17.0 Hz, 1 H), 5.57 (d, J=17.0 Hz, 1 H), 6.50 (d, J=7.4 Hz, 1 H), 6.71 (s, 2 H), 6.80 (d, J=8.2 Hz, 1 H), 6.99 (t, J=6.0 Hz, 1 H), 7.02-7.06 (m, 2 H), 7.14-7.20 (m, 3 H), 7.21 (s, 1 H), 7.71 (dd, J=8.5, 7.4 Hz, 1 H), 7.99 (d, J=7.4 Hz, 1 H), 8.16 (d, J=8.5 Hz, 1 H), 8.80 (s, 1 H).

Analogously, starting from compound 3 the following compound has been prepared:

(4S)-10-bromo-4-ethyl-3,14-dioxo-3,4,12,14-tetrahydro-1H-pyrano[3',4':6,7]indolizino[1,2-b]quinolin-4-yl 4-[6-(2,5-dioxo-2,5-dihydro-1H-pyrrol-1-yl)hexanoyl]piperazine-1-carboxylate (I), Comp. 6 [L=(IIj); W=null; Z=null; RM=(Va)]

Example 6

Step 5, DEPROTECTION STEP 6b, DEPROTECTION, STEP 7

Step 5

(4S)-10-bromo-4-ethyl-3,14-dioxo-3,4,12,14-tetrahydro-1H-pyrano[3',4':6,7]indolizino[1,2-b]quinolin-4-yl 4-[(tert butoxycarbonyl)amino]-3,3-dimethylbutanoate

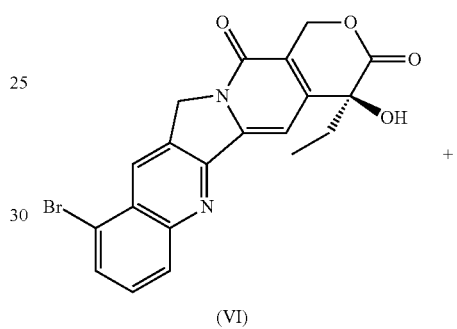

(VI)

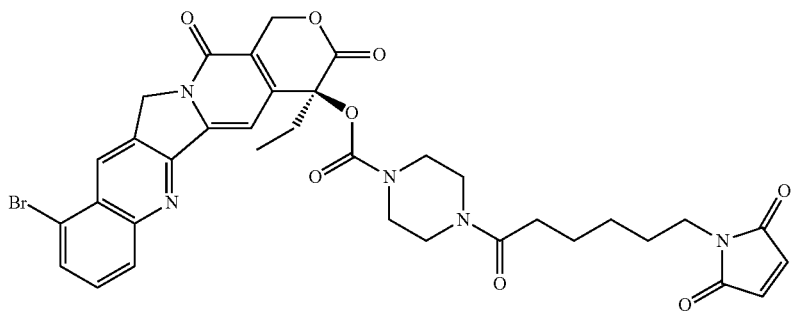 [SMILES: CC[C@@]1(OC(=O)N2CCN(C(=O)CCCCCN3C(=O)C=CC3=O)CC2)C(=O)OCc2c1cc1n(c2=O)Cc2cc3c(Br)cccc3nc2-1]

ESI MS: m/z 732-734 (M$^+$)

$^1$H NMR (499.8 MHz, CH$_3$CN-d$_3$)) δ ppm 0.97 (t, J=7.6 Hz, 3 H), 1.20-1.34 (m, 2 H), 1.47-1.60 (m, 4 H), 2.10-2.22 (m, 2 H), 2.22-2.38 (m, 2 H), 3.16-3.74 (m, 10 H), 5.21-5.30 (m, 2 H), 5.37 (d, J=17 Hz, 1 H), 5.52 (d, J=17 Hz, 1 H), 6.68-6.76 (m, 2 H), 7.14 (s, 1 H), 7.72 (dd, J=8.5, 7.4 Hz, 1 H), 7.98 (d, J=7.4 Hz, 1 H), 8.14 (d, J=8.5 Hz, 1 H), 8.85 (s, 1 H).

-continued

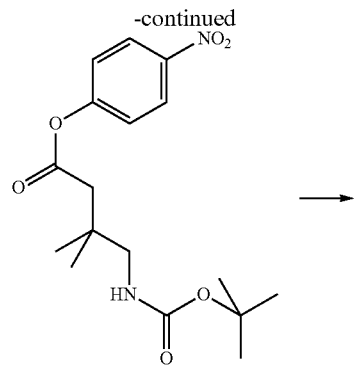

-continued

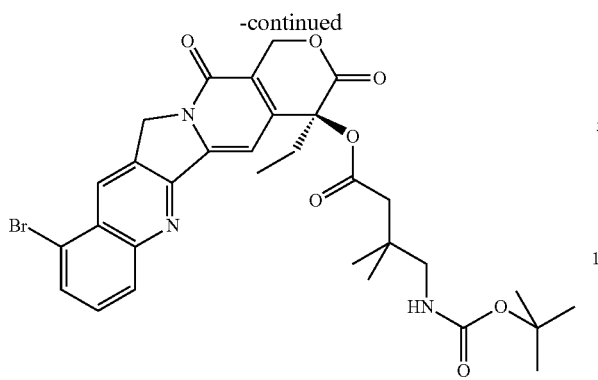

To a solution of 9-bromo-camptothecin (28 mg, 0.066 mmol) in anhydrous DMSO (0.5 mL), 4-nitrophenyl 4-[(tert -butoxycarbonyl)amino]-3,3-dimethylbutanoate (35 mg, 0.1 mmol) and DMAP (16 mg, 0.13 mmol) were added. The mixture was stirred at room temperature for 1 day and then 1.5 additional equivalents of 4-nitrophenyl 4-[(tert butoxycarbonyl)amino]-3,3-dimethylbutanoate and DMAP were added. Additional 2 equivalents of DMAP were added after 3 days and 6 days. The mixture was diluted with DCM, (20 mL), extracted with water (3×10 mL) and washed with brine. The organic layer was dried with $Na_2SO_4$, filtered and concentrated under vacuum. The product was purified by flash chromatography (DCM/acetone 95/5) to provide the title compound (10 mg, 24%).

ESI MS: m/z 640-642 (MH+)

$^1$H NMR (499.8 MHz, DMSO-$d_6$) δ ppm 0.91 (s, 3 H) 0.92 (t, J=7.4 Hz, 3 H) 0.97 (s, 3 H) 1.33-1.41 (m, 9 H) 2.11-2.19 (m, 2 H) 2.26 (d, J=13.8 Hz, 1 H) 2.47 (d, J=13.8 Hz, 1 H) 2.87-2.93 (m, 2 H) 5.30-5.40 (m, 2 H) 5.45- 5.54 (m, 2 H) 6.89 (t, J=6.2 Hz, 1 H) 7.12 (s, 1 H) 7.77-7.83 (m, 1 H) 8.09 (d, J=7.2 Hz, 1 H) 8.20 (d, J=8.4 Hz, 1 H) 8.90 (s, 1 H).

Analogously, starting from 4-nitrophenyl 5-[(tert-butoxycarbonyl)amino]-4,4-difluoropentanoate (prepared as reported in WO03/014069) the following compound has been prepared:

(4S)-10-bromo-4-ethyl-3,14-dioxo-3,4,12,14-tetrahydro-1H-pyrano[3',4':6,7]indolizino[1,2-b]quinolin-4-yl 5-[(tert -butoxycarbonyl)amino]-4,4-difluoropentanoate

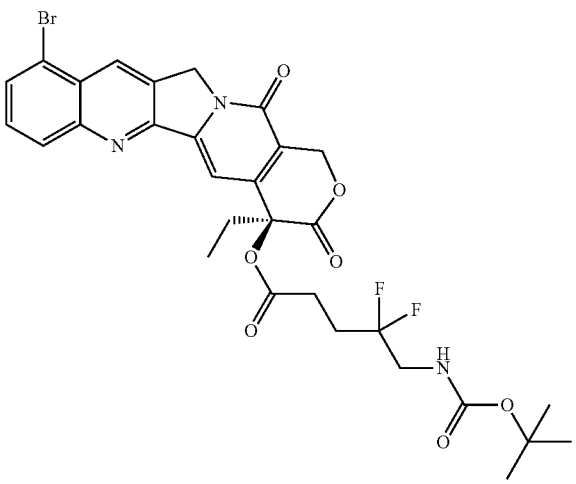 [SMILES: CC[C@@]1(OC(=O)CCC(F)(F)CNC(=O)OC(C)(C)C)C(=O)OCc2c1cc1n(c2=O)Cc2cc3c(Br)cccc3nc2-1]

ESI MS: m/z 662-664 (MH+)

$^1$H NMR (499.7 MHz, $CD_3CN$) δ ppm 0.97 (t, J=7.4 Hz, 3 H) 1.32 (m, 9 H) 2.07-2.32 (m, 4 H) 2.65-2.83 (m, 2 H) 3.43-3.52 (m, 2 H) 5.21-5.29 (m, 2 H) 5.39 (d, J=17.0 Hz, 1 H) 5.56 (d, J=17.0 Hz, 1 H) 5.83 (br. s., 1 H) 7.14 (s, 1 H) 7.70-7.76 (m, 1 H) 8.00 (d, J=7.4 Hz, 1 H) 8.16 (d, J=8.5 Hz, 1 H) 8.86 (s, 1 H).

(4S)-10-bromo-4-ethyl-3,14-dioxo-3,4,12,14-tetrahydro-1H-pyrano[3',4':6,7]indolizino[1,2-b]quinolin-4-yl(1-{[(tert butoxycarbonyl)amino]methyl}cyclohexyl)acetate

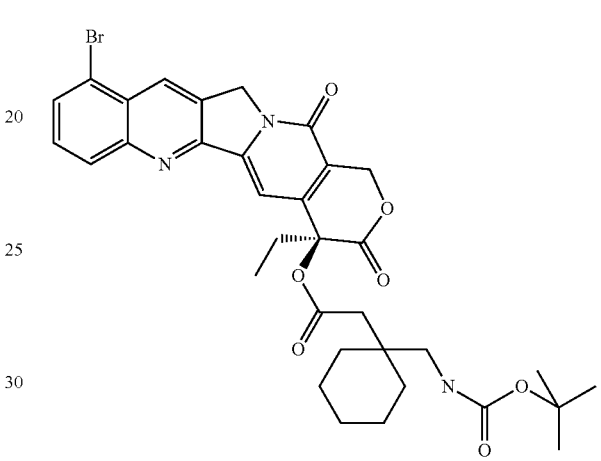

A suspension of 9-bromo-camptothecin (10 mg, 0.023 mmol), scandium triflate (6.8 mg, 0.138 mmol) and DMAP (8.5 mg, 0.07 mmol) in anhydrous DCM (8 mL) was cooled to 0° C., followed by the addition of 4-nitrophenyl (1-{[(tert-butoxycarbonyl)amino]methyl}cyclohexyl)acetate (27 mg, 0.070 mmol). The reaction mixture was stirred at 0° C. for 30 min and at room temperature for 36 h, then it was filtered and the filtrate was washed with 10 mL of 0.1 N hydrochloric acid, 10 mL of 0.1 M $NaHCO_3$, 20 mL of distilled water and then dried over anhydrous $Na_2SO_4$. The organic solvent was removed under reduced pressure and the residue purified by flash chromatography on silica gel (eluent: DCM: acetone (95:5 v/v) to give the title compound (9 mg) (TLC on kieselgel plate, eluent: DCM:acetone (95:5 v/v). Rf=0.25)

ESI MS: m/z 680-682 (MH+)

$^1$H NMR (499.7 MHz, DMSO-$d_6$) δ ppm 0.92 (t, J=7.4 Hz, 3 H) 1.20-1.51 (m, 10 H) 1.37 (s, 9 H) 2.07-2.21 (m, 2 H) 2.36 (d, J=13.8 Hz, 1 H) 2.56 (d, J=13.8 Hz, 1 H) 3.09 (d, J=6.0 Hz, 2 H) 5.31-5.40 (m, 2 H) 5.46-5.53 (m, 2 H) 6.70 (t, J=6.0 Hz, 1 H) 7.18 (s, 1 H) 7.79-7.82 (m, 1 H) 8.09 (d, J=7.4 Hz, 1 H) 8.18 (d, J=8.5 Hz, 1 H) 8.90 (s, 1 H).

Deprotection (4S)-10-bromo-4-ethyl-3,14-dioxo-3,4,12,14-tetrahydro-1H-pyrano[3',4':6,7]indolizino[1,2-b]quinolin-4-yl 4-amino-3,3-dimethylbutanoate hydrochloride (Ic), Comp. 9 [L=null; W=(IIIa); Z=null; RM=null]

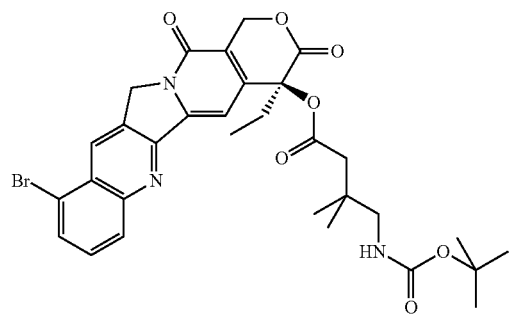

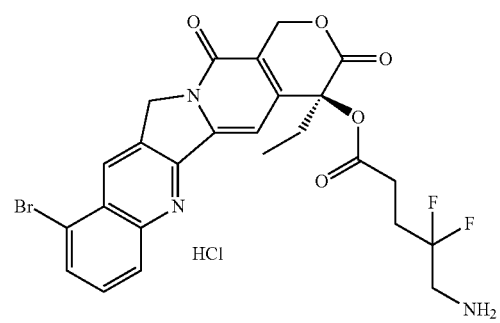

ESI MS: m/z 562-564 (MH⁺)

¹H NMR (499.7 MHz, DMSO-d₆) δ ppm 0.93 (t, J=7.4 Hz, 3 H) 2.13-2.21 (m, 2 H) 2.26-2.38 (m, 2 H) 2.72-2.94 (m, 2 H) 3.41-3.52 (m, 2 H) 5.32-5.41 (m, 2 H) 5.48-5.55 (m, 2 H) 7.18 (s, 1 H) 7.78-7.84 (m, 1 H) 8.10 (d, J=7.4 Hz, 1 H) 8.22 (d, J=8.4 Hz, 1 H) 8.38 (br. s., 3 H) 8.91 (s, 1 H).

4S)-10-bromo-4-ethyl-3,14-dioxo-3,4,12,14-tetrahydro-1H-pyrano[3',4':6,7]indolizino[1,2-b]quinolin-4-yl [1-(aminomethyl)cyclohexyl]acetate hydrochloride (Ic), Comp. 11 [L=null; W=(IIIa); Z=null; RM=null]

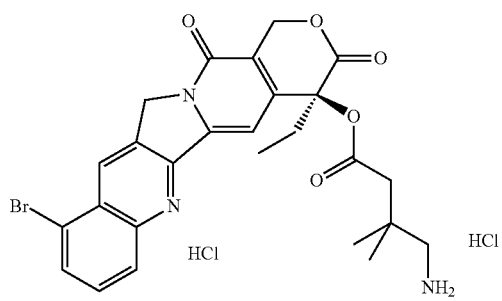

(4S)-10-bromo-4-ethyl-3,14-dioxo-3,4,12,14-tetrahydro-1H-pyrano[3',4':6,7]indolizino[1,2-b]quinolin-4-yl 4-[(tert-butoxycarbonyl)amino]-3,3-dimethylbutanoate (10 mg, 0.016 mmol) was dissolved in 4N HCl in dioxane (0.5 mL) and the reaction was stirred at room temperature for 30 min. The solvents was removed under vacuum and the resulting residue was purified by flash chromatography (DCM/MeOH from 97/3 to 93/7) to provide the title compound (1.9 mg, 19%).

ESI MS: m/z 540-542 (MH⁺)

¹H NMR (499.8 MHz, DMSO-d₆) δ ppm 0.93 (t, J=7.4 Hz, 3 H) 1.00 (s, 3 H) 1.02 (s, 3 H) 2.12-2.20 (m, 2 H) 2.43 (d, J=14.0 Hz, 1 H) 2.60 (d, J=14.0 Hz, 1 H) 2.58-2.71 (m, 2 H) 3.32 (m overlapped by water signal, 2 H) 5.30-5.40 (m, 2 H) 5.47-5.55 (m, 2 H) 7.12 (s, 1 H) 7.76-7.84 (m, 1 H) 8.10 (d, J=7.7 Hz, 1 H) 8.20 (d, J=8.4 Hz, 1 H) 8.23 (br. s., 3 H) 8.91 (s, 1 H).

Analogously, the following compounds have been prepared:

(4S)-10-bromo-4-ethyl-3,14-dioxo-3,4,12,14-tetrahydro-1H-pyrano[3',4':6,7]indolizino[1,2-b]quinolin-4-yl 5-amino-4,4-difluoropentanoate hydrochloride (Ic), Comp. 10 [L=null; W=(IIIa); Z=null; RM=null]

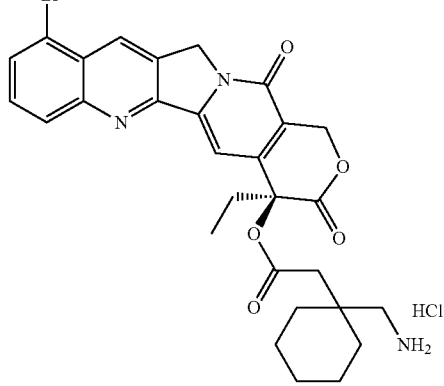

ESI MS: m/z 580-582 (MH⁺)

¹H NMR (500 MHz, DMSO-d₆) δ ppm 0.94 (t, J=7.4 Hz, 3 H) 1.25-1.66 (m, 10 H) 2.09-2.20 (m, 2 H) 2.60 (d, J=14.0 Hz, 1 H) 2.77-2.97 (m, 3 H) 5.32-5.41 (m, 2 H) 5.47-5.55 (m, 2 H) 7.16 (s, 1 H) 7.79-7.83 (m, 1 H) 8.10 (d, J=7.4 Hz, 1 H) 8.14 (br.s., 3 H) 8.18 (d, J=8.5 Hz, 1 H) 8.92 (s, 1 H).

Step 6b
N-(tert-butoxycarbonyl)-L-valyl-N-[4-(({[(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)carbamoyl]oxy}methyl)phenyl]-N⁵-carbamoyl-L-ornithinamide.
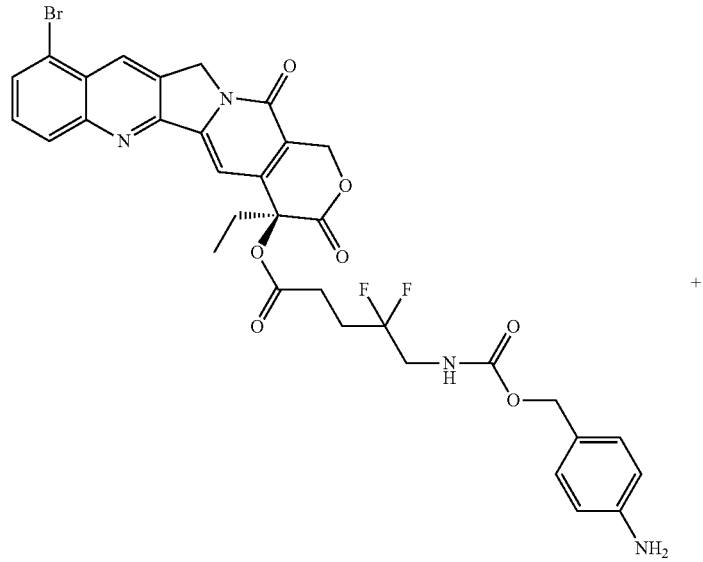
+
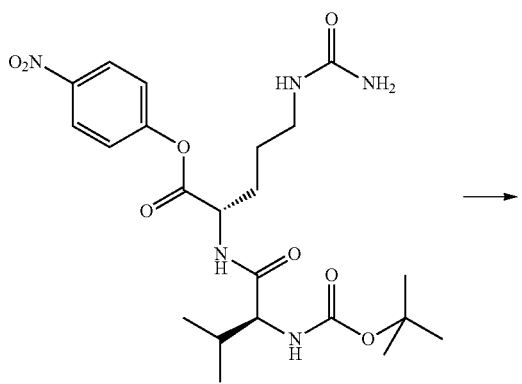

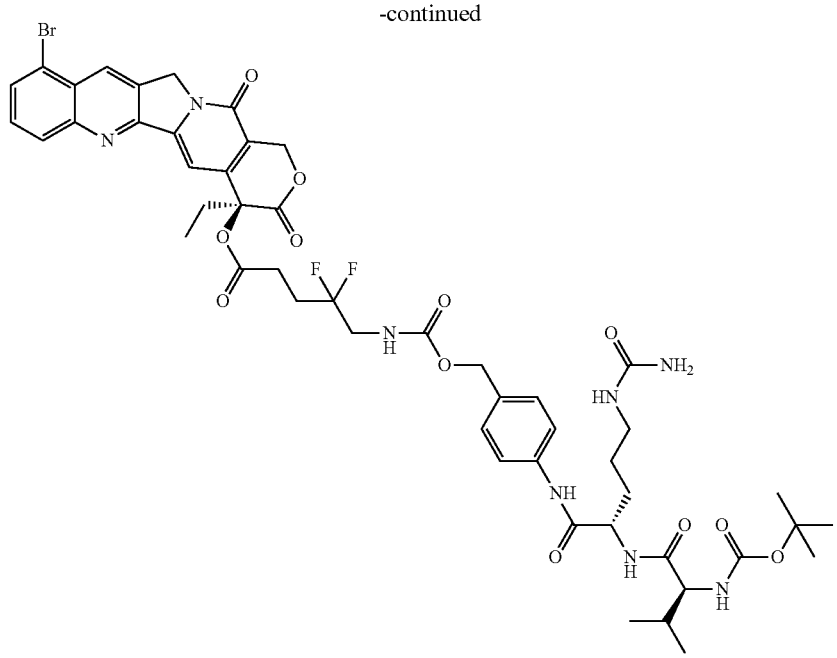

N-(tert-butoxycarbonyl)-L-valyl-N⁵-carbamoyl-N-[4-({[(4-nitrophenoxy)carbonyl]oxy}methyl)phenyl]-L-omithinamide (prepared as reported in WO2005/112919) (8.3 mg, 0.0128 mmol) and (4S)-10-bromo-4-ethyl-3,14-dioxo-3,4,12,14-tetrahydro-1H-pyrano[3',4':6,7]indolizino[1,2-b]quinolin-4-yl 5-amino-4,4-difluoropentanoate hydrochloride (7 mg, 0.0117 mmol) were dissolved in DMF (0.15 mL) and anhydrous DCM (1 mL) and DMAP (3.3 mg, 0.0269 mmol) was added. The reaction mixture was stirred at room temperature for one day in argon atmosphere, then poured into water, aqueous acetic acid and DCM. The organic phase was separated and washed with water. The organic solvent was removed under reduced pressure and the residue was purified by flash chromatography on silica gel (eluent: DCM:MeOH (95:5 v/v) to give the title compound (TLC on kieselgel plate, eluting system DCM:MeOH (9:1 v/v) Rf=0.25)

ESI MS: m/z 1067-1069 (MH⁺)

Analogously, the following compounds can be prepared:

N-(tert-butoxycarbonyl)-L-valyl-N-[4-({[(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)carbamoyl]oxy}methyl)phenyl]-N⁵-carbamoyl-L-omithinamide

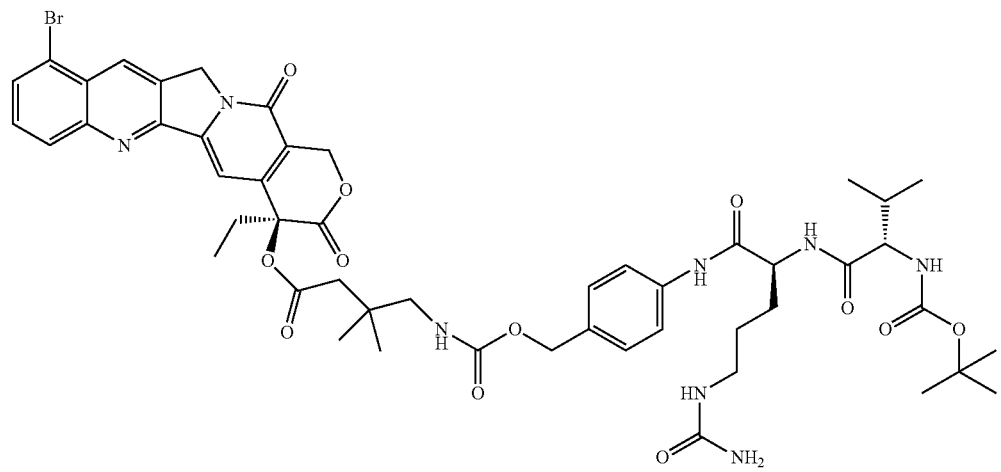 [SMILES: CC[C@@]1(OC(=O)CC(C)(C)CNC(=O)OCc2ccc(NC(=O)[C@H](CCCNC(N)=O)NC(=O)[C@@H](NC(=O)OC(C)(C)C)C(C)C)cc2)C(=O)OCc2c1cc1n(c2=O)Cc2cc3c(Br)cccc3nc2-1]

ESI MS: m/z 1045-1047 (MH⁺)

N-(tert-butoxycarbonyl)-L-valyl-N-(4-{[({1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}carbamoyl)oxy]methyl}phenyl)-N⁵-carbamoyl-L-omithinamide

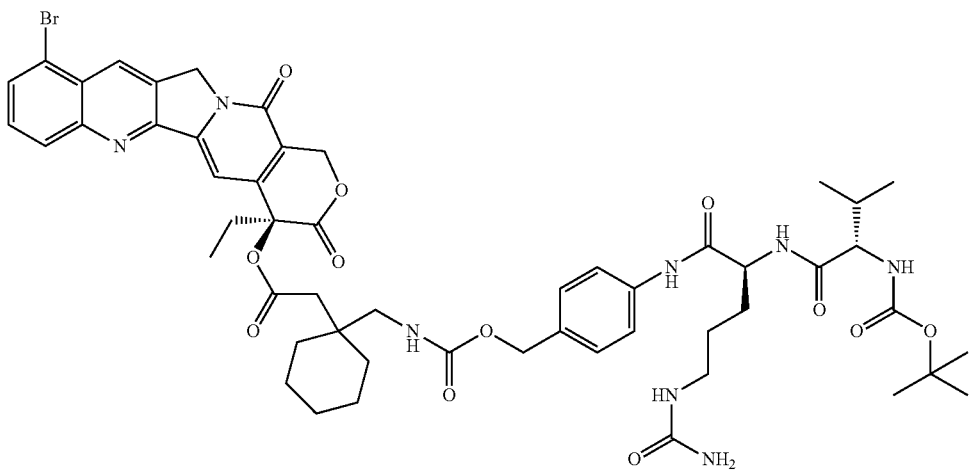 [SMILES: CC[C@@]1(OC(=O)CC2(CNC(=O)OCc3ccc(NC(=O)[C@H](CCCNC(N)=O)NC(=O)[C@@H](NC(=O)OC(C)(C)C)C(C)C)cc3)CCCCC2)C(=O)OCc2c1cc1n(c2=O)Cc2cc3c(Br)cccc3nc2-1]

ESI MS: m/z 1085-1087 (MH+)

N-(tert-butoxycarbonyl)-L-valyl-N-{[1-(2-{[(4S)-10-bromo-4-ethyl-3,14-dioxo-3,4,12,14-tetrahydro-1H -pyrano[3',4':6,7]indolizino[1,2-b]quinolin-4-yl]oxy}-2-oxoethyl)cyclohexyl]methyl}-N⁵-carbamoyl-L-ornithinamide

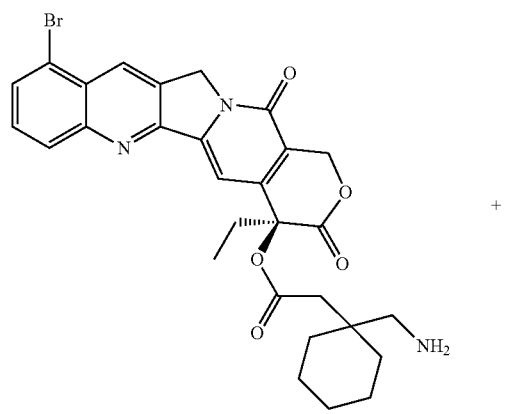

+

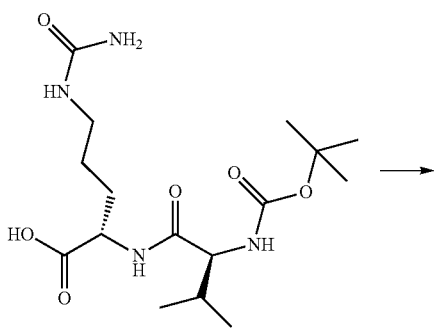

→

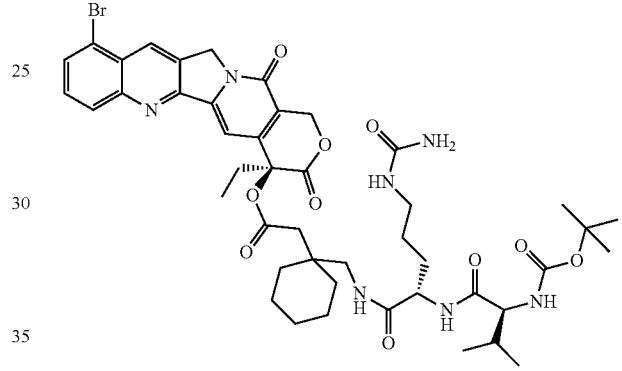

N-(tert-butoxycarbonyl)-L-valyl-N⁵-carbamoyl-L-ornithine (prepared as reported in WO2005/112919)(33 mg, 0.088 mmol), DCC (22 mg, 0.106 mmol) and HOBt (17 mg, 0.106 mmol) were dissolved in dry THF (2 mL) and stirred at room temperature for 3 h. To the solution was then added 4(S)-10-bromo-4-ethyl-3,14-dioxo-3,4,12,14-tetrahydro-1H -pyrano[3',4':6,7]indolizino[1,2-b]quinolin-4-yl [1-(aminomethyl)cyclohexyl]acetate hydrochloride (Comp 11) (43 mg, 0.073 mmol) and 4-dimethylaminopyridine (23 mg, 0.188 mmol). The reaction was stirred at room temperature for 40 min then, 20 mL of water were added. The water solution was extracted with DCM (20 mL) and then washed twice with water (10 mL). The organic phase was separated, dried over Na$_2$SO$_4$, the solvent was removed under reduced pressure and the crude reside was purified by flash chromatography on silica gel (eluant DCM:MeOH, 98:2 to 95:5 v/v) to yield the title compound as a white powder (40 mg, yield 58%).

ESI MS: m/z 936-938 (MH+)

$^1$H NMR (499.8 MHz, CH$_3$CN-d$_3$) δ ppm 0.80 (d, J=6.8 Hz, 3 H), 0.85 (d, J=6.8 Hz, 3 H), 0.97 (t, J=7.4 Hz, 3 H), 1.29-1.58 (m, 13 H), 1.37 (s, 9 H), 1.68-1.74 (m, 1 H), 1.94-2.02 (m, 1 H), 2.15-2.24 (m, 2 H), 2.44 (d, J=13.9 Hz, 1 H), 2.56 (d, J=13.9 Hz, 1 H), 2.90-2.98 (m, 1 H), 3.17-3.29 (m, 2 H), 3.36 (dd, J=13.9, 7.0 Hz, 1 H), 3.79-3.86 (m, 1 H), 4.44 (m, 1 H), 4.68 (br.s., 2 H), 5.17 (br. s., 1 H), 5.21-5.31 (m, 2 H), 5.39 (d, J=16.9 Hz, 1 H), 5.50 (d, J=7.5 Hz, 1 H), 5.57 (d, J=16.9 Hz, 1 H), 6.90 (br. s., 1 H), 6.96 (d, J=7.9 Hz, 1 H), 7.21 (s, 1 H), 7.72 (dd, J=8.5, 7.5 Hz, 1 H), 8.00 (d, J=7.5 Hz, 1 H), 8.15 (d, J=8.5 Hz, 1 H), 8.86 (s, 1 H).

Analogously the following compounds can be prepared:

N-(tert-butoxycarbonyl)-L-valyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-$N^5$-carbamoyl-L-omithinamide

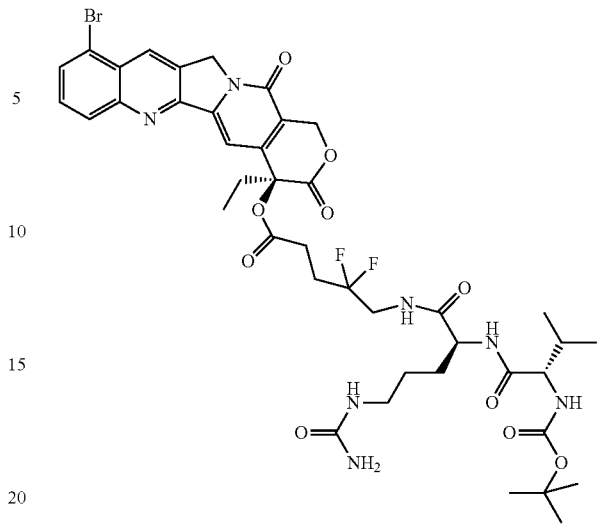

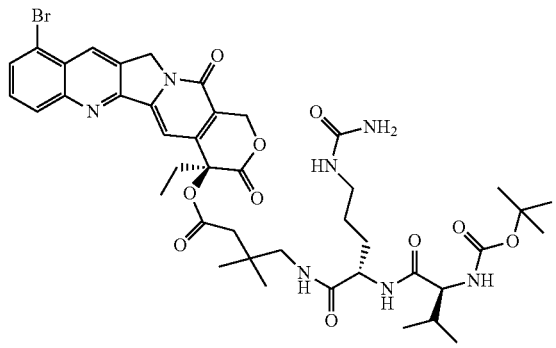 [SMILES: CC[C@@]1(OC(=O)CC(C)(C)CNC(=O)[C@H](CCCNC(N)=O)NC(=O)[C@@H](NC(=O)OC(C)(C)C)C(C)C)C(=O)OCc2c1cc1n(c2=O)Cc2cc3c(Br)cccc3nc2-1]

ESI MS: m/z 896-898 (MH$^+$)

N-(tert-butoxycarbonyl)-L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-$N^5$-carbamoyl-L-omithinamide ESI MS: m/z 918-920 (MH$^+$)

Deprotection

Deprotection of the intermediates prepared in step 6a was carried out under similar conditions reported above giving the compounds below:

L-valyl-N-[4-({[(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)carbamoyl]oxy}methyl)phenyl]-$N^5$-carbamoyl-L-omithinamide (Id), Comp. 12 [L=null; W=(IIIj); Z=Citrulline-Valine; RM=null]

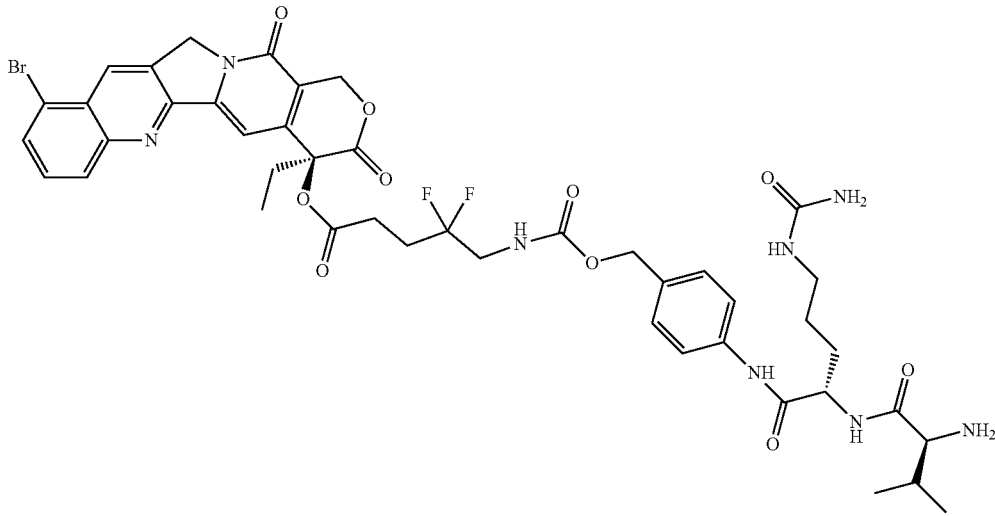 [SMILES: CC[C@@]1(OC(=O)CCC(F)(F)CNC(=O)OCc2ccc(NC(=O)[C@H](CCCNC(N)=O)NC(=O)[C@@H](N)C(C)C)cc2)C(=O)OCc2c1cc1n(c2=O)Cc2cc3c(Br)cccc3nc2-1]

ESI MS: m/z 967-969 (MH$^+$)

L-valyl-N-[4-(1{[(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)carbamoyl]oxy}methyl)phenyl]-$N^5$-carbamoyl-L-omithinamide (Id), Comp. 13 [L=null; W=(IIIj); Z=Citrulline-Valine; RM=null]

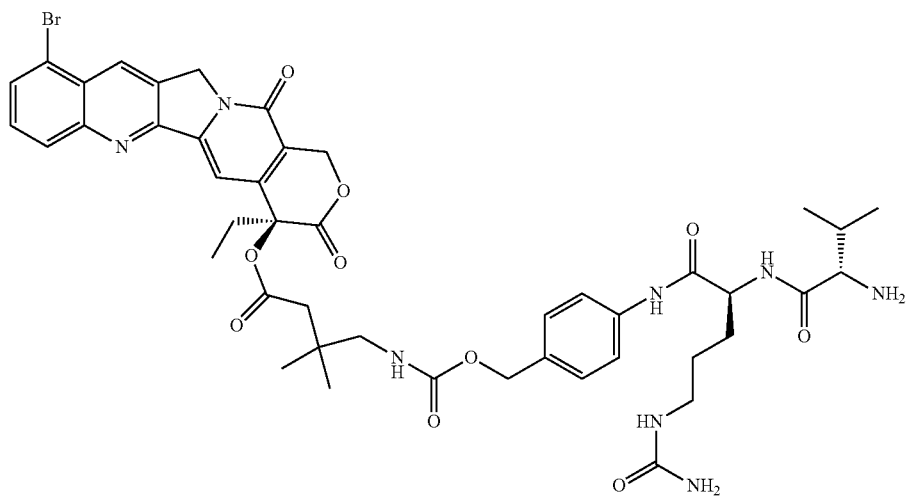 [SMILES: CC[C@@]1(OC(=O)CC(C)(C)CNC(=O)OCc2ccc(NC(=O)[C@H](CCCNC(N)=O)NC(=O)[C@@H](N)C(C)C)cc2)C(=O)OCc2c1cc1n(c2=O)Cc2cc3c(Br)cccc3nc2-1]

ESI MS: m/z 945-947 (MH+)

L-valyl-N-(4-{[({1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}carbamoyl)oxy]methyl}phenyl)-$N^5$-carbamoyl-L-omithinamide (Id), Comp. 14 [L=null; W=(IIIj); Z=Citrulline-Valine; RM=null]

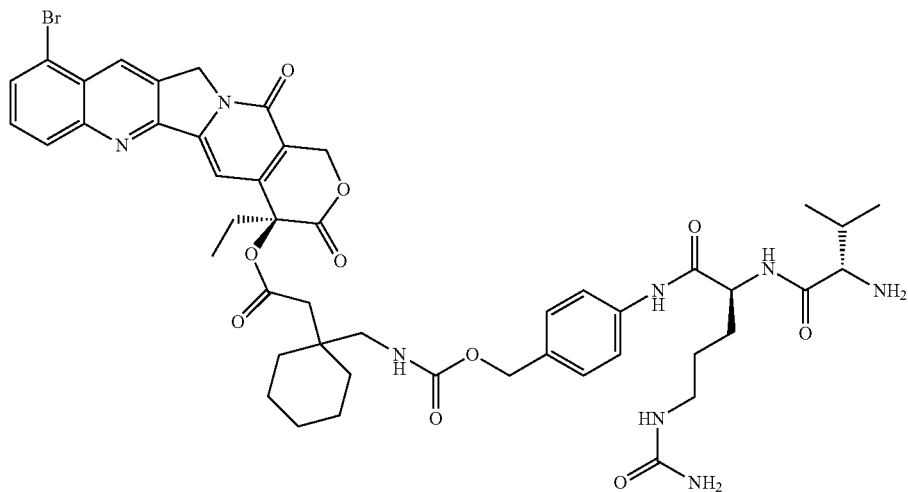 [SMILES: CC[C@@]1(OC(=O)CC2(CNC(=O)OCc3ccc(NC(=O)[C@H](CCCNC(N)=O)NC(=O)[C@@H](N)C(C)C)cc3)CCCCC2)C(=O)OCc2c1cc1n(c2=O)Cc2cc3c(Br)cccc3nc2-1]

ESI MS: m/z 985-9847 (MH+)

L-valyl-N-{1-(2-{[(4S)-10-bromo-4-ethyl-3,14-dioxo-3,4,12,14-tetrahydro-1H-pyrano[3',4':6,7]indolizino[1,2-b]quinolin -4-yl]oxy}-2-oxoethyl)cyclohexyl]methyl}-N5-carbamoyl-L-omithinamide (Id), Comp. 25 [L=null; W=(IIIa); Z=Citrulline-Valine; RM=null]

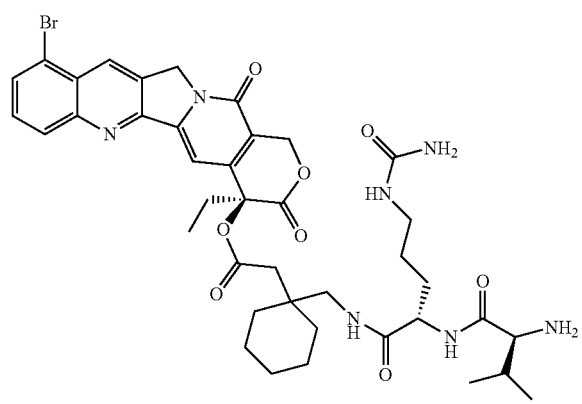 [SMILES: CC[C@@]1(OC(=O)CC2(CNC(=O)[C@H](CCCNC(N)=O)NC(=O)[C@@H](N)C(C)C)CCCCC2)C(=O)OCc2c1cc1n(c2=O)Cc2cc3c(Br)cccc3nc2-1]

ESI MS: m/z 936-838 (MH⁺)
L-valyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-N5-carbamoyl-L-omithinamide (Id), Comp. 26 [L=null; W=(IIIa); Z=Citrulline-Valine; RM=null]

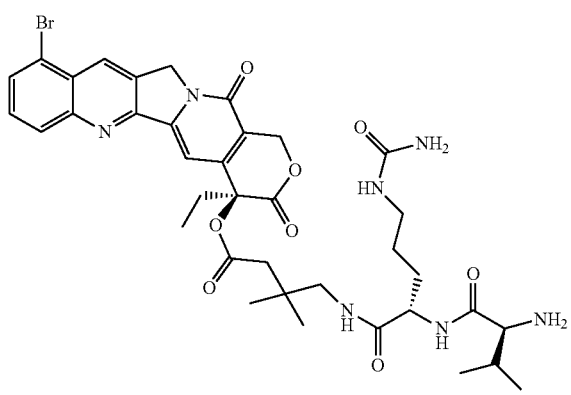 [SMILES: CC[C@@]1(OC(=O)CC(C)(C)CNC(=O)[C@H](CCCNC(N)=O)NC(=O)[C@@H](N)C(C)C)C(=O)OCc2c1cc1n(c2=O)Cc2cc3c(Br)cccc3nc2-1]

ESI MS: m/z 796-799 (MH⁺)
L-valyl-N-(5-{[(4S)-10-bromo-4-ethyl-3,14-dioxo-3,4,12,14-tetrahydro-1H-pyrano[3',4':6,7]indolizino[1,2-b]quinolin-4yl]oxy}-2,2-difluoro-5-oxopentyl)-N5-carbamoyl-L-omithinamide (Id), Comp. 27 [L=null; W=(IIIa); Z=Citrulline-Valine; RM=null]

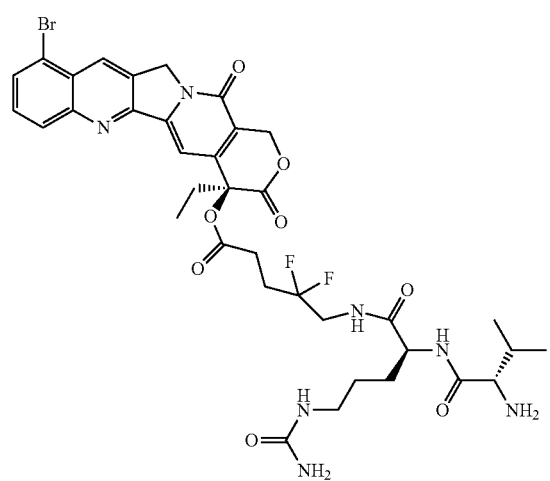 [SMILES: CC[C@@]1(OC(=O)CCC(F)(F)CNC(=O)[C@H](CCCNC(N)=O)NC(=O)[C@@H](N)C(C)C)C(=O)OCc2c1cc1n(c2=O)Cc2cc3c(Br)cccc3nc2-1]

ESI MS: m/z 818-820 (MH⁺)

Step 7

N-[6-(2,5-dioxo-2,5-dihydro-1H-pyrrol-1-yl)hexanoyl]-L-valyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl)}-N⁵-carbamoyl-L-omithinamide (I), Comp. 17 [L=null; W=(IIIa); Z=Citrulline-Valine; RM=(Va)]

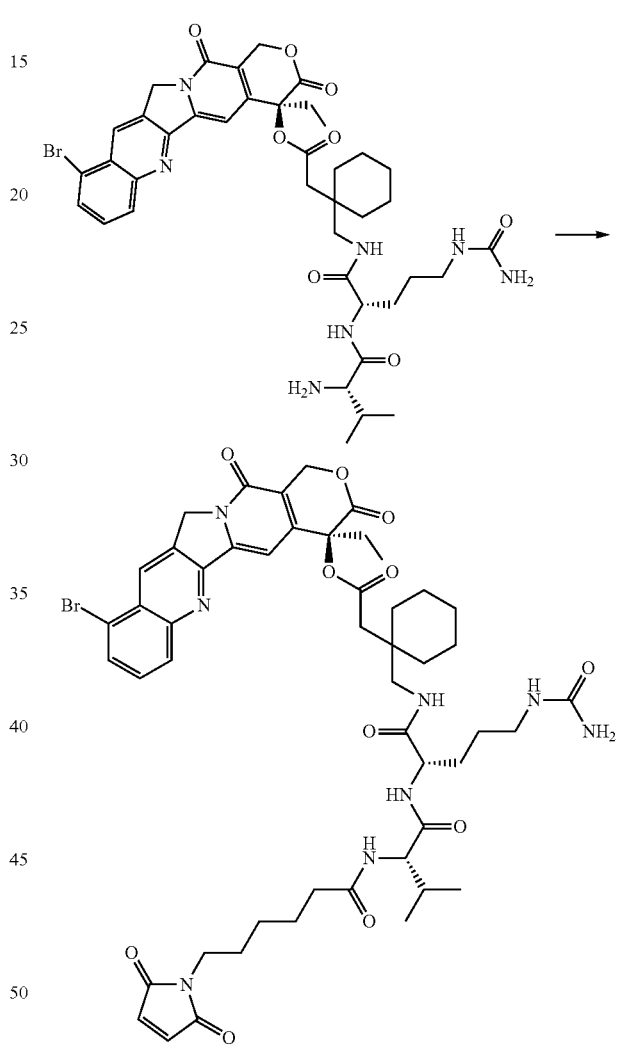

6-(2,5-dioxo-2,5-dihydro-1H-pyrrol-1-yl)hexanoic acid (12 mg, 0.053 mmol), DCC (13.3 mg, 0.063 mmol) and HOBt (10 mg, 0.063 mmol) were dissolved in dry THF (2 mL) and stirred at room temperature for 3 h. The suspension was filtered and to the THF solution L-valyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-N5-carbamoyl-L-omithinamide (Comp. 25) (15 mg, 0.018 mmol) and 4-dimethylaminopyridine (6.6 mg, 0.055 mmol) were added dropwise. The reaction was stirred at room temperature for 20 min then, 20 mL of water were added. The water solution was extracted with DCM (20 mL) and then washed twice with water (10 mL). The organic phase was separated, dried over Na$_2$SO$_4$, the solvent was removed under reduced pressure and the crude reside was purified by flash chromatography on silica gel (eluant DCM:MeOH, 97:3 to 95:5 v/v) to yield the title compound as a white powder (14 mg, yield 78%).

ESI MS: m/z 1029-1031 (MH$^+$)

$^1$H NMR (499.8 MHz, CH$_3$CN-d$_3$) ppm 0.83 (d, J=6.4 Hz, 3 H), 0.84 (d, J=6.4 Hz, 3 H), 0.97 (t, J=7.4 Hz, 3 H), 1.19-1.59 (m, 19 H), 1.69-1.77 (m, 1 H), 1.99-2.06 (m, 1 H), 2.13-2.24 (m, 4 H), 2.43 (d, J=13.8 Hz, 1 H), 2.57 (d, J=13.8 Hz, 1 H), 2.94-3.01 (m, 1 H), 3.11-3.20 (m, 1 H), 3.24 (dd, J=13.6, 5.9 Hz, 1 H), 3.31 (dd, J=13.6, 6.7 Hz, 1 H), 3.39 (t, J=7.1 Hz, 2 H), 4.08 (dd, J=8.0, 5.9 Hz, 1 H), 4.32-4.41 (m, 1 H), 4.68 (br.s., 2 H), 5.19 (br. s., 1 H), 5.22-5.32 (m, 2 H), 5.39 (d, J=17.0 Hz, 1 H), 5.57 (d, J=17.0 Hz, 1 H), 6.58 (d, J=8.0 Hz, 1 H), 6.70 (s, 2 H), 6.86 (m, 1 H), 7.02 (d, J=7.9 Hz, 1 H), 7.22 (s, 1 H), 7.73 (dd, J=8.5, 7.5 Hz, 1 H), 8.00 (d, J=7.5 Hz, 1 H), 8.15 (d, J=8.5 Hz, 1 H), 8.87 (s, 1 H).

Analogously, the following compounds can be prepared:

N-[6-(2,5-dioxo-2,5-dihydro-1H-pyrrol-1-yl)hexanoyl]-L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-N$^5$-carbamoyl-L omithinamide (I), Comp. 16 [L=null; W=(IIIa); Z=Citrulline-Valine; RM=(Va)]

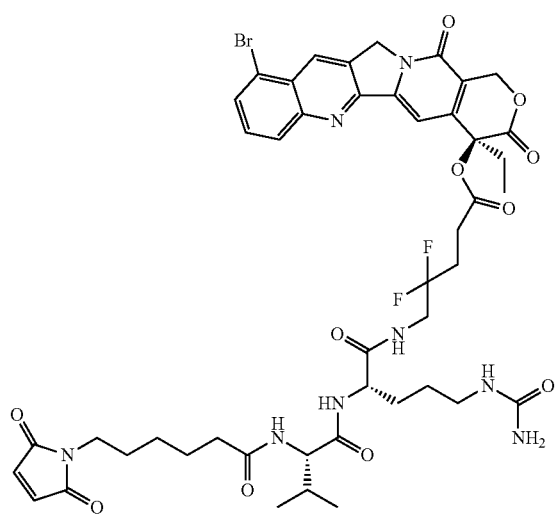 [SMILES: CC[C@@]1(OC(=O)CCC(F)(F)CNC(=O)[C@H](CCCNC(N)=O)NC(=O)[C@@H](NC(=O)CCCCCN2C(=O)C=CC2=O)C(C)C)C(=O)OCc2c1cc1n(c2=O)Cc2cc3c(Br)cccc3nc2-1]

ESI MS: m/z 1011-1013 (MH$^+$)

N-[6-(2,5-dioxo-2,5-dihydro-1H-pyrrol-1-yl)hexanoyl]-L-valyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-N$^5$-carbamoyl-L-omithinamide (I), Comp. 18 [L=null; W=(IIIa); Z=Citrulline-Valine; RM=(Va)]

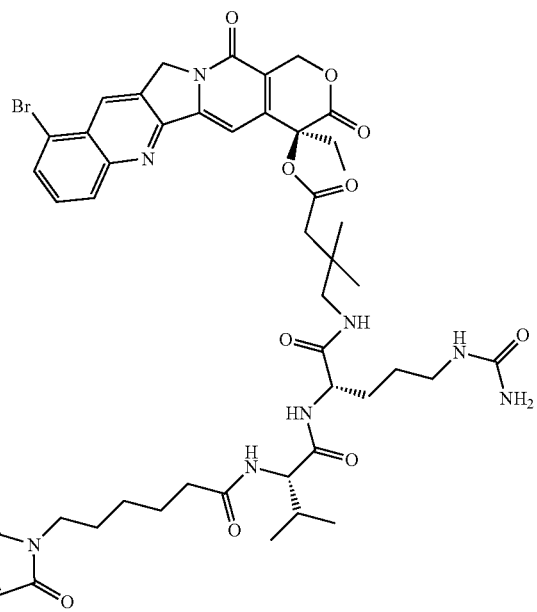

ESI MS: m/z 989-991 (MH$^+$)

N-[6-(2,5-dioxopyrrolidin-1-yl)hexanoyl]-L-valyl-N-[4-({[(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)carbamoyl]oxy}methyl)phenyl]-N$^5$-carbamoyl-L-omithinamide (I), Comp. 15 [L=null; W=(IIIj); Z=Citrulline-Valine; RM=(Va)]

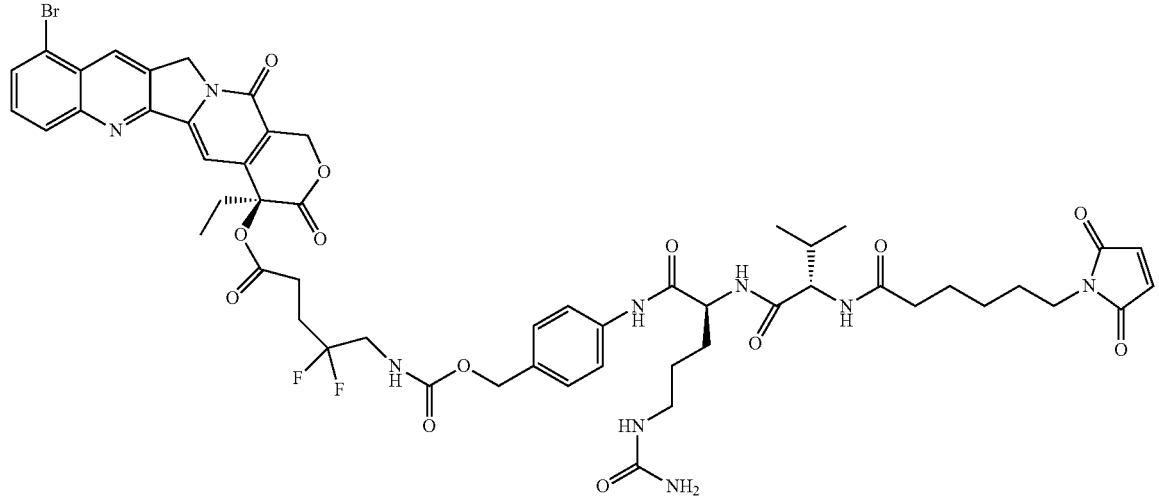 [SMILES: CC[C@@]1(OC(=O)CCC(F)(F)CNC(=O)OCc2ccc(NC(=O)[C@H](CCCNC(N)=O)NC(=O)[C@@H](NC(=O)CCCCCN3C(=O)C=CC3=O)C(C)C)cc2)C(=O)OCc2c1cc1n(c2=O)Cc2cc3c(Br)cccc3nc2-1]

ESI MS: m/z 1162-1164 (MH⁺) N-(3-carboxypropanoyl)-L-valyl-N-(5-{[(4S)-10-bromo-4-ethyl-3,14-dioxo-3,4,12,14-tetrahydro-1H -pyrano[3',4':6,7]indolizino[1,2-b]quinolin-4-yl]oxy}-2,2-difluoro-5-oxopentyl)-N⁵-carbamoyl-L-omithinamide (I), Comp. 19 [L=null; W=(IIIa); Z=Citrulline-Valine; RM=(Vn)]

N-(3-carboxypropanoyl)-L-valyl-N-(4-{[(4S)-10-bromo-4-ethyl-3,14-dioxo-3,4,12,14-tetrahydro-1H -pyrano[3',4':6,7]indolizino[1,2-b]quinolin-4-yl]oxy}-2,2-dimethyl-4-oxobutyl)-N⁵-carbamoyl-L-omithinamide (I), Comp. 21 [L=null; W=(IIIa); Z=Citrulline-Valine; RM=(Va)]

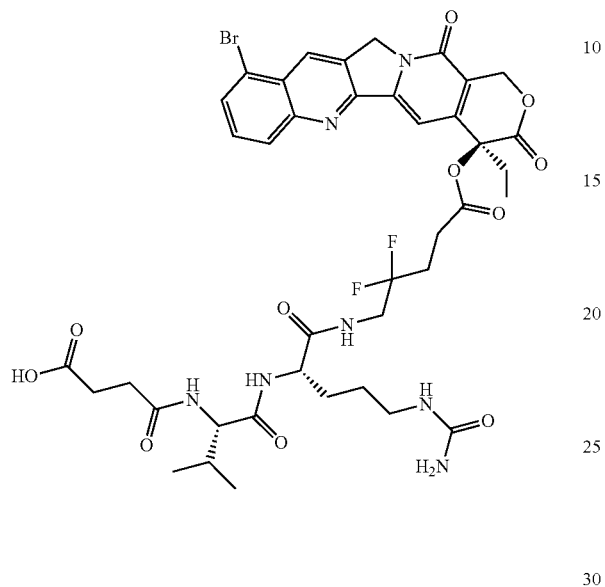

ESI MS: m/z 918-920 (MH⁺)

N-(3-carboxypropanoyl)-L-valyl-N-{[1-(2-{[(4S)-10-bromo-4-ethyl-3,14-dioxo-3,4,12,14-tetrahydro-1H -pyrano[3',4':6,7]indolizino[1,2-b]quinolin-4-yl]oxy}-2-oxoethyl)cyclohexyl]methyl}-N⁵-carbamoyl-L-omithinamide (I), Comp. 20 [L=null; W=(IIIa); Z=Citrulline-Valine; RM=(Vn)]

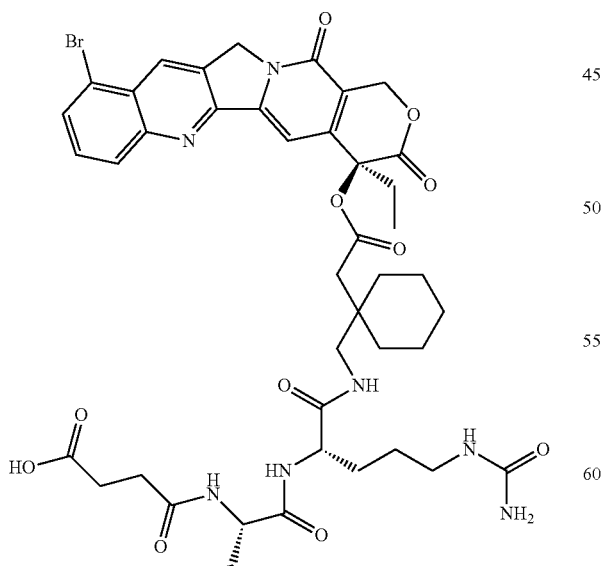

ESI MS: m/z 936-938 (MH⁺)

ESI MS: m/z 896-898 (MH⁺)

N-[6-(2,5-dioxo-2,5-dihydro-1H-pyrrol-1-yl)hexanoyl]-L-phenylalanyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-L-leucinamide (I), Comp. 22 [L=null; W=(IIIa); Z=Glicine-Leucine-Phenylalanine; RM=(Va)]

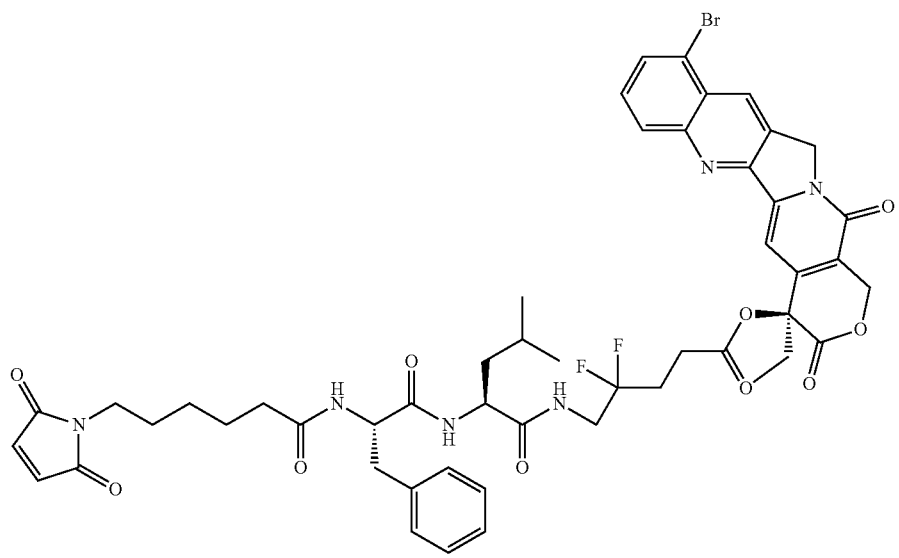

ESI MS: m/z 1015-1017 (MH+)

N-[6-(2,5-dioxo-2,5-dihydro-1H-pyrrol-1-yl)hexanoyl]-L-phenylalanyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-L-leucinamide (I), Comp. 23 [L=null; W=(IIIa); Z=Glicine-Leucine-Phenylalanine; RM=(Va)]

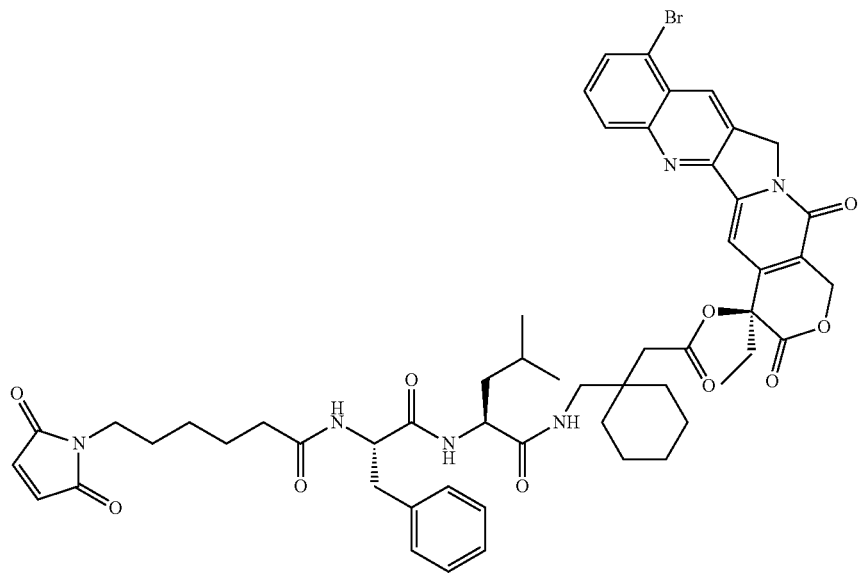 [SMILES: CC[C@@]1(OC(=O)CC2(CNC(=O)[C@H](CC(C)C)NC(=O)[C@H](Cc3ccccc3)NC(=O)CCCCCN3C(=O)C=CC3=O)CCCCC2)C(=O)OCc2c1cc1n(c2=O)Cc2cc3c(Br)cccc3nc2-1]

ESI MS: m/z 1033-12035 (MH+)

N-[6-(2,5-dioxo-2,5-dihydro-1H-pyrrol-1-yl)hexanoyl]-L-phenylalanyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-L-leucinamide (I), Comp. 24 [L=null; W=(IIIa); Z=Glicine-Leucine-Phenylalanine; RM=(Va)]

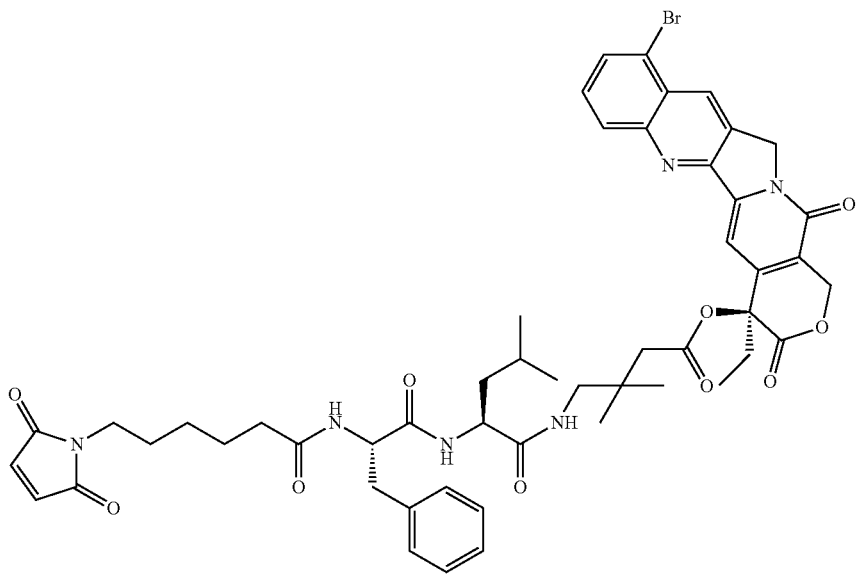 [SMILES: CC[C@@]1(OC(=O)CC(C)(C)CNC(=O)[C@H](CC(C)C)NC(=O)[C@H](Cc2ccccc2)NC(=O)CCCCCN2C(=O)C=CC2=O)C(=O)OCc2c1cc1n(c2=O)Cc2cc3c(Br)cccc3nc2-1]

ESI MS: m/z 993-995 (M+)

Synthesis of Intermediates:

Methyl 3,3-dimethyl-4-nitrobutanoate

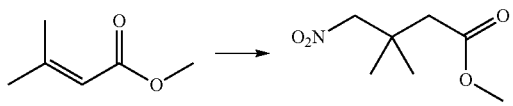

Ethyl 3,3-dimethylacrylate (6.1 mL, 46.7 mmol) was dissolved in nitromethane (13.5 mL) and DBU (7.6 mL, 50.8 mmol) was added. The mixture was stirred at room temperature for 24 h. Et$_2$O (40 mL) was added and the solution was washed with 1M HCl (2×20 mL) and then with water (20 mL). The organic phase was dried over Na$_2$SO$_4$ and the solvent was evaporated under reduced pressure. The product was purified by flash chromatography (DCM) to provide the title compound (6.5 g, 79% yield) as colorless oil.

$^1$H NMR (499.8 MHz, DMSO-d$_6$) δ ppm 1.08 (s, 6 H) 2.44 (s, 2 H) 3.60 (s, 3 H) 4.58 (s, 2 H)

Analogously, starting from ethyl cyclohexylideneacetate the following compound has been prepared:

ethyl[1-(nitromethyl)cyclohexyl]acetate

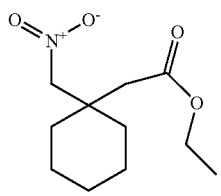 [SMILES: CCOC(=O)CC1(C[N+](=O)[O-])CCCCC1]

4-amino-3,3-dimethylbutanoic acid hydrochloride

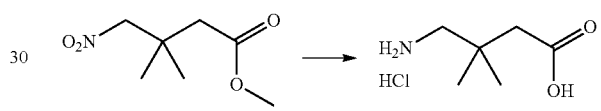

3,3-Dimethyl-4-nitro-butyric acid methyl ester (1.0 g, 5.7 mmol) was dissolved in THF (40 mL) followed by addition of 10% palladium on activated charcoal (400 mg) and a solution of ammonium formate (10 mL, 25% w/w in water). The reaction mixture was stirred, under nitrogen atmosphere for 48 h. Palladium was removed by filtration and the filtrate was extracted with DCM (2×40 mL). The organic phases were dried over Na$_2$SO$_4$ and the solvent was evaporated under reduced pressure to give 4,4-dimethyl-2-pyrrolidinone intermediate. This compound was added to a mixture of concentrated HCl (15 mL) and water (15 mL) and the resulting mixture refluxed at 110° C. for 20 h. After cooling to room temperature the mixture was evaporated to give 4-amino-3,3-dimethyl-butyric acid hydrochloride (560 mg, 52% yield) as a brown solid.

$^1$H NMR (499.8 MHz, DMSO-d$_6$) δ ppm 0.99 (s, 6 H) 2.2.26 (s, 2 H) 2.78 (q, 2 H)

Analogously, starting from ethyl [1-(nitromethyl)cyclohexyl]acetate the following compound has been prepared:

[1-(aminomethyl)cyclohexyl]acetic acid hydrochloride

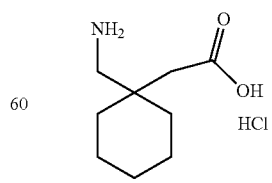

$^1$H NMR (499.7 MHz, DMSO-d$_6$) δ ppm 1.25-1.50 (m, 10 H) 2.40 (s, 2 H) 2.90 (s, 2 H) 7.99 (br. s., 3 H) 12.36 (br. s., 1 H).

4-[(tert-butoxycarbonyl)amino]-3,3-dimethylbutanoic acid

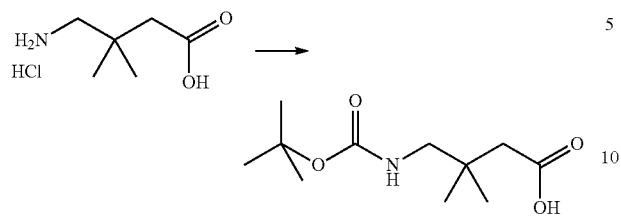

Di-tert-butyl dicarbonate (600 mg, 2.85 mmol) was added to a mixture of 4-amino-3,3-dimethyl-butyric acid hydrochloride (400 mg, 2.38 mmol) in tert-butyl alcohol (2.4 mL) and 2N NaOH (2.4 mL). The reaction was stirred at room temperature for 4 h and acetic acid (0.18 mL) was added. The mixture was extracted with EtOAc (3×10 mL), the combined organic phases were dried over $Na_2SO_4$ and then evaporated under reduced pressure. The residue was purified by flash chromatography (DCM/MeOH 98.5/1.5) to provide the title compound (110 mg, 20%). $^1$H NMR (499.8 MHz, DMSO-$d_6$) δ ppm 0.89 (s, 6 H) 1.38 (s, 9 H) 2.06 (s, 2 H) 2.86 (d, 2 H)

Analogously, starting from [1-(aminomethyl)cyclohexyl]acetic acid hydrochloride the following compound has been prepared:

(1-{[(tert-butoxycarbonyl)amino]methyl}cyclohexyl)acetic acid

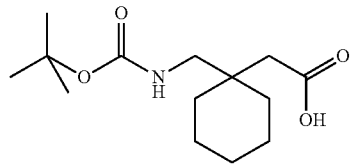 [SMILES: CC(C)(C)OC(=O)NCC1(CC(=O)O)CCCCC1]

$^1$H NMR (400.5 MHz, DMSO-$d_6$) δ ppm 1.21-1.53 (m, 10 H) 1.37 (s, 9 H) 2.15 (s, 2 H) 3.03 (d, J=6.5 Hz, 2 H) 6.55 (t, J=6.5 Hz, 1 H) 11.96 (br.s., 1 H).

4-nitrophenyl 4-[(tert-butoxycarbonyl)amino]-3,3-dimethylbutanoate

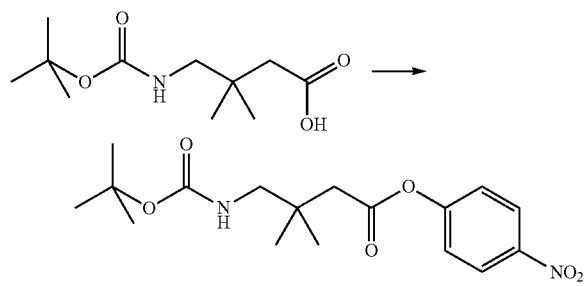

To a solution of 4-[(tert-butoxycarbonyl)amino]-3,3-dimethylbutanoic acid (90 mg, 0.389 mmol) and 4-nitrophenol (54 mg, 0.389 mmol) in anhydrous THF (1 mL), DCC (96.3 mg, 0.467 mmol) was added. The reaction was stirred for 2 h at room temperature and then the white solid formed was removed by filtration. The filtrate was evaporated under reduced pressure and finally purified by flash chromatography (DCM) to provide the title compound (80 mg, 58%).

ESI MS: m/z 353 (MH$^+$)

$^1$H NMR (499.8 MHz, DMSO-$d_6$) δ ppm 0.99 (s, 6 H) 1.39 (s, 9 H) 2.49 (signal partially overlapped by DMSO signal, 2 H) 2.95 (d, J=6.5 Hz, 2 H) 6.99 (d, J=6.5 Hz, 1 H) 7.39-7.49 (m, 2 H) 8.27-8.34 (m, 2 H).

Analogously, starting from (1-{[(tert-butoxycarbonyl)amino]methyl}cyclohexyl)acetic acid the following compound has been prepared:

4-nitrophenyl (1-{[(tert-butoxycarbonyl)amino]methyl}cyclohexyl)acetate

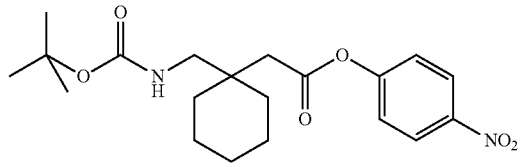 [SMILES: CC(C)(C)OC(=O)NCC1(CC(=O)Oc2ccc([N+](=O)[O-])cc2)CCCCC1]

ESI MS: m/z 393 (MH$^+$)

$^1$H NMR (499.7 MHz, DMSO-$d_6$) δ ppm 1.09-1.57 (m, 10 H) 1.37 (s, 9 H) 2.55 (s, 2 H) 3.10 (d, J=6.4 Hz, 2 H) 6.86 (t, J=6.4 Hz, 1 H) 7.44 (d, J=9.0 Hz, 2 H) 8.30 (m, d, J=9.0 Hz, 2 H).

The invention claimed is:

1. A compound of formula (I)

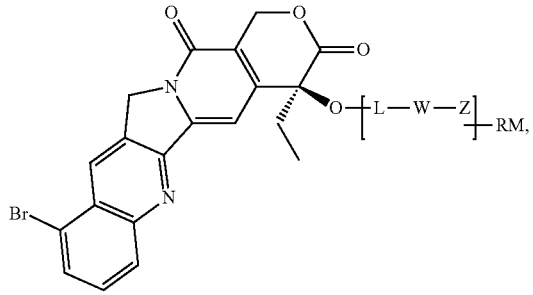

wherein:

L is null or a group selected from:

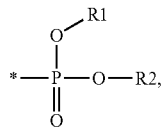

—NHCO—R1,   (IIa)

—NHCONH—R1,   (IIb)

—NHCOO—R1,   (IIc)

—NH—R1,   (IId)

(IIe)

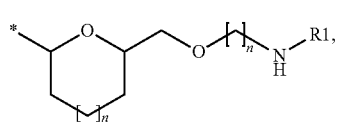

(IIf)

-continued

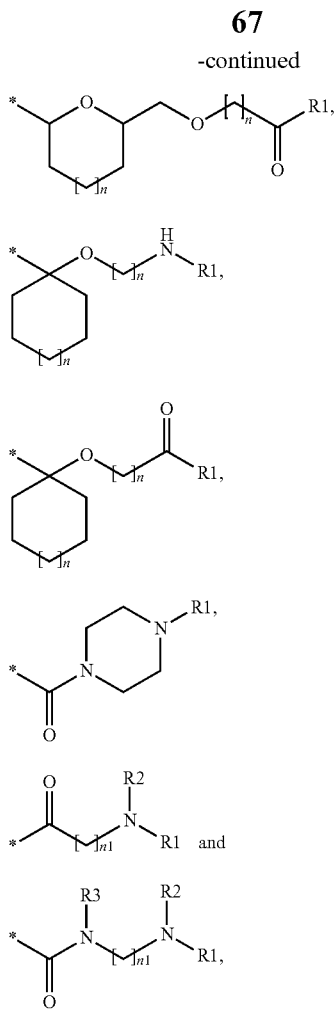

wherein:
R1, R2 and R3 are, each independently, null, hydrogen, hydroxy or an optionally substituted group selected from linear or branched $C_1$-$C_4$ alkyl, linear or branched $C_1$-$C_4$ hydroxyalkyl, linear or branched $C_1$-$C_4$ sulfhydrylalkyl, linear or branched $C_1$-$C_4$ aminoalkyl, linear or branched $C_1$-$C_4$ alkylcarbonyl and linear or branched $C_1$-$C_4$ alkoxycarbonyl;
each of n is independently an integer from 0 to 2; and n1 is an integer from 0 to 5;
W is null or a group selected from:

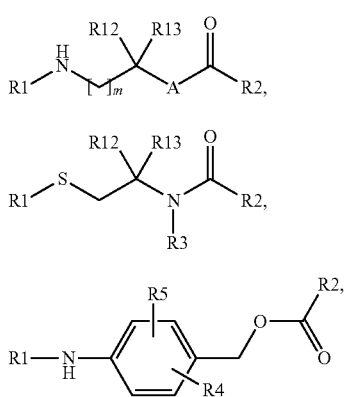

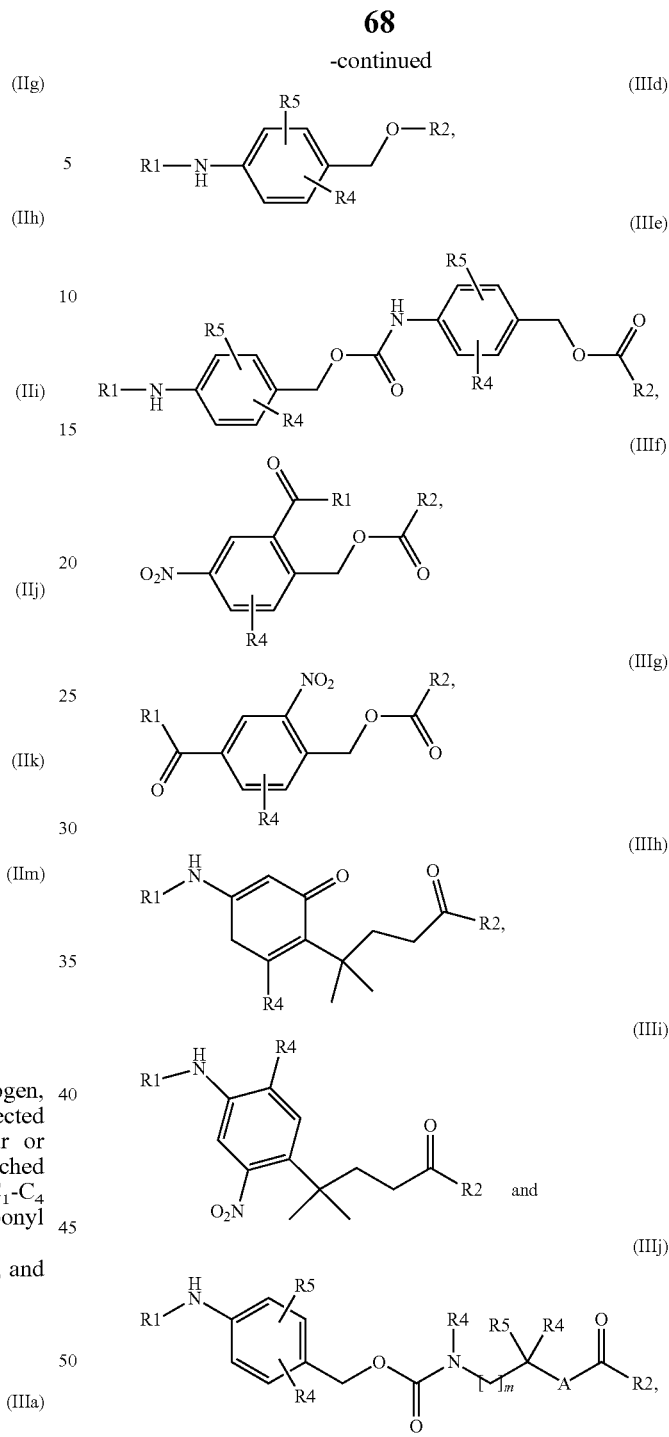

wherein:
one of R1 and R2 is null and the other is as defined above;
R3 is as defined above;
R4 and R5 are, each independently, halogen, methyl, ethyl or linear or branched $C_1$-$C_4$ hydroxyalkyl;
m is an integer from 0 to 3;
A is $C_1$-$C_3$ alkyl, $CH_2NH$, NH or N—R4, wherein R4 is as defined above; and
R12 and R13 are, each independently, hydrogen, halogen, methyl, ethyl, linear or branched $C_1$-$C_4$ hydroxyalkyl, linear or branched $C_1$-$C_4$ haloalkyl, or R12 and R13, taken together, form a 3- to 6-membered carbocycle;

Z is independently null or

Z1, wherein Z1 is a dipeptide or a tripeptide, linked via its C-terminus to W, or to L when W is null, or to oxygen when W and L are both null, wherein the C-terminal aminoacid residue of the dipeptide or of the tripeptide is selected from glycine, leucine, alanine, arginine and citrulline; and the N-terminal aminoacid residue is selected from any natural or unnatural aminoacid; and, in the case of the tripeptide, the middle aminoacid residue is selected from alanine, valine, leucine, isoleucine, methionine, phenylalanine and proline;

Z2, wherein Z2 is a group selected from:

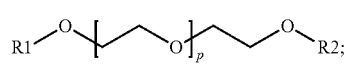 (IVa)

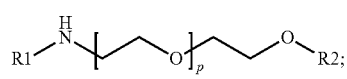 (IVb)

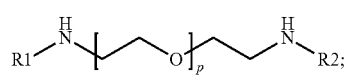 (IVc)

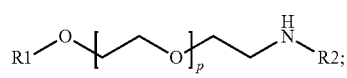 (IVd)

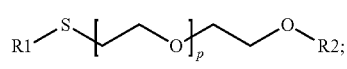 (IVe)

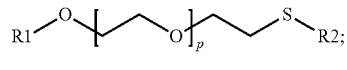 (IVf)

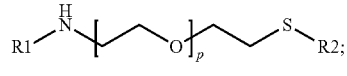 (IVg)

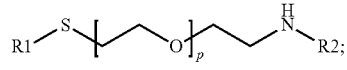 (IVh)

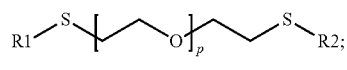 (IVi)

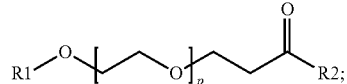 (IVj)

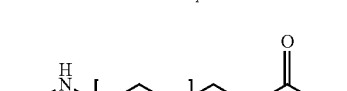 (IVk)

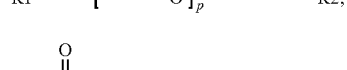 (IVm)

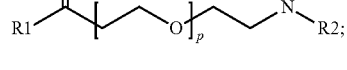 (IVn)

-continued

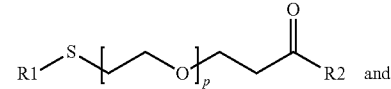 (IVo) and

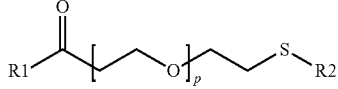 (IVp)

wherein
one of R1 and R2 is null and the other is as defined above, and
p is an integer from 1 to 20;

Z1-Z2, wherein Z1 and Z2 are as defined above;

RM is a group selected from:

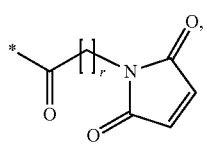 (Va)

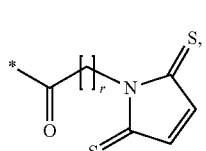 (Vb)

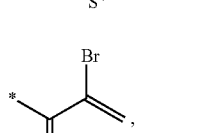 (Vc)

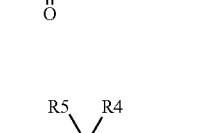 (Vd)

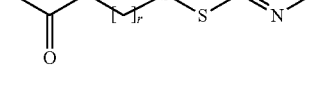 (Ve)

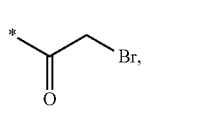 (Vf)

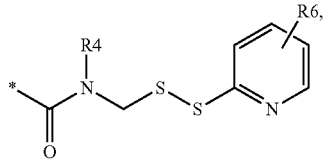 (Vg)

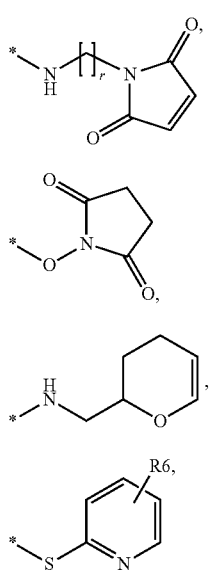
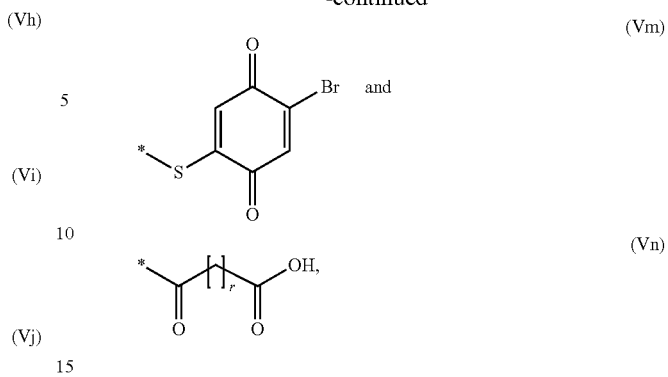
wherein R4 and R5 are as defined above;
R6 is $C_1$-$C_3$ alkyl or an electron-withdrawing group, comprising $NO_2$ and CN group;
r is an integer from 0 to 7;
or a pharmaceutically acceptable salt thereof.
2. A compound according to claim 1, wherein Z is a group selected from:
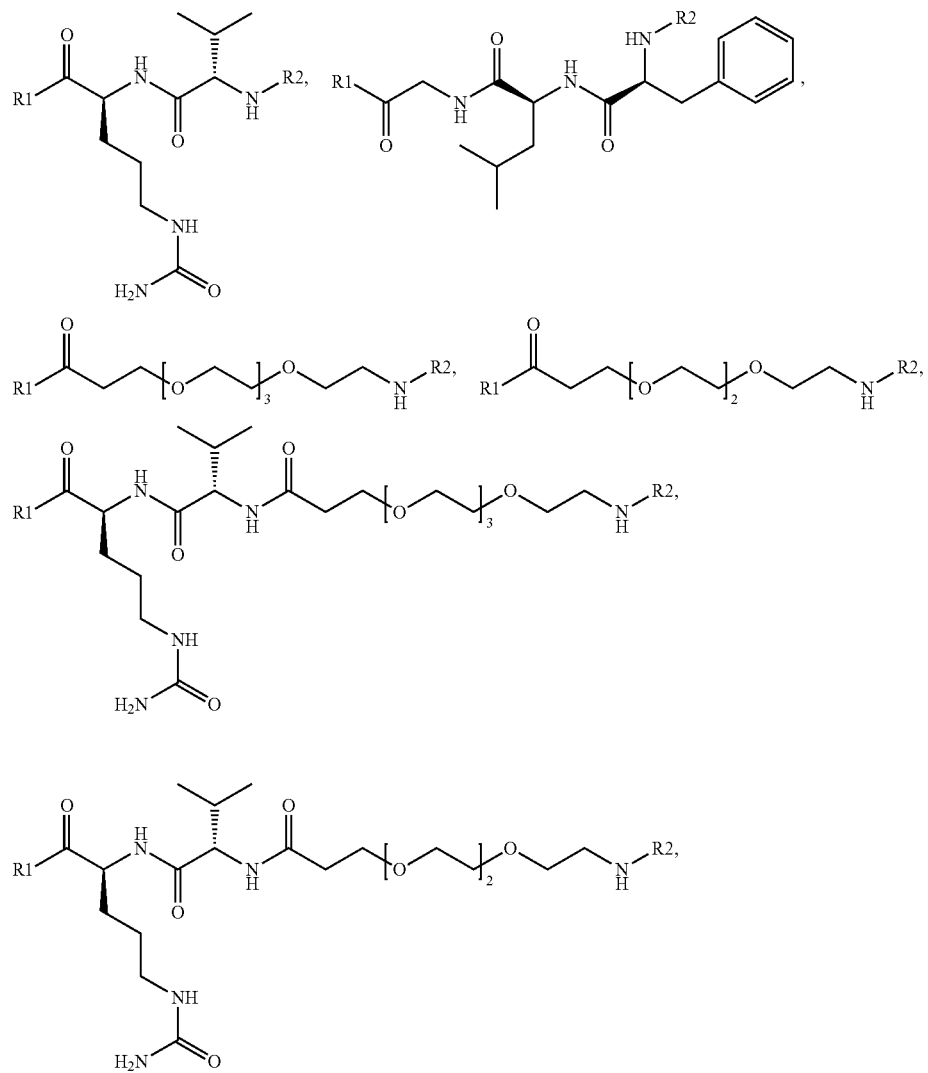

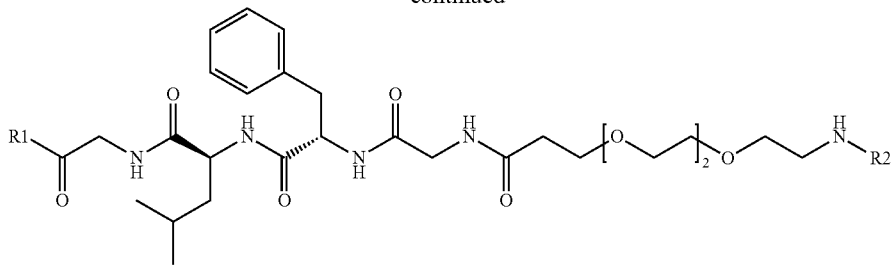

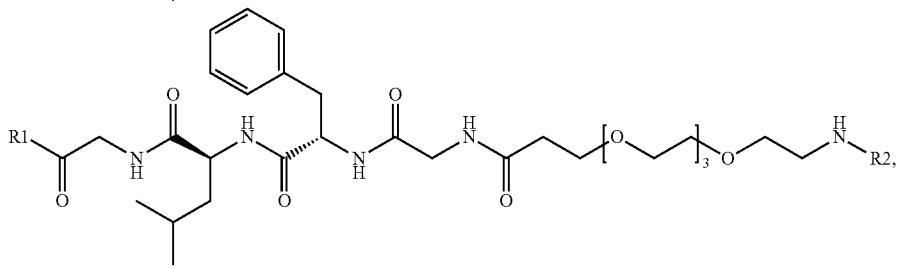

and wherein
one of R1 and R2 is null and the other is as defined in claim 1;
or a pharmaceutically acceptable salt thereof.

3. A compound according to claim 1, or a pharmaceutically acceptable salt thereof, which is selected from the group consisting of:

(4S)-10-bromo-4-ethyl-3,14-dioxo-3,4,12,14-tetrahydro-1H-pyrano[3',4':6,7]indolizino[1,2 -b]quinolin-4-yl N-[6-(2,5-dioxo-2,5-dihydro-1H-pyrrol-1-yl)hexanoyl]-L-phenylalanyl-L -leucylglycinate;

N-[6-(2,5-dioxo-2,5-dihydro-1H-pyrrol-1-yl)hexanoyl]-L-valyl-N-{4-[({[4-({[(4S)-10-bromo-4-ethyl-3,14-dioxo-3,4,12,14-tetrahydro-1H-pyrano[3',4':6,7]indolizino[1,2-b]quinolin-4-yl]oxy}carbonyl)piperazin-1-yl]carbonyl}oxy)methyl]phenyl}-$N^5$-carbamoyl-L-omithinamide;

(4S)-10-bromo-4-ethyl-3,14-dioxo-3,4,12,14-tetrahydro-1H-pyrano[3',4':6,7]indolizino[1,2-b]quinolin-4-yl 4-[6-(2,5-dioxo-2,5-dihydro-1H-pyrrol-1-yl)hexanoyl]piperazine-1-carboxylate;

N-[6-(2,5-dioxo-2,5-dihydro-1H-pyrrol-1-yl)hexanoyl]-L-valyl-N-[4-({[{2-[({[(4S)-10-bromo -4-ethyl-3,14-dioxo-3,4,12,14-tetrahydro-1H-pyrano[3',4':6,7]indolizino[1,2-b]quinolin-4-yl]oxy}carbonyl) (methyl)amino]ethyl} (methyl)carbamoyl} oxy}methyl)phenyl]-$N^5$-carbamoyl -L-omithinamide;

N-[6-(2,5-dioxopyrrolidin-1-yl)hexanoyl]-L-valyl-N-[4-({[(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)carbamoyl]oxy}methyl)phenyl]-$N^5$-carbamoyl-L-omithinamide;

N-[6-(2,5-dioxo-2,5-dihydro-1H-pyrrol-1-yl)hexanoyl]-L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-$N^5$-carbamoyl-L-omithinamide;

N-[6-(2,5-dioxo-2,5-dihydro-1H-pyrrol-1-yl)hexanoyl]-L-valyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-$N^5$-carbamoyl-L-omithinamide;

N-[6-(2,5-dioxo-2,5-dihydro-1H-pyrrol-1-yl)hexanoyl]-L-valyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-$N^5$-carbamoyl-L-omithinamide;

N-(3-carboxypropanoyl)-L-valyl-N-(5-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-$N^5$-carbamoyl-L-omithinamide;

N-(3-carboxypropanoyl)-L-valyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-$N^5$-carbamoyl-L-omithinamide;

N-(3-carboxypropanoyl)-L-valyl-N-(4-{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-$N^5$-carbamoyl-L-omithinamide;

N-[6-(2,5-dioxo-2,5-dihydro-1H-pyrrol-1-yl)hexanoyl]-L-phenylalanyl-N-(5{[(4S)-10-bromo-4-ethyl-3,14-dioxo-3,4,12,14-tetrahydro-1H-pyrano[3',4':6,7]indolizino[1,2-b]quinolin-4-yl]oxy}-2,2-difluoro-5-oxopentyl)-L-leucinamide;

N-[6-(2,5-dioxo-2,5-dihydro-1H-pyrrol-1-yl)hexanoyl]-L-phenylalanyl-N-{[1-(2-{[(4S)-10-bromo-4-ethyl-3,14-dioxo-3,4,12,14-tetrahydro-1H-pyrano[3',4':6,7]indolizino[1,2-b]quinolin-4-yl]oxy}-2-oxoethyl)cyclohexyl]methyl}-L-leucinamide; and N-[6-(2,5-dioxo-2,5-dihydro-1H-pyrrol-1-yl)hexanoyl]-L-phenylalanyl-N-(4-{[(4S)-10-bromo -4-ethyl-3,14-dioxo-3,4,12,14-tetrahydro-1H-pyrano[3',4':6,7]indolizino[1,2-b]quinolin-4-yl]oxy}-2,2-dimethyl-4-oxobutyl)-L-leucinamide.

4. A pharmaceutical composition comprising a therapeutically effective amount of a compound of formula (I) or a pharmaceutically acceptable salt thereof, as defined in claim 1, and at least one pharmaceutically acceptable excipient, carrier or diluent.

5. A pharmaceutical composition according to claim 4 further comprising one or more chemotherapeutic agents.

6. A product comprising a compound of formula (I) or a pharmaceutically acceptable salt thereof, as defined in claim 1, and one or more chemotherapeutic agents, as a combined preparation for simultaneous, separate or sequential use in anticancer therapy.

7. A method for treating ovarian cancer, which comprises administering to a mammal in need thereof an effective amount of a compound of formula (I) or a pharmaceutically acceptable salt thereof, as defined in claim 1.

8. A method according to claim 7, wherein the mammal in need thereof is a human.

\* \* \* \* \*